(12) United States Patent
Ricciardi et al.

(10) Patent No.: US 10,675,369 B1
(45) Date of Patent: *Jun. 9, 2020

(54) ROTATING OBJECT HOLDER FOR MULTI-FUNCTION SANITIZATION, DISINFECTION, AND STERILIZATION IN A CABINET

(71) Applicant: Altapure, LLC, Mequon, WI (US)

(72) Inventors: Carl L. Ricciardi, Tomahawk, WI (US); Jonathan J. Ricciardi, Wausau, WI (US); Jonathan D. Yoder, Goshen, IN (US); Jim Gerend, Cedar Grove, WI (US); Dean Kreider, Cedarsburg, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,738

(22) Filed: Jan. 7, 2020

Related U.S. Application Data

(63) Continuation-in-part of application No. 16/132,561, filed on Sep. 17, 2018, now Pat. No. 10,596,289, which is a continuation-in-part of application No. 15/947,896, filed on Apr. 9, 2018.

(60) Provisional application No. 62/483,486, filed on Apr. 10, 2017.

(51) Int. Cl.
*A61L 2/08* (2006.01)
*A61L 2/26* (2006.01)

(52) U.S. Cl.
CPC .............. *A61L 2/084* (2013.01); *A61L 2/26* (2013.01); *A61L 2202/11* (2013.01)

(58) Field of Classification Search
CPC ...... A61L 2/26; A61L 2/22; A61L 2/24; A61L 2202/14; A61L 2202/24
See application file for complete search history.

(56) References Cited

U.S. PATENT DOCUMENTS

| | | | | |
|---|---|---|---|---|
| 5,645,748 A | * | 7/1997 | Schiffmann | A61L 2/12 219/710 |
| 8,062,590 B1 | | 11/2011 | Ricciardi et al. | |
| 8,506,900 B1 | * | 8/2013 | Ricciardi | A61L 2/04 422/292 |
| 2003/0219354 A1 | * | 11/2003 | Hlavinka | A61M 1/3683 422/22 |

* cited by examiner

*Primary Examiner* — Sean E Conley
*Assistant Examiner* — Brendan A Hensel
(74) *Attorney, Agent, or Firm* — Donald J. Ersler

(57) ABSTRACT

A multi-function product disinfection cabinet preferably includes a sealed test cabinet, a high level disinfection system, a dehumidifier and an electrical function tester. The sealed test cabinet preferably includes a sealed test chamber, a rear dehumidifier chamber and a rear droplet chamber. The high level disinfection system includes an aerosol blower, an aerosol generator and an aerosol control module. The aerosol blower blows a disinfectant from the aerosol generator into the disinfection chamber. A pivoting cable holder for a multi-function disinfection cabinet preferably includes a pivoting cable tube, a mounting bracket, a motor with gear reduction, a motor controller and two snap switches. The mounting bracket is attached to an outside sidewall of a disinfection chamber. The pivoting cable tube rotates in the disinfection chamber. The motor rotates the pivoting cable tube. The motor controller and two snap switches are used to control directional rotation of the motor.

17 Claims, 17 Drawing Sheets

ROTATING OBJECT HOLDER FOR MULTI-FUNCTION SANITIZATION, DISINFECTION, AND STERILIZATION IN A CABINET

CROSS-REFERENCES TO RELATED APPLICATIONS

This is a continuation-in-part application, which claims priority from application Ser. No. 16/132,561 filed on Sep. 17, 2018, which claims priority from application Ser. No. 15/947,896 filed on Apr. 9, 2018, which claims the benefit of provisional application No. 62/483,486 filed on Apr. 10, 2017.

BACKGROUND OF THE INVENTION

Field of the Invention

The present invention relates generally to the sanitization, disinfection, high level disinfection, sterilization, and/or drying, of any contaminated and/or biological contaminated, object(s), equipment(s), machine(s), device(s), accessory(s), and/or tool(s), such as those found, and without limitation, in the medical, dental, scientific, life science(s), and/or industrial, commercial fields and/or industries, such as, but not limited to any, object(s), such as, but not limited to any, instrument(s) equipment(s), sensor(s), power supply(s), medical equipment(s), dental equipment(s), industrial equipment(s), product(s), accessory(s), device(s), tool(s), sensor(s), probe(s), ultrasonic probe(s), ultrasonic imaging device(s), esophageal imaging device(s), component(s), parts(s), component(s), cable(s), conduit(s), wire(s), dental device(s), object(s), equipment(s), accessory(s), tool(s), cord(s), tube(s), pipe(s), wire(s), hose(s), conduit(s), scope(s), endoscope(s), medical device(s), ultrasonic device(s), imaging device(s), scope(s), electronic(s), cable(s), cutting tool(s), irrigation device(s), suction device(s), vacuum device(s), drilling device(s), stethoscope(s), umbilical connector(s), computer mouse(s) and attached cable(s), clamp(s), cord(s), blood pressure measuring and reporting device(s), stethoscope(s), ECG device(s), SPO2 device(s), temperature sensing device(s), TOCO device(s), and/or patient monitoring equipment or device(s), including, but not limited to, any of their or associated, part(s), accessory(s), device(s), and component(s), (Herein after called "object(s)"), and more specifically to a multi-function surface treatment chamber(s) and/or enclosure(s), and even more specifically to a multi-function decontamination, sanitization, disinfection, high-level disinfection, and/or sterilization cabinet(s), for one or more surface(s) of one or more various object(s), which provides and allows for preferably, but not limited to, the decontamination, sanitization, disinfection, high-level disinfection, sterilization, and/or drying, of various object(s), preferably, and without limitation, at any suitable and effective temperature(s), and more preferably and without limitation, at any suitable and effective low temperature(s), and any suitable and effective types of testing of these same object(s), device(s), and/or their various part(s) and component(s), while achieving, without limitation, at least any efficacious log reduction of any pathogens, and more preferably and without limitation, at least a greater than 6 log reduction of any bio-burden and/or any pathogens in less than 10 minutes, but at least and without limitation, within less than 60 minutes.

More generally, and without limitation, the present invention relates to an apparatus and method that can not only treat and then dry the various surfaces of one or more of any object(s), and any of their part(s) and component(s), in a manner to achieve a result on their one or more surface(s) such as, but not limited to any, decontamination, sanitization, disinfection, high-level disinfection, and/or sterilization, but also preferably and without limitation, conduct one or more of any suitable and effective test(s) on the said object(s), and more preferably, and without limitation, conduct one or more of any suitable and effective function and/or electrical test(s) on the one or more of any object(s), for their one or more of any function(s) and performance(s), and more preferably and without limitation, conduct one or more of any suitable and effective test(s) for one or more of any, optical, physical, mechanical, and/or electrical function(s) and performance(s), at any one or more of any suitable time(s) before, during, and/or after, any part of any one or more of any, surface treatment(s), surface drying(s), and/or decontamination and/or treatment cycle(s).

The present invention also, and without limitation, relates generally to the decontamination, sanitization, disinfection, high level disinfection, sterilization, and/or drying, of one or more of any object(s), but preferably and without limitation, any pathogenic contaminated object(s) and/or any potentially contaminated object(s), such as, but not limited to any, instrument(s) equipment(s), accessory(s), device(s), and/or tool(s), such as, but not limited to any, sensor(s), probe(s), device(s), ultrasonic probe(s), ultrasonic imaging device(s), esophageal imaging device(s), component(s), parts(s), component(s), cable(s), conduit(s), wire(s), dental device(s), object(s), equipment(s), accessory(s), tool(s), cord(s), tube(s), pipe(s), wire(s), hose(s), conduit(s), scope(s), endoscope(s), medical device(s), dental device(s), ultrasonic device(s), imaging device(s), scope(s), electronic(s), cable(s), cutting tool(s), irrigation device(s), suction and/or vacuum device(s), drilling device(s), stethoscope(s), umbilical connector(s), computer mouse(s) and attached cable(s), clamp(s), cord(s), blood pressure measuring and reporting device(s), stethoscope(s), and/or patient monitoring equipment, where the said one or more object(s) is effectively and releasably held and/or supported by one or more of any suitable and effective object(s) support(s) and/or holder(s), where any effective, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), passes the one or more object(s) from the one or more of any suitable and effective first support(s), member(s), and/or holder(s), to the one or more of any suitable and effective second support(s), member(s), and/or holder(s), and also where any suitable and effective, reverse, reverse direction, reflecting, returning, backward, and/or opposite, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), passes the one or more said object(s) back to the first said one or more support(s), member(s), and/or holder(s). Also without being limited, the said object(s) can be passed back and forth between the said one or more first and second support(s), member(s), and/or holder(s) during various processing steps such as, but not limited to: treatment and/or decontamination of the various surface(s) within the treatment chamber(s) including, but not limited to the various surface(s) of the one or more of any object(s) present inside of the treatment chamber(s), drying the various surface(s) within the treatment chamber(s).

Discussion of the Prior Art

The prior art does not teach or suggest, and without limitation, a multi-function enclosure and/or chamber product, for the sanitization, disinfection, high-level disinfection, and/or sterilization, of the surface(s) within its chamber(s) (Hereinafter called a "Multi-function Treatment Chamber(s)"), that can provide any, decontamination, sanitization, disinfection, high level disinfection, and/or sterilization, of various one or more, object(s), and without limitation, also any, directly and/or indirectly connected, handle(s), signal and/or electrical connector(s), and/or cable(s) and/or cord(s), and that can achieve a greater than 6 log reduction of any pathogens found on various treated surface(s) such as, but not limited to, MRSA, VRE, CRE, *C. Auris*, and/or *C. difficil* spores, preferably and without limitation, in less than 10 minutes, and also without being limited, at any suitable "low cost", and preferably, and without limitation, at a cost less than ten dollars USD per operation cycle, and more preferably, and without limitation, less than one dollar USD per operation cycle, and even more preferably, and without limitation, less than fifty cents USD per operation cycle, and very preferably, and without limitation, less than thirty cents USD per operation cycle, and where the temperatures for both the various surface treatment(s) and drying activity(s) are both, and without limitation, "effective low temperature(s)", and preferably, and without limitation, at temperatures of 200 degree Fahrenheit or less, and more preferably, and without limitation, at temperatures of 150 degree Fahrenheit or less, and even more preferably, and without limitation, at temperatures of 120 degree Fahrenheit or less, and very preferably, and without limitation, at temperatures between 50-120 degree Fahrenheit, and extremely preferably, and without limitation, at temperatures between 85-120 degree Fahrenheit.

More specifically, the prior art does not teach or suggest a multi-function surface treatment enclosure product that can decontaminate, sanitize, disinfect, and/or sterilize, the surfaces of any one or more object(s) and then test and check the said object(s) for one or more of any, condition(s), function(s), and/or performance(s), such as, but not limited to any, electrical function(s) and/or sensory function(s), before, during, and/or after, the various object(s) surfaces are, treated, dried, and/or decontaminated, and subsequently dried. In the clinical health care setting, certain medical devices are essential for routine patient care. Generally, they are high-use medical products and/or medical devices, and are constructed of materials that are not safe for high temperature disinfection methods. Because of their various attributes such as, but not limited to, their material makeup, design and construction, length, and/or dimensions they are not regularly cleaned sufficiently and/or effectively to eliminate cross-contamination from one patient to the next. The current method of cleaning by hand using strong chemicals can degrade various parts and components of medical devices such as, but not limited to any, metal(s), plastic(s), protective coating(s), and/or seal material(s).

In addition, patient monitoring leads, probes, sensors, and other medical device(s), routinely fail through repeated use, hand cleaning, abuse, mishandling, and stress. If this condition is not timely diagnosed, these instruments and devices can be transferred from room to room, patient to patient, until eventually diagnosed and identified as defective. Inventory, storage, and availability, are major considerations in busy clinical treatment situations and areas.

Recent published scientific literature has shown that antibiotic and drug resistant pathogenic bio-burden including, but not limited to any, bacteria, mold, and fungus, commonly called "Super Bugs", are found primarily in hospital, clinical, and long term care facilities. Further, there is an unanimity of thought within the medical community, that the transmission of infectious diseases is spread from patient to patient by many vectors including, but not limited to, improperly disinfected objects.

Without limitation, because many serious diseases are spread by the hands of health care workers and by the patient touching the surfaces in their immediate vicinity, it is paramount that all surfaces of various objects and patient related equipment and object(s), are at least effectively, disinfected, but even more preferably and without limitation, at least effectively high-level disinfected, but very preferably at least effectively, and without limitation, sterilized.

Trial and error is a common approach practiced by medical personnel in selecting suitable and reliable cable and/or wire leads, probes and devices. Currently, lacking a comprehensive solution for the disinfection, high-level disinfection, and/or sterilization, storage and grouping of like devices, hospitals have adopted a variety of less than optimal, methods. This function usually defaults to the clinical end user at the most inopportune or inconvenient time.

Most hospitals have trained biomedical technicians that can be dispatched on an as needed basis to assist in troubleshooting patient monitoring equipment issues, but unavailability and prior commitment usually forces users to borrow the needed components from available sources creating inventory confusion and uncertainty as to the cleanliness, function, performance, and safety of the equipment.

This practice often results in questionable or defective objects remaining in clinical areas available for others to use without knowing its, functional condition(s), electrical status(s), or whether it had been effectively disinfected and/or sterilized. Often times clinical accessory items cannot be determined to be acceptable or unacceptable based on visual inspections alone. When defective objects are inter-mixed with compliant items, the patient is put at risk for electrical injury, incorrect diagnosis, contamination, and/or infection. Troubleshooting various medical object(s), in a clinical setting, with limited availability of appropriate test equipment, or trained staff, can impact diagnosis and timeliness of patient treatment. Without being limited, sophisticated electronic test equipment necessary to diagnose electronic failure is typically not available in the area where these devices are routinely used.

Having convenient and timely access to various, medical object(s) and device(s), that have been effectively tested, as well as effectively decontaminated, sanitized, disinfected, high-level disinfected, and/or sterilized, will greatly improve quality and safety for both patients and clinical operators. Without being limited, the diagnosis and removal of any defective and/or contaminated, object(s), device(s), and equipment(s), can also reduce and/or eliminate the risk of various negative consequences. Without being limited, the decontamination, sanitization, disinfection, high-level disinfection, and/or sterilization, of the said any, object(s), adds a level of protection against possible cross contamination from various sources known in the medical art.

Manual cleaning and checking of various object(s), such as, but not limited to any medical object(s), is often times inconsistent, inadequate and/or incomplete. Without being limited, a system whereby reusable and/or high-usage reusable components undergo one or more various activities, in any effective order(s), such as, but not limited to being, tagged, tracked, function tested, treated and/or decontaminated, packaged, stored, and/or inventoried, will greatly improve work flow and operations in the clinical setting. U.S. Pat. No. 8,062,590 to Ricciardi et al. discloses methods and apparatuses for applying agent to objects.

Accordingly, and without limitation, there is a clearly felt need in the art for a multi-function treatment chamber(s) and/or multi-function treatment cabinet(s), that can provide effective, decontamination, sanitization, disinfection, sterilization, and/or drying, of all surface(s) of any one or more treated object(s) and preferably, and without limitation, at any suitable and effective low temperature(s), and preferably and without limitation, also test the object(s) in any suitable and effective manner known to those skilled in the art, all in a manner that is also preferably and without limitation, cost effective.

Without being limited, the prior art is also silent with respect to treating, decontaminating, and/or drying, the various surface(s) of various object(s) within one or more sealed treatment chamber(s), where the said one or more object(s) is effectively and releasably held and/or supported by one or more of any suitable and effective object(s) support(s) and/or holder(s), and where any effective, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), passes the one or more object(s) from the one or more of any suitable and effective first support(s), member(s), and/or holder(s), to the one or more of any suitable and effective second support(s), member(s), and/or holder(s), and the any effective reverse, reverse direction, opposite, reflecting, returning, backward, and/or opposite, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), passes the one or more object(s) from the one or more of any suitable and effective second support(s), member(s), and/or holder(s), back to the one or more of any suitable and effective first support(s), member(s), and/or holder(s), where the said one or more object(s) can be moved back and forth between the first and second support(s), member(s), and/or holder(s), one or more times, before, during, and/or after, one or more of any suitable and effective activity(s) such as, but not limited to any, treating, sanitizing, disinfecting, sterilizing, decontaminating, and/or drying, of any surface(s) within any treatment chamber(s), including any surface(s) of the said one or more object(s).

SUMMARY OF THE INVENTION

The present invention provides, without limitation, a multi-function surface treatment enclosure and/or multi-function treatment cabinet(s) and/or chamber(s) product, that can both decontaminate, sanitize, disinfect, high-level disinfect, sterilize, and/or effectively dry, one or more of any surface(s), on one or more object(s), and then test, qualify, benchmark, and/or check, the function(s), status(s), and/or performance(s) of the said object(s). Without being limited, one or more of any effective, means, process(s), method(s), chemical treatment(s), and/or technology(s), known to those skilled in the art can be used to decontaminate, sanitize, disinfect, high-level disinfect, and/or sterilize, (Herein called "Decontaminate") the one or more of any targeted surfaces and/or treated object surfaces, within the one or more of any suitable and effective treatment enclosure(s), cabinet(s), and/or chamber(s), such as, but not limited to any, aerosol(s), combination of any aerosol(s), light of any effective wavelengths, UV light, vaporized hydrogen peroxide (VHP) gas(s) and/or vapor(s), Peroxyacetic Acid (PAA) gas(s) and/or vapor(s), ozone gas(s) and/or vapor(s), plasma(s), any one or more combination(s) and/or mixture(s) of one or more of any aerosol(s), gas(s), plasma(s), and/or vapor(s), such as, but not limited to any, containing any hydrogen peroxide and/or ozone, any one or more chemical agent(s) in aerosol form, and/or any one or more chemical agent(s) in any gas(s), vapor(s), and/or aerosol(s) form(s) (Herein called "Treatment Agent(s)"). Also without being limited, the multi-function treatment cabinet(s) and/or chamber(s) product can provide the effective decontamination of one or more of any suitable object(s), while also achieving preferably, and without limitation, at least a 6 log reduction(s), but at least any effective log reduction(s), of any, pathogen(s), bio burden(s), virus(s), bacteria(s), spore(s), mold(s), and/or fungus(s), preferably in less than 60 minutes, more preferably in less than 45 minutes, even more preferably in less than 30 minutes, very preferably in less than 20 minutes, and extremely preferably in less than 10 minutes.

Without limitation, the multi-function treatment cabinet(s) and/or chamber(s) product can include at least one sealed treatment chamber(s) that can also, without limitation, function as a sealed testing chamber(s) (Herein called "Treatment Chamber(s)"), at least one decontamination system(s), but preferably and without limitation, at least one of any effective, decontamination, disinfection, high-level disinfection, and/or sterilization, system(s), at least one dehumidifier(s), at least one filter(s), at least one of any suitable, test equipment(s) tester(s), function testor(s), and/or electrical function tester(s), at least one wireless control interface(s), at least one bar code reader(s), compliance reporting software, and tracking software. Without being limited, at least one thermal printer can also be suitable and effectively located, preferably and without limitation, so it can be effectively accessed at the exterior front and/or side(s) of the multi-function treatment chamber(s) product. Without being limited, the multi-function treatment cabinet(s) and/or chamber(s) product or otherwise the sealed test cabinet and/or treatment chamber, preferably includes at least one sealed treatment and/or test chamber(s), a top equipment space, a bottom equipment space, a rear dehumidifier chamber and a rear droplet chamber.

Without limitation, the multi-function treatment cabinet(s) and/or chamber(s) product can also have a more preferable form, design, and function. This more preferred alternative design does not use a dehumidifier to effectively remove the one or more of any deposited and/or deployed, treatment agent(s), gases(s), vapor(s), aerosol(s), liquid(s), liquid film(s), agent(s), and/or chemical residue(s), from the various surfaces inside of the sealed treatment chamber(s), including the various treated object(s) surface(s), but instead flows filtered heated air through the sealed treatment chamber(s).

Without being limited, the more preferred multi-function treatment cabinet(s) and/or chamber(s) product can include at least one effectively resealable treatment chamber(s) that can also function as a test chamber(s) (Herein also called "Sealed Treatment Chamber(s)"), with at least one effectively resealable door(s), where the sealed treatment chamber(s) is constructed using one or more of any suitable and effective design(s) for both the chamber(s), cabinet(s), and/or door(s), that are known to those skilled in the art. Without limitation, the interior of the sealed treatment chamber(s) can be any suitable and effective size, volume, shape, geometry, length, width, and/or height. It is preferred, without limitation, that the various components and their materials of construction that are used, are at least FDA compliant, and compatible with any of the one or more decontamination agent(s) and/or treatment agent(s), such as, but not limited to any, agent(s), and/or chemical(s), used to treat, decontaminate, sanitize, disinfect, high-level disinfect, and/or sterilize, the surface(s) of the various treated object(s), all in a manner known to those skilled in the art.

Without being limited, the interior of the said more preferred sealed treatment chamber(s), effectively communicates with at least one of any suitable and effective apparatus(s), technology(s), and/or system(s), (Herein called "Decontamination System(s)") that can decontaminate, sanitize, disinfect, high-level disinfect, sterilize, and/or otherwise decontaminate, with one or more of any, and/or one or more of any effective combination(s) of, any effective, light(s), gas(s), vapor(s), plasma(s), and/or aerosol(s), preferably, and without limitation, the various targeted surface(s) within the said sealed treatment chamber(s), and more preferably, and without limitation, effectively all of the various surfaces exposed at any time(s) to any, air, aerosol(s), gas(s), and/or vapor(s), that can be introduced into, flowed through, and/or be present, inside of, the sealed treatment chamber(s) at any suitable and effective time(s) during the one or more of any treatment cycle(s). It is preferred, without limitation, that the various object(s) surface(s) inside of the said sealed treatment chamber(s), are effectively treated with one or more of, and/or any one or more effective combination(s) of, any effective, gas(s), vapor(s), and/or aerosol(s), that can sanitize, disinfect, high-level disinfect, sterilize, and/or otherwise decontaminate the object(s) surface(s). It is also preferred, without limitation, that the various object(s) surfaces within the treatment chamber(s) are treated with one or more of any effective aerosol(s) that is generated by any suitable and effective means known to those skilled in the art such as, but not limited to any effective, ultrasonic aerosol generator(s) and/or device(s), pressurized air/gas(s) aerosol generator(s) and/or device(s), and even more preferably, and without limitation, treated with one or more of any effective aerosol(s) that are ultrasonically created as described in U.S. Pat. No. 8,062,590 to Ricciardi et al., and U.S. Pat. No. 9,551,996 to Baumgartner et al.

Without being limited, the interior of the more preferred treatment chamber(s), can also effectively communicate with at least one of any suitable and effective heater(s), apparatus(s), technology(s), and/or system(s), that can effectively dry the various surface(s) and object(s) surface(s), within the treatment chamber(s). However, it is preferred, without limitation, that at least one suitable heated air apparatus(s), as known to those skilled in the art, effectively communicates with the sealed treatment chamber(s), and effectively flows heated air, at one or more of any effective temperature(s), and at one or more of any suitable and effective time(s) during any treatment cycle(s), through the one or more said sealed treatment chamber(s) to effectively dry the various object(s) surface(s) inside of the said treatment chamber(s), at one or more of any suitable and effective time(s), and for any suitable and effective duration of time(s). Without being limited, any airflow that is flowed and/or moved into the sealed treatment chamber(s) from outside of the multi-function treatment cabinet(s) and/or chamber(s) product, can be effectively filtered, with at least one suitable and effective filter(s), all in a manner known to those skilled in the art.

Without being limited, the object(s) located inside the treatment chamber(s) can be treated and dried at one or more of any suitable and effective temperature(s), and where the temperature(s) for both the various surface treatment(s) and drying activity(s) can be, preferably, and without limitation, at any effective temperatures of 200 degree Fahrenheit or less, and more preferably, and without limitation, any effective temperatures of 150 degree Fahrenheit or less, and even more preferably, and without limitation, at any effective temperatures of 130 degree Fahrenheit or less for drying various surface(s), and very preferably, and without limitation, at any effective temperatures between 50-130 degree Fahrenheit for drying various surface(s), and extremely preferably, and without limitation, at any effective temperatures between 85-130 degree Fahrenheit for drying various surface(s).

Without being limited, the multi-function treatment cabinet(s) and/or chamber(s) product, can include any suitable and effective, electronic(s) and/or test equipment(s) for, any testing and reporting the test data for various object(s) and device(s), any electrical function testing for various apparatus(s) and/or object(s), any temperature function testing for various apparatus(s) and/or object(s), any pressure testing various apparatus(s) and/or object(s), any ultrasonic imaging diagnostic and/or testing for various apparatus(s) and/or object(s), any imaging diagnostic and/or testing for various apparatus(s) and/or object(s), any signal testing diagnostic and/or testing for various apparatus(s) and/or object(s), (Herein called "Test Equipment(s)").

Without being limited, the said test equipment(s) can be used for any suitable and effective, diagnosing, testing, qualifying, analyzing, reporting, and/or assuring, one or more of any, performance(s), accuracy(s), signal(s), electrical signal(s), gas(s) level(s) and or concentration(s), liquid pulse(s), thermal input(s), thermal output(s), pressure(s), sound(s), temperature(s), light(s), light intensity(s), power(s), waveform(s), frequency(s), thermal conductivity(s), function(s), output(s), input(s), reliability(s), and/or repeatability(s), of any, object(s).

It is preferred, without limitation, that the various said one or more of any object(s) are effectively located within the said one or more sealed treatment chamber(s), and they are effectively connected inside the said chamber(s), all in a manner known to those skilled in the art, so they can effectively communicate with one or more of any suitable and effective, testing, analyzing, qualifying, diagnosing, monitoring, and/or function testing, equipment(s), device(s), and/or apparatus(s) known to those skilled in the art, and then be effectively, tested, function tested, monitored, analyzed, qualified, and/or diagnosed, while they are still present within the said one or more preferred sealed treatment chamber(s).

It is preferred, without limitation, that the various said object(s) are effectively connected to any of the said suitable and effective, testing, analyzing, qualifying, diagnosing, monitoring, and/or function testing, equipment(s), device(s), software(s), and/or apparatus(s), before they are treated, sanitized, disinfected, high-level disinfected, sterilized, and/or otherwise decontaminated, using one or more of any suitable and effective connection(s) and/or connector(s) that are effectively located within the sealed treatment chamber(s).

It is preferred, without limitation, that one or more of any object(s) that are tested, analyzed, qualified, diagnosed, monitored, and/or function tested, such as, but not limited to any suitable, ECG device(s), SPO2 device(s), temperature sensing device(s), TOCO device(s), that are known to those skilled in the art, are connected to one or more of any suitable interface test blocks that are described in the present invention. Without being limited, the said interface test blocks can be removably positioned and/or located within the said treatment chamber(s). Also without being limited, the interface test blocks can have the ability to, and/or are designed in a manner known to those skilled in the art, so they can directly and/or indirectly communicate with one or more of any suitable and effective equipment(s), device(s), software(s), and/or apparatus(s), to effectively test, analyze, qualify, diagnose, monitor, and/or function test, the one or more of any object(s) and/or medical device(s).

Without being limited, the one or more of any object(s) located within the treatment chamber(s) can be treated, sanitized, disinfected, high-level disinfected, sterilized, decontaminated, and dried, at one or more of any suitable and effective time(s), such as, but not limited to, before, during, and/or after, they are diagnosed, tested, function tested, monitored, diagnosed, qualified, analyzed, reported on, and/or assured, but preferably, and without limitation, at least before they are diagnosed, tested, function tested, monitored, diagnosed, qualified, analyzed, reported on, and/or assured.

Without being limited, the more preferred multi-function treatment cabinet(s) and/or chamber(s) product, can also include at least one of any suitable and effectively connected, machine control software, human machine control interface(s), wireless control interface(s), bar code reader(s), compliance reporting software, wireless network communication device(s), wired network communication device(s), and tracking software.

Also, without being limited, various spaces can be designed, provided, and/or used, inside the exterior and/or external skin of the more preferred multi-function treatment cabinet(s) and/or chamber(s) product, including, but not limited to one or more of any, top equipment space(s), bottom equipment space(s), rear equipment space(s), and one or more equipment space(s) on either side of the one or more sealed treatment and/or test chamber(s) and/or cabinet(s). It is preferred, without limitation, that the various equipment(s), device(s), hardware(s), such as, but not limited to any, electrical and system control hardware(s), treatment chamber(s), test equipment(s), air heating device(s) and/or equipment(s), aerosol generating devices(s), various liquid storage container(s), air/gas(s) movement apparatus(s), blower(s), fan(s), and/or air filter(s) are at least effectively located within the multi-function treatment cabinet(s) and/or chamber(s) product and/or located effectively within the external skin(s) of the multi-function treatment cabinet(s) and/or chamber(s) product.

The decontamination system(s), heretofore described preferably, and without limitation, includes at least one airborne agent(s) blower(s), at least one aerosol generator(s), aerosol tubing(s), and at least one agent(s) control module(s). Without limitation, patent no. 9551996, Baumgartner et al. describes the elements of the said aerosol generator(s) and is herein incorporated by reference in its entirety. Without being limited, at least one inlet(s) of the airborne agent(s) blower(s) communicates with the at least one effective treatment chamber(s), that is preferably, and without limitation, effectively sealed, and that can be repeatedly opened and effectively closed and resealed, and at least one outlet of the airborne agent(s) blower(s) is connected to at least one inlet(s) of the aerosol generator(s). Also, without being limited, the airborne agent(s) blower(s) blows air into the inlet(s) of the aerosol generator(s) and can also, without limitation, assist in drawing, pushing, moving, and/or flowing, the generated aerosol(s) from and/or out of, the one or more reservoir(s) of disinfectant and/or the one or more chamber(s) in which any aerosol(s) is generated, and into the one or more aerosol tubing(s) and/or then into the one or more sealed treatment chamber(s). An inlet(s) of the aerosol tubing(s) is connected to an outlet(s) of the aerosol generator(s) and an outlet(s) of the aerosol tubing(s) communicates with the sealed treatment chamber(s). Without being limited, the agent(s) control module(s) can control the operation of the various components of the one or more various decontamination system(s).

The decontamination system(s) that supplies and/or provides the various treatment agent(s) into the treatment chamber(s), is preferably, and without limitation, located in the top equipment space. However, in the more preferred form of the multi-function treatment cabinet(s) and/or chamber(s) product, the one or more decontamination system(s) can be, and without limitation, located at one or more of any suitable and effective location(s), and preferably and without limitation, located at one or more of any suitable and effective location(s) near the treatment chamber(s), and more preferably, and without limitation, located at one or more of any suitable and effective location(s) under and/or approximate to the treatment chamber(s).

Without being limited, after the one or more of any object(s) is placed inside of the treatment chamber(s), and preferably and without limitation, interfaced with one or more of any suitable object(s) holding apparatus(s) that are effectively located inside of the said treatment chamber(s), the one or more door(s) to the treatment chamber(s) is effectively closed and sealed. Without being limited, the atmosphere(s) and/or environment(s) inside of the one or more treatment chamber(s) can be effectively processed, controlled, and/or treated, with one or more of any suitable and effective device(s) and/or apparatus(s) such as, but not limited to any, air/gas(s) heater(s), and/or dehumidification apparatus(s), so that the treatment process(s) within the treatment chamber(s) can start at one or more of any effective humidity level(s) and temperature(s) points. It is preferred, without limitation, that the atmosphere(s) and/or environment(s) inside of the treatment chamber(s) at least meets a temperature between 33 and 90 degree Fahrenheit, and a humidity level between zero to 100 percent relative humidity.

Also without being limited, once the one or more starting parameters for processing the one or more object(s) within the treatment chamber(s), such as, but not limited to any, temperature(s), and/or humidity level(s), are met for treating the said object(s), the one or more decontamination system(s) can flow one or more of any effective quantity(s) of the one or more effective treatment agent(s) into the treatment chamber(s) for any suitable and effective amount(s) of time(s). Without being limited, after the treatment chamber(s) is effectively filled with the one or more treatment agent(s), the treatment agent(s) can be allowed to dwell inside the sealed treatment chamber(s) for any effective amount(s) and/or length(s) of time(s).

Without limitation, after the said object(s) are effectively treated by the deployed treatment agent(s), the treatment agent(s) can be effectively removed from the sealed treatment chamber(s). It is preferred, without limitation, that the atmosphere(s), air/gas(s), and/or deployed treatment agent(s), within and/or from the sealed treatment chamber(s), are first flowed, circulated, and/or recirculated, through the one or more dehumidifier(s) and/or dehumidifier chamber(s), at any effective speed(s), velocity(s), and/or cubic feet per minute, where the air/gas(s) and atmosphere(s) from within the treatment chamber(s) can be dehumidified, before being flowed and/or returned back to the treatment chamber(s). This can remove, without limitation, any effective amount(s) of the treatment agent(s) and/or humidity(s), from the atmosphere(s) and/or gas(s) from within the treatment chamber(s). Any effective humidity level(s) can be reached inside the one or more treatment chamber(s) before the treated object(s) is removed from the treatment chamber(s), preferably and without limitation, by the operation of one or more of any effective dehumdification apparatus(s), but more preferably, and without limitation, with the dehumidification apparatus(s) described in the present invention, at any suitable and effective time(s) during any treatment, dehumidification, and/or drying step(s). It is preferred, without limitation, that at least any effective humidity level(s) is met, sustained, and/or attained, for the atmosphere(s) inside of the treatment cabinet(s), before the removal of the said treated object(s) from the said treatment cabinet(s), and it is more preferred, without limitation, that a humidity level of at least 70% RH or less is met, sustained, and/or attained, for the atmosphere(s) inside of the treatment cabinet(s), before the removal of the said treated object(s) from the said sealed treatment cabinet(s). Without being limited, the air/gas(s) and atmosphere(s) within the treatment chamber(s) can be dehumidified at one or more of any suitable and effective time(s) and at one or more of any suitable and effective time(s) of the treatment process(s) for the said treated object(s).

Without being limited, at one or more of any suitable and effective time(s) during the processing of the one or more said object(s), and/or preferably, and without limitation, after any suitable and effective relative humidity level(s) is met and/or created for the air/gas(s) and atmosphere(s) within the treatment chamber(s), by preferably using one or more of any suitable and effective dehumidification apparatus(s), the air/gas(s) and/or atmosphere(s) within the treatment chamber(s) can also be flowed through the one or more droplet chamber(s) where the said air/gas(s) and/or atmosphere can be heated to any effective temperature(s).

Without being limited, the air/gas(s) and/or atmosphere(s) within the treatment chamber(s) can also be flowed through one or more of any effective air/gas(s) filter(s) preferably, and without limitation, after it has moved through the one or more droplet chamber(s). The air/gas(s) and atmosphere(s) within the treatment chamber(s) can be, without limitation, flowed and/or moved through the one or more droplet chamber(s) and/or air/gas(s) filter(s), at one or more of any suitable and effective time(s), at any effective speed(s), velocity(s), and/or cubic feet per minute, and at any one or more of any suitable and effective part(s) of the treatment process(s) for the said treated object(s).

Without being limited, the atmosphere(s) and/or air/gas(s) that flows from the treatment chamber(s) and into and through the dehumidifier(s), dehumidifier chamber(s), and/ or the droplet chamber(s), can be controlled with one or more of any suitable and effective means. For example, and without limitation, the movement of the air/gas(s) and/or atmosphere(s) into and through the inlet(s) for both the dehumidifier chamber(s) and the droplet chamber(s), can be controlled by one or more of any suitable and effective valve(s) (not shown), that are known to those skilled in the art. However, preferably, and without limitation, one or more effective diverter valve(s) can be connected to and communicate with the one or more outlets from the one or more dehumidifier(s) and/or dehumidifier chamber(s) and the droplet chamber(s), and the said diverter valve(s) can control the quantity, speed, cubic feet per minute (CFM), and/or velocity of travel, of any air/gas(s) flow(s) that is flowed through either and/or both the dehumidifier(s) and/or dehumidifier chamber(s) and/or the droplet chamber(s), at any suitable and effective time(s) and for any length of time(s) during any one or more part(s) of the treatment process(s) for the said treated object(s). It is preferred, without limitation, that the one or more diverter valve(s) is used to move the entire air flow from the treatment chamber(s) and into either the dehumidifier chamber(s) or the droplet chamber(s), however, and without being limited, effective amount(s) of air/gas(s) and atmosphere(s) from the sealed treatment chamber(s) can also be controlled by the one or more diverter valve(s) to flow from the sealed treatment chamber(s) and through both the dehumidifier chamber(s) and the droplet chamber(s). Without being limited, once the air/gas(s) flow past the diverter valve(s), it can be effectively heated with one or more of any suitable and effective heater(s) located at any suitable and effective location(s), and then moved with one or more of any effective blower(s) located at any suitable and effective location(s), back into the sealed treatment chamber(s), preferably through one or more of any suitable and effective communicating diffuser(s) and/or outlet(s) located at or near the floor(s) of the sealed treatment chamber(s), but at least at any suitable and effective location(s) in, at, and/or into, the treatment chamber(s).

The one or more dehumidifier(s) and/or dehumidification system(s), if used, preferably includes at least one evaporator coil(s), at least one condenser coil(s) and at least one air conditioning compressor(s). An outlet(s) of the air conditioning compressor(s) is connected to an inlet(s) of the evaporator coil(s). The air conditioner compressor(s) pumps refrigerant through the one or more evaporator coil(s) and the one or more condenser coil(s). Without being limited, the one or more evaporator coil(s) is located inside the one or more dehumidifier chamber(s). Without being limited, the one or more condenser coil(s) is located in the one or more droplet chamber(s). Without being limited, both the dehumidifier chamber(s) and the droplet chamber(s), can be effectively located in any suitable and effective location(s) within the multi-function treatment cabinet(s) and/or chamber(s) product. Also, without being limited, both the dehumidifier chamber(s) and the droplet chamber(s) can be any suitable and effective, shape(s), size(s), geometry(s), length(s), width(s), height(s). The one or more air conditioning compressor(s) is preferably, and without limitation, located inside the bottom equipment space. Without being limited, the moisture in the air condenses on the one or more evaporator coil(s), and then preferably and without limitation drops onto one or more of any effective collection, plate(s), surface(s), and/or floor(s), where the condensate and/or liquid(s) can be effectively channeled, flowed, and then dropped into one or more of any suitable liquid collection bottle(s).

Also without being limited, at least one droplet chamber(s) can also be provided where air/gas(s) and/or atmosphere(s) from the treatment chamber(s) can move into and then through the said droplet chamber(s), where the said flowed air/gas(s) and/or atmosphere(s) can then be effectively filtered after passing through the said droplet chamber(s), by one or more of any effective air/gas(s) filter(s). Without being limited, the said one or more air/gas(s) filter(s) and/or filtration unit(s), can effectively filter any, airborne particle(s), vapor(s), and/or gas(s). Without being limited, the heat from the one or more condenser coil(s) located effectively within the said droplet chamber(s), can also help dry the various, aerosol(s), vapor(s), air, gas(s), and/or atmosphere(s), that is moved and/or flowed through the one or more droplet chamber(s), as well as the various surface(s) within the treatment chamber(s).

Without being limited, at least one diverter valve(s) is preferably located in the bottom equipment chamber and/or space. Also, without being limited, the diverter valve(s) can include, without limitation, at least one, dehumidifier chamber inlet(s), droplet chamber inlet(s), and outlet(s). Without being limited, the diverter valve(s) can directly and/or indirectly communicate with the one or more, dehumidifier chamber(s), droplet chamber(s), and/or blower(s). Without being linmited, one or more of any suitable and effective valve(s) known to those skilled in the art can be used for the diverter valve(s). Also without being limited, the one or more diverter valve(s) can shuttle between the dehumidifier chamber inlet(s) and the droplet inlet(s). Without being limited, the outlet of the diverter valve(s) can be connected to at least one inlet(s) of one or more of any suitable and effective air/gas(s) blower(s).

Without being limited, the one or more diverter valve(s) can control the flow of the air/gas(s) and/or atmosphere(s) that can be moved from the one or more treatment chamber(s), through the one or more, dehumidifier chamber(s) and/or droplet chamber(s), through one or more of any effective means to move the said air/gas(s) and/or atmosphere(s), through the one or more effective means to heat the said air/gas(s), and the return of the said air/gas(s) and/or atmosphere(s) into the said treatment chamber(s). The one or more said means to heat the said flowed and/or circulated air/gas(s) can be, without limitation, located in one or more of any suitable and effective location(s). The one or more said means to move and/or circulate the said air/gas(s), such as, but not limited to any effective blower(s), air pump(s), and/or fan(s), out of the said treatment chamber(s) and through the dehumidifier chamber(s) and/or droplet chamber(s), can also be, without limitation, located in one or more of any suitable and effective location(s). Without being limited, one or more outlet(s) of the one or more air blower(s) can be, without limitation, coupled to at least one diffuser(s). One or more of any suitable and effective air/gas(s) diffuser(s) are preferably, and without limitation, effectively located in a bottom of the treatment chamber(s) and/or space. It is preferred, without limitation, that the said one or more air/gas(s) outlet(s) and any associated diffuser(s) is effectively designed and constructed, in a manner known to those skilled in the art, so that the air/gas(s) that exit the said diffuser(s) can effectively spread along and/or around the bottom of the said sealed treatment chamber(s) and help dry various surfaces within the sealed treatment chamber(s) such as, but not limited to any, bottom and/or floor surface(s), ceiling(s), and/or wall surface(s).

Also, without being limited, the said air/gas(s) that is flowed by the said one or more blower(s), that is preferably and effectively heated to any effective temperature(s), blowing upward from the diffuser(s) contributes to effectively drying the treated and/or otherwise decontaminated object(s), device(s), and part(s), where these same object(s), device(s), and part(s) can be effectively, diagnosed, tested, function tested, monitored, diagnosed, qualified, analyzed, reported on, and/or assured in the same treatment chamber(s). Without being limited, the air/gas(s) from the said diffuser(s) can also pass through the treatment chamber(s) and through the at least one of any effective dehumidifier screen(s), or screen(s) that cover the one or more inlet(s) into the said one or more dehumidifier chamber(s), and the at least one of any effective droplet screen(s), or screen(s) that cover the one or more inlet(s) into the said one or more droplet chamber(s), can be located at one or more of any effective location(s) within the treatment chamber(s). It is preferred, without limitation, that the said one or more dehumidifier screen(s) and droplet screen(s), are effectively located at, about, and/or near the top of the inside of the sealed treatment chamber(s).

Without being limited, the air/gas(s) within the treatment chamber(s) can travel through the said dehumidifier screen(s) and into the one or more dehumidifier chamber(s), and also travels through the said droplet screen(s) and into the one or more droplet chamber(s). Also without being limited, the said heated air can also be circulated and/or recirculated from, to, and/or through, the treatment chamber(s) and into and/or through the said rear dehumidifier chamber(s) and the said rear droplet chamber(s), and preferably, and without limitation, back into the treatment chamber(s).

Without being limited, the filtered and/or heated air that enters the treatment chamber(s), can leave the treatment chamber(s) through one or more of any effective means such as, but not limited to the one or more suitable and effective vacuum pump(s) and/or through one or more of any suitable and effective exhaust vent(s) (not shown), that can be open and closed with one or more of any suitable valve(s) (not shown). It is preferred, without limitation, that the said vacuum pump(s) and/or exhaust valve(s) are not operated and/or opened, to exhaust the said heated and/or filtered air that is supplied to the treatment chamber(s), until, and/or effectively about when, the said filtered and/or heated air is flowed and/or started to flow, into the treatment chamber(s). Without being limited, the vacuum pump(s) can also be operated at any suitable and effective time(s) to dry the various surface(s) inside of the said treatment chamber(s) including but not limited to the various object surface(s). In addition, and without limitation, the filtered and/or heated air/gas(s) can be flowed into, through, and/or out of, the treatment chamber(s) at any suitable and effective time(s) to dry the various surface(s) inside of the said treatment chamber(s) including but not limited to the various object surface(s).

Without being limited, at least one treatment agent(s) reservoir(s) and/or water reservoir(s) are preferably, and without limitation, located in the top equipment space, but can also be located in any other suitable location(s). Without being limited, any suitable and effective treatment agent liquid(s), and preferably and without limitation, at least any effective, sanitizer(s), disinfectant(s), and/or sterilizing agent(s), and even more preferably and without any limitation, any effective cold steriliant(s), flows from its holding reservoir(s) and preferably, and without limitation, into a first inlet of one or more any suitable and effective mixing device(s) known to those skilled in the art, and water from the water reservoir(s) flows into a second inlet of the said mixing device(s). Without being limited, an output of the mixing device(s), if used, is connected to the supply reservoir(s) of the aerosol generator(s) and/or one or more of any other decontamination system(s) that may be used. Without being limited, the treatment agent(s) liquid(s) reservoir(s) and the water reservoir(s) may be filled through one or more of any suitable and effective fill port(s) and/or receptacles that are known to those skilled in the art, and are preferably and without limitation, dedicated to receive each type of the various liquid(s) that are used to replenish the multi-function treatment cabinet(s) and/or chamber(s) product apparatus, and are preferably and without limitation, effectively located outside the multi-function treatment cabinet(s) and/or chamber(s) product. Without being limited, the multi-function treatment cabinet(s) and/or chamber(s) product apparatus, can also be cartridge fed with one or more of any suitable cartridge(s), that can hold and feed at any suitable and effective time(s), the various liquid(s), water(s), agent(s), gas(s), and/or treatment agent(s), to the various said decontamination system(s).

Without being limited, inlets in at least one drain manifold(s) draw liquid from various location(s) within the sealed treatment cabinet(s) and at least one outlet feeds and/or routes the various captured waste liquid(s) into at least one liquid collection bottle(s). The liquid collection bottle(s) is preferably, and without limitation, removed from a front of the sealed treatment cabinet. The agent(s) control module(s) includes any of the suitable and effective electronic devices and software needed to control the operation of the various part(s) and apparatus(s) such as, but not limited to any, fan(s), blower(s), pump(s), heater(s), and operation(s), of the one or more decontamination system(s), aerosol generator(s), gas generator(s), air/gas(s) heater(s), dehumidifier(s), liquid heater(s), fan(s), blower(s), and can also communicate with the various test equipment(s). Without being limited, the wireless control interface preferably controls various operation(s) of the multi-function treatment cabinet(s) and/or chamber(s) product, such as, but not limited to, the operation of the one or more decontamination system(s) and/or agent(s) control module(s), however it can also, without limitation, control the operation of the various part(s) and apparatus(s) such as, but not limited to any, fan(s), blower(s), pump(s), heater(s), and operation(s), of the one or more decontamination system(s), aerosol generator(s), gas generator(s), air/gas(s) heater(s), dehumidifier(s), liquid heater(s), fan(s), blower(s), and can also communicate with the various test equipment(s). Without being limited, the wireless control interface can also communicate through or with at least one touch screen interface. Also without being limited, the wireless control interface can include wireless communication through various software and/or protocols known to those skilled in the art, such as, but not limited to any, Bluetooth, and WIFI, protocols and software.

One or more function testing device(s) that can be used for diagnosing, testing, function testing, monitoring, diagnosing, qualifying, analyzing, reported on, and/or assuring, the one or more of any treated, equipment(s), device(s), object(s), and/or medical device(s), such as, but not limited to any, ECG device(s), SPO2 device(s), temperature sensing device(s), TOCO device(s), patient monitoring device(s), can also be effectively located within the sealed treatment chamber(s), and can include, without limitation, at least one, test equipment(s), test module(s), and/or electronic test module(s), at least one suitable and effective test socket(s), at least one interface test block(s), and at least one bar code reader(s) and/or RFID reader(s). The test module(s) and/or electronic test module(s) can include, without limitation, any suitable, testing software, compliance software, tracking software, software to inventory tested electrical cables or components, and/or software to report testing compliance for any object(s) and/or device(s), connected to the one or more of any suitable and effective test socket(s). Without being limited, one or more of any suitable device(s) used to read any, bar code(s), radio frequency identification tag(s), or any other electronically imbedded coding circuit(s) (Herein called "Bar Code Reader" or "Reader"), can be used to identify the various treated object(s) such as, but not limited to any, device(s), tool(s), equipment(s), sensor(s), and/or electrical cable(s) or component(s), placed into the sealed treatment chamber(s). Without being limited, the output of the bar code reader(s) can be connected to the one or more test module(s) and/or electronic test module(s).

The one or more of any suitable and effective interface test blocks can include, but is not limited to one or more of any suitable and effective: ECG interface test block(s), SPO2 interface test block(s), IBP interface test block(s), a TEMP interface test block(s) and/or TOCO interface test block(s). Each interface test block preferably, and without limitation, can include a base portion and an extension portion, which extends from the base portion. When needed, and without limitation, the interface test block can also include at least one suitable and effective patient simulation device(s) for providing any suitable and effective, feedback(s), data(s), signal(s), simulated data(s), and/or stimulus(s), that would be known to those skilled in the art, to a sensor of a particular medical device and/or its one or more cable(s). At least one or a plurality of connector pin(s) can, and without limitation, extend from a back of the base portion(s). The connector pin(s) can be plugged into one of the at least one or plurality of test socket(s) that can be suitably and effectively located within the sealed treatment chamber(s).

Without being limited, one end of one or more of any, electrical cable(s), data cable(s), communication cable(s), and/or cable communication plug(s) and/or socket(s), that connects to any object(s) such as, but not limited to any, sensor(s) and/or medical device(s), is plugged into one or more of any suitable base socket(s) that connects and communicates with the one or more base portion(s), and an opposing end of the said electrical cable(s), data cable(s), tool(s)l communication cable(s), device(s), medical device(s), sensor(s), and/or cable communication plug(s) and/or socket(s), is connected to one or more of any suitable and effective extension socket(s) and/or one or more of any suitable and effective patient simulation device(s) and/or connection(s) for providing any suitable and effective, feedback(s), data(s), signal(s), simulated data(s), and/or stimulus(s), that would be known to those skilled in the art, for any suitable and effective, diagnosing, testing, function testing, monitoring, diagnosing, qualifying, validating, analyzing, reported on, and/or assuring, of the one or more of any tested object(s), device(s), tool(s), medical device(s), and/or sensor(s). Without being limited, the one or more of any, extension socket(s) and/or patient simulation device(s) and/or connection(s), can suitably and effectively connect with and/or communicate with the one or more extension portion(s). Without being limited, the one or more base portion(s) can have one or more of any suitable and effective base socket(s) type(s) and/or design(s).

Without being limited, the one or more interface test block(s) can also be permanently mounted in the sealed treatment chamber(s). However, it is preferred, without limitation, that the one or more interface test block(s) are effectively and releasably, held by, mounted into, connected with, the one or more of any suitable and effective test sockets, with which the interface test block(s) can connect and/or interface with, inside of the sealed treatment chamber(s).

Without being limited, the one or more interface test block(s) and the one or more test socket(s) can be designed in a manner known to those skilled in the art, so that they can have any suitable and effective friction fit(s) when interfaced, and/or there are one or more of any suitable and effective connector(s) and/or releasable anchor(s) and/or restraint(s), incorporated into the design(s) of the interface test block(s) and/or the test socket(s), all in a manner known to those skilled in the art, that can keep the interface test block(s) effectively interfaced with the test socket(s), until it is desired or necessary to remove the interface test block(s) from the test socket(s).

Without being limited, the present invention teaches the effective location and use of one or more of any suitable and effective, connection(s), connector(s), plug(s), socket(s), test socket(s), test plug(s), base socket(s), extension socket(s), signal simulator(s) interface(s), information simulator(s) interface(s), and/or patient simulation device(s) and/or their connection(s), within the one or more sealed treatment chamber(s), to accommodate, utilize, and enable, the effective communication of one or more of any suitable and effective, equipment(s), device(s), hardware(s), and/or software(s), for the diagnosing, testing, function testing, monitoring, diagnosing, qualifying, validating, analyzing, reported on, and/or assuring, of any, object(s), tool(s), sensor(s), medical device(s), dental device(s), and/or veterinary device(s), that may be encountered in various industries and/or markets such as, but not limited to any, healthcare setting(s), hospital(s), industrial area(s), life science area(s), veterinary office(s), and/or dentist office(s), that may be located in the treatment chamber(s).

Also without being limited, the present invention teaches the flexibility that is offered by using various interface test block designs and test socket designs, that are preferably, but not limited to, designed and constructed for the installation of the various test block(s) within, and removal from, the sealed treatment chamber(s), depending on and/or to accommodate, the various, object(s), tool(s), and/or device(s) that are treated and tested within the sealed treatment chamber(s). Without being limited, the said test block(s) are also designed and constructed to incorporate, possess, utilize, and communicate with, one or more of any suitable and effective, plug(s), socket(s), test socket(s), test plug(s), base socket(s), extension socket(s), signal simulator(s) interface(s), information simulator(s) interface(s), and/or patient simulation device(s) and/or their connection(s), to accommodate, utilize, and enable, the effective communication of one or more of any suitable and effective, equipment(s), device(s), hardware(s), and/or software(s), for the diagnosing, testing, function testing, monitoring, diagnosing, qualifying, validating, analyzing, reported on, and/or assuring, of any, object(s), tool(s), sensor(s), medical device(s), dental device(s), and/or veterinary device(s), that may be encountered in various industries and/or markets such as, but not limited to any, healthcare setting(s), hospital(s), industrial area(s), life science area(s), veterinary office(s), and/or dentist office(s), and that may be interfaced with the said test block(s). Without being limited, the said one or more test block(s) can be located in one or more of any suitable and effective location(s) within the sealed treatment chamber(s), including at any suitable and effective distance(s) from any wall(s) and/or chamber floor(s). Also, it is preferred, without limitation, that the various test block(s) and any of the different types of connection(s), connector(s), plug(s), socket(s), test socket(s), test plug(s), base socket(s), extension socket(s), signal simulator(s) interface(s), information simulator(s) interface(s), and/or patient simulation device(s) and/or their connection(s), that are incorporated into their design, are designed and constructed so that any and/or various surfaces of the treated and/or tested object(s) are not shadowed by touching any surface(s), except for any surfaces such as, but not limited to any surfaces of any interfaced, plug(s), connector(s), socket(s), and/or sensor(s) surface(s) that are tested.

For example, and without limitation, it is advantageous for hospitals to decontaminate and then test various, instrument(s), sensor(s), imaging device(s), and/or medical device(s), requiring many different types of connection(s), connector(s), plug(s), socket(s), test socket(s), test plug(s), base socket(s), extension socket(s), signal simulator(s) interface(s), information simulator(s) interface(s), and/or patient simulation device(s) and/or their connection(s). Without limitation, the location, placement, and use, of various configured test block(s) within the sealed treatment chamber(s), especially, and without limitation, the removable test block(s), gives hospitals the flexibility to both decontaminate, process, dry, and test various instrument(s), sensor(s), imaging device(s), and/or medical device(s), and their various interfaces, without having to purchase multiple different and/or specifically tailored sealed treatment chamber(s) product(s) for the decontamination and testing of various object(s) and/or any multi-function treatment cabinet(s) and/or chamber(s) product(s), to decontaminate, process, dry, and test, specific instrument(s), sensor(s), imaging device(s), and/or medical device(s).

It is preferred, without limitation, that the said various, object(s), tool(s), sensor(s), medical device(s), dental device(s), and/or veterinary device(s), are diagnosed, tested, function tested, monitored, diagnosed, qualified, validated, analyzed, reported on, and/or assured, after they are decontaminated, sanitized, disinfected, high-level disinfected, and/or sterilized.

Without being limited, the various test equipment(s) such as, but not limited to any, electrical function tester(s) can also test the safety of various cable(s) such as, but not limited to any electrical cable(s). Without limitation, the test module and/or electronic test module can be located in one or more of any suitable and effective locations such as, but not limited to, in the top equipment space of the the multi-function treatment cabinet(s) and/or chamber(s) product apparatus.

Without being limited, the one or more of any sealed treatment chamber(s) can also be any suitable and effective chamber(s) and/or enclosure(s) known to those skilled in the art, that can effectively communicate with one or more any suitable and effective decontamination system(s) known to those skilled in the art, that effectively clean, decontaminate, sanitize, disinfect, high-level disinfect, and/or sterilize the various surface(s), located within the said sealed treatment chamber(s). Also, and without being limited, the said sealed treatment enclosure(s) can also effectively communicate with one or more of any suitable and effective means, part(s), component(s), apparatus(s), device(s) and/or design(s), known to those skilled in the art, to effectively dry the various surfaces within the treatment chamber(s), and/or remove any, particle(s), humidity(s), water vapor(s), vapor(s), and/or unwanted or undesired gas(s), from within the said treatment chamber(s) at one or more of any suitable and effective time(s) during the various processing step(s) to effectively treat, process, and/or dry, the various surface(s) of the one or more of any treated object(s) within the sealed treatment chamber(s).

Without being limited, the present invention also includes and describes one or more of any suitable and effective means for treating, decontaminating, sanitizing, disinfecting, high-level disinfecting, sterilizing, and/or drying, the various surface(s) of various object(s) within one or more of any suitable and effective, chamber(s), enclosure(s), and/or treatment chamber(s), where the said one or more object(s) is effectively and releasably held and/or supported by one or more of any suitable and effective object(s) support(s) and/or holder(s)(Herein called "Rotating Object(s) Holder(s)"), and where any effective, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), and/or also the opposite motion and/or movement to this, passes the one or more object(s) from the one or more of any suitable and effective first support(s), member(s), and/or holder(s), to the one or more of any suitable and effective second support(s), member(s), and/or holder(s), and the any effective reverse, reverse direction, opposite, reflecting, returning, backward, and/or opposite, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), and/or also the opposite motion and/or movement to this, passes the one or more object(s) from the one or more of any suitable and effective second support(s), member(s), and/or holder(s), back to the one or more of any suitable and effective first support(s), member(s), and/or holder(s), where the said one or more object(s) can be moved back and forth between the first and second support(s), member(s), and/or holder(s), one or more times, before, during, and/or after, one or more of any suitable and effective activity(s) such as, but not limited to any, treating, sanitizing, disinfecting, sterilizing, decontaminating, and/or drying, of any surface(s) within any treatment chamber(s), including any surface(s) of the said one or more object(s) and/or rotating object(s) holder(s).

Without being limited, one or more of any rotating object(s) holder(s) can be effectively located and operated in one or more of any suitable and effective, sealed treatment chamber(s), enclosure(s), chamber(s), and/or cabinet(s), that preferably, and without limitation, are designed and constructed using any suitable and effective design(s) and/or construction(s) known to those skilled in the art.

In addition, and without limitation, the rotating object(s) holder(s) can be combined and/or operated with one or more of any suitable and effective system(s) and/or technology(s), known to those skilled in the art, that can decontaminate, sanitize, disinfect, high-level disinfect, sterilize, and/or dry, the various surface(s) within the said sealed treatment chamber(s), and/or any other effective, enclosure(s), chamber(s), and/or cabinet(s), and preferably, and without limitation, effectively all of the various surfaces exposed at one or more of any time(s) within the said treatment chamber(s), and more preferably, and without limitation, all of the various surface(s) of the one or more treated object(s) that are held by the rotating object(s) holder(s) within the treatment chamber(s), and even more preferably, and without limitation, all of the various surface(s) within the said treatment chamber(s) that are exposed to the atmosphere(s) within the treatment chamber(s), at one or more of any time(s) and/or during any of the one or more processing step(s) and/or operation(s), and/or one or more of any effective actuation(s) and/or movement(s) of the said rotating object(s) holder(s) and/or means to hold and/or support the object(s).

Without being limited, it is also apparent that a need exits in the current art to to effectively process, decontaminate, sanitize, disinfect, high-level disinfect, sterilize, and/or dry, one or more of various objects such as, but not limited to any, hose(s), cord(s) endoscope(s), cable(s), and/or wire(s), as well as any hose(s), tube(s), conduit(s), cable(s), and/or wire(s) that are detached, directly attached, and/or indirectly attached, to and/or from, various instrument(s), tool(s), sensor(s), device(s), imaging device(s), and/or medical device(s), used in various industries such as, but not limited to any, life sciences, medical, dental, pharmaceutical, clean room, and/or veterinary medicine. Also, and without being limited, at least one FDA approved medical device(s) known to those skilled in the art, can disinfect and/or high-level disinfect, but does not have sterilize claims for various ultrasound probe(s) and/or topical imaging apparatus(s), and typically their handle(s), cord(s), and/or cable(s) as well, but the said at least one medical device(s) are not constructed and/or designed to sanitize, disinfect, high-level disinfect, and/or sterilize, the various cable(s) and/or wire(s) that extend from the said various ultrasound probe(s) and topical imaging apparatus(s), and/or their handle(s), and they instead protrude outside of the sealed treatment chamber while the said connected ultrasound probe(s) and topical imaging apparatus(s) are treated and processed inside the said treatment chamber. Without being limited, these various cable(s) and/or wire(s) that extend outside of the said sealed treatment chamber(s) have been identified as potential vectors of infectious disease(s) and/or hospital borne infections for patients, and therefore a need is present to effectively, high-level disinfect and/or sterilize, not only the various medical device(s), such as but not limited to any imaging apparatus(s), and their handle(s) if present, but also one or more of any attached wire(s), hose(s), and/or cable(s), and/or their one or more of any connector(s). Without limitation, a need is also present to effectively, sanitize, disinfect, high-level disinfect, sterilize, and/or dry, various hose(s), wire(s), cable(s), conduit(s), and/or endoscope(s). Without being limited, the length, long length, dimensions, width, diameter, abnormal length, and/or excessive length, of these various said object(s), hose(s), cable(s), wire(s), device(s), medical device(s), and/or any attached cord(s), wire(s), cable(s), and/or hoses, is also known to those skilled in the art to be a barrier to their effective processing, decontamination, sanitization, disinfection, high-level disinfection, sterilization, and/or drying, especially with respect to avoiding any shadowed surface(s) that can result from their being held and/or supported in any treatment chamber(s).

The present invention provides, and without limitation, an effective means to support and/or hold, and also effectively, decontaminate, sanitize, disinfect, high-level disinfect, sterilize, and/or dry, the various exposed surface(s) of the one or more of any suitable, object(s), hose(s), tube(s), cable(s), wire(s), endoscope(s), device(s), imaging device(s), scope(s), medical device(s), and/or any one or more of any attached and/or detached, cord(s), wire(s), cable(s), hoses, as well as any other associated and exposed surface(s) of any, connector(s), plug(s), and/or socket(s). Without being limited, shadowed surface(s) that could result from the said treated object(s) resting on one or more of any of the said member(s) and/or support(s) within the treatment chamber(s) are eliminated by moving the treated object(s) back and forth from one or more first member(s) and/or support(s) to one or more second member(s) and/or support(s), during various steps of the processing of the said object(s) including, but not limited to any effective, decontamination, sanitization, disinfection, high-level disinfection, sterilization, and/or drying, steps. Without being limited, these said various steps can be taken while the said treated object(s) are being held by and/or resting on the one or more first said member(s) and/or support(s) and/or the one or more second said member(s) and/or support(s).

Without being limited, the present invention also improves the means to hold and/or support the various one or more object(s) that are located within the treatment chamber(s) for one or more of any suitable and effective, decontamination, sanitization, disinfection, high-level disinfection, sterilization, and/or drying, steps. Without being limited, the one or more of the said object(s) that are processed, can be initially releasably interfaced with one or more of any suitable and effective first means to hold and support the said one or more object(s) (Herein called "First Holding Means"), and later releasably interfaced with any suitable and effective second means to hold and support the said one or more object(s) (Herein called "Second Holding Means"). It is preferred, without limitation, that the said first and second holding means are designed and constructed so that they can both effectively release and/or move the said one or more object(s) to one another, and later also effectively receive the said one or more object(s) from one another, at one or more of any suitable and effective time(s).

The various means to hold and/or support the said one or more object(s) in the treatment chamber(s) were tested with various, shapes, sizes, dimensions, and designs. Without being limited, the one or more means to hold and/or support the said one or more object(s) in the treatment chamber(s) can be any suitable and effective, size(s), shape(s), dimension(s), texture(s), lubricity(s), coefficient of friction(s), geometry(s), design(s), and/or material(s) of construction. Without being limited, it was determined, and without limitation, that using any effectively sized and shaped "V" shape, for the holding and/or supporting means, and/or holding member(s) and/or support(s), was most effective. It is preferred, without limitation, that the said holding member(s) and/or support(s) are constructed from at least any suitable passivated and polished 316 stainless steel. Also, without being limited, the said "V" shaped holding and/or supporting means offers various advantages such as, but not limited to: first, and without limitation, the "V" shaped holding and/or supporting means and its various dimensions, can create an effective friction fit with the one or more surface(s) of the various sized object(s) with which this "V" shaped holding and/or supporting means releasably interfaces with; second, and without limitation, the "V" shaped holding and/or supporting means can be effectively scaled to any suitable and effective size(s) to effectively accommodate and interface with various sized object(s), third, and without limitation, the "V" shaped holding and/or supporting means can effectively accommodate various object(s) with any suitable and effective, size(s), dimension(s), geometry(s), and/or shape(s); fourth, and without limitation, the mass of the one or more said object(s) that is interfaced with the "V" shaped holding and/or supporting means, combined with the "V" shaped support(s) and/or member(s), can create an effective friction fit between the said object(s) and the said "V" shaped holding and/or supporting means. Further, and without being limited, gravity and the mass and weight of the processed object(s) and/or the object(s) to be processed, in direct conjunction with the architecture of the "V" shaped object support(s) and/or member(s), combine to ensure a tight fit on or with the object(s) and the "V" shaped object support(s) and/or member(s) they interface with and/or with the object(s) and the various support(s) and/or member(s) that support and/or hold the object(s).

Without being limited, the holding and/or supporting means, and/or holding member(s) and/or support(s), can also be configured and/or constructed in any other suitable and effective shape(s) and/or geometries, such as, but not limited to any, "U" shape. It is preferred, without limitation that the one or more of any suitable, object(s), wire(s), device(s), cable(s), hose(s), and/or endoscope(s), that are interfaced with the holding and/or supporting means are at least suitably and effectively sized and shaped, and more preferably, and without limitation, they have about a circular cross section that has any suitable and effective diameter(s). Without being limited, the one or more of any holding and/or supporting means, and/or holding member(s) and/or support(s), can be constructed from one or more suitable and effective member(s), support(s), beam(s), and/or rod(s).

The present invention describes, and without limitation, a one or more rotating and/or effectively moving, object(s) holder(s), for use in preferably, and without limitation, a multi-function treatment cabinet(s) and/or chamber(s) product, but at least any suitable and effective, treatment chamber(s) and/or enclosure(s), that is preferably, and without limitation, resealable, and that preferably includes a rotating cable tube(s) and/or rod(s), a mounting bracket, a motor with gear reduction, a motor controller and two snap switches. The rotating cable tube(s) and/or rod(s) preferably, and without limitation, includes a tubular rod, a first mounting rod, a second mounting rod, a first plurality of any suitably and effectively shaped supports and/or member(s), and more preferably and without limitation, any suitable and effective, V-shaped members, and a second plurality of any suitably and effectively shaped supports and/or member(s), and more preferably and without limitation, any suitable and effective, V-shaped members. A bottom of the first plurality of V-shaped members are preferably, and without limitation, welded to a first mounting rod. The first mounting rod is preferably, and without limitation, welded to the tubular rod. A bottom of the second plurality of V-shaped members are preferably, and without limitation, welded to a second mounting rod. The second mounting rod is preferably, and without limitation, welded to the tubular rod, such that the first plurality of V-shaped members are located 180 degrees or opposite from the second plurality of V-shaped members. The mounting bracket includes a base member, a first leg, a second leg, a first switch plate and a second switch plate. The first leg extends outward from a first end of the base member and the second leg extends outward from a second end of the base member. The first switch plate extends outward from one side of the first leg and the second switch plate extends from an opposite side of the first leg.

The multi-function treatment cabinet(s) and/or chamber(s) product includes at least one effective treatment chamber(s) and/or sealed treatment chamber(s) (Herein called "Sealed Treatment Chamber(s)") that can be preferably, and without limitation, opened, closed, and effectively sealed. The sealed treatment chamber(s) includes opposing side walls, and an opposing ceiling and floor. The rotating cable tube(s) and/or rod(s) is rotationally retained on opposing side walls with a pair of flanged bearing blocks. Tube holes are formed through the opposing side walls to receive the tubular rod. The pair of flanged bearing blocks are preferably retained on outside surfaces of the opposing side walls. First and second snap switches are attached to the first and second switch plates. The motor with gear reduction is attached to the base member of the mounting bracket with fasteners. Without being limited, any suitable and effective motor, that preferably, and without limitation, also has any suitable and effective gear reduction, can be directly and/or indirectly interfaced with the tubular rod. An output shaft of the motor with gear reduction is inserted into an end of the tubular rod. A threaded hole is formed through an end of the tubular rod. A set screw is threaded into the threaded hole. The set screw is long enough to extend outward from an outer diameter of the rotating cable tube(s) and/or rod(s).

A clockwise DPDT relay and a counter clockwise DPDT relay are used to provide power to a motor of the motor with gear reduction. The motor controller includes two output terminals, which output a clockwise voltage and a counter clockwise voltage. The clockwise voltage is outputted for a first period of time and the counter clockwise voltage is outputted for a second period of time. The clockwise voltage is used to energize a clockwise solenoid of the clockwise DPDT relay, which closes a first contact to supply a positive terminal of the motor with the clockwise voltage and a second contact to provide a ground path for a ground terminal of the motor. The rotating cable tube(s) and/or rod(s) rotates, preferably and without limitation, in any suitable and effective, clockwise direction, until the setscrew forces the normally closed first snap switch to open. The opening of the first snap switch stops rotation of the rotating cable tube(s) and/or rod(s). After the first period of time is over, the motor controller outputs the counter clockwise voltage for a second period of time. The counter clockwise voltage is used to energize a counter clockwise solenoid of the counter clockwise DPDT relay, which closes a first contact to supply a negative terminal of the motor with counter clockwise voltage and a second contact to provide a ground path for a positive terminal of the motor. The rotating cable tube(s) and/or rod(s) rotates, preferably and without limitation, in any suitable and effective, counter clockwise direction, until the setscrew forces the normally closed second snap switch to open. The opening of the second snap switch stops rotation of the rotating cable tube(s) and/or rod(s). After the second period of time is over, the motor controller outputs the clockwise voltage for a new first period of time.

Without being limited, the said holding and/or supporting means, and/or holding member(s) and/or support(s), and preferably, and without limitation, the V-shaped members, can hold, support, and/or interface with, one or more of any suitable and effective object(s) such as, but not limited to any, device(s), medical device(s), cord(s), cable(s), wire(s), hose(s), conduit(s), endoscope(s), imaging device(s), ultrasonic probe(s), and/or topical ultrasonic imaging device(s). Also, without being limited, each ultrasonic probe and topical ultrasonic imaging device(s) can include, without limitation an ultrasonic imaging head, a handle, and a cord and/or cable. Typically, and without limitation, only the ultrasonic head and the handle of various ultrasonic probe(s) and topical ultrasonic imaging device(s) are decontaminated, disinfected, high-level disinfected, sterilized, and/or dried, in the various treatment chamber(s) currently used in the present art, which leaves the said cords and/or connector(s) untreated and potentially contaminated with one or more of any, virus(s), bacteria(s), spore(s), fungus(s), mold(s), and/or infectious bio-burden(s).

However, and without limitation, the rotating object holder(s) allows and/or provides for the entire ultrasonic probe(s) and topical ultrasonic imaging device(s), as well as any other suitable object(s) such as, but not limited to any, device(s), medical device(s) and any of their part(s), dental device(s) and any of their part(s), cord(s), cable(s), wire(s), hose(s), conduit(s), endoscope(s), and/or imaging device(s), to be effectively, decontaminated, sanitized, disinfected, high-level disinfected, sterilized, and/or dried, preferably, and without limitation, with an effective treatment and processing of all of the treated object(s) external surface(s) without any surface shadowing that would result in a failure to treat all of the targeted surfaces of the treated object(s).

Without being limited, various object(s) such as, but not limited to any, cord(s), cable(s), wire(s), hose(s), tube(s), conduit(s), patient monitoring device cable(s), medical device probe(s), topical imaging device(s), and/or endoscope(s), can be located and/or placed between two adjacent V-shaped members of the rotating cable tube(s) and/or rod(s). Without being limited, various device(s), equipment(s), imaging device(s), ultrasonic probe(s), topical ultrasonic imaging device(s), remote data sending and/or reporting device(s), medical device(s), dental device(s), and/or veterinary device(s), can also be attached to one or more of any object(s) such as, but not limited to any, cord(s), cable(s), wire(s), hose(s), tube(s), conduit(s). It is preferred, without limitation, that the said any, cord(s), cable(s), wire(s), hose(s), tube(s), conduit(s), and/or endoscope(s), are placed between two adjacent V-shaped members of the rotating cable tube(s) and/or rod(s), such that any effective length(s), and preferably and without limitation, a longer portion, of the said any, cord(s), cable(s), wire(s), hose(s), tube(s), conduit(s), and/or endoscope(s), extends any effective distance(s) and/or length(s) from one side of the V-shaped members, and any object(s) and/or device(s) such as, but not limited to any ultrasonic probe(s) and/or imaging device(s), and any effective length(s) of the said any, cord(s), cable(s), wire(s), hose(s), tube(s), conduit(s), and/or endoscope(s), extend any effective distance(s) and/or length(s) from an opposing side of the V-shaped members. Without being limited, one or more of any suitable object(s) can be interfaced with one or more of any effectively shaped member(s) and/or V-shaped members.

Without being limited, the cleaning, decontamination, sanitization, disinfection, high-level disinfection, sterilization, and/or drying, process(s) includes, and without limitation, one or more cleaning, decontamination, sanitization, disinfection, high-level disinfection, and/or sterilization period(s) and/or stage(s), when the one or more treated object(s) are treated with one or more of any effective treatment agent(s), and one or more drying period(s) and/or stage(s) where the deployed treatment agent(s) within the sealed treatment chamber(s) are dried, purged, and/or removed, from the various surfaces, object surface(s), air/gas(s), and/or atmosphere(s), within the sealed treatment chamber(s), and preferably, and without limitation, drying the various surface(s) of the treated object(s). Without being limited, the one or more rotating object(s) holder(s), and more particularly the one or more initial and/or primary one or more V-shaped member(s), that is suitably and effectively located within the sealed treatment chamber(s), is preferably, and without limitation, rotated, turned, moved, pivoted, and/or angled, any effective, direction(s), distance(s), degree(s), and/or angle(s), but preferably and without limitation, at least around and/or about 180 degrees, to effectively move the one or more held and/or supported object(s) to the at least second one or more adjacent V-shaped member(s), to expose one or more of any untreated area(s) and/or surface(s) of the one or more treated object(s) that was retained between the previous two adjacent V-shaped members, to the deployed treatment agent(s).

Without being limited, the one or more object(s) can be moved between, and/or back and forth between, the initial and/or primary V-shaped member(s) and the secondary V-shaped member(s), one or more time(s), to effectively expose the various surface(s) of the treated object(s) to the deployed treatment agent(s).

In addition, and without being limited, after the various and/or targeted surface(s) of the treated object(s) are effectively treated with the one or more treatment agent(s), the various surface(s) of the treated object(s) can be effectively dried and/or any of the deployed treatment agent(s) can be removed from various location(s) within the sealed treatment chamber(s) such as, but not limited to any, the various surface(s) of the treated object(s), the various surface(s) of the support and/or holding member(s) such as, but not limited to any V-shaped member(s), and/or the atmosphere(s) and/or air/gas(s) within the sealed treatment chamber(s) (Herein called "Drying Process(s))".

It is preferred, without limitation, that the various drying process(s) and/or any drying activities, for the one or more treated object(s), starts with the said treated object(s) being held and/or supported by the one or more initial and/or primary one or more V-shaped member(s), that is suitably and effectively located within the sealed treatment chamber(s).

It is also preferred, without limitation, that the said initial and/or primary one or more V-shaped member(s) are located at and/or effectively near any effective orientation(s) and/or angle(s), and more preferably and without limitation at or effectively near the 12:00 position and/or pointing effectively about up and/or toward the ceiling(s) of the sealed treatment chamber(s), when starting any step(s) and/or processes(s) to expose the various surface(s) of the object(s) and/or treated object(s) with the treatment agent(s), as well as any step(s) and/or processes(s) to dry the various treated object surface(s) and/or remove any treatment agent(s) from the various treated object surface(s).

Without being limited, when drying the various surface(s) of the one or more treated object(s), the one or more rotating object(s) holder(s), and more particularly the one or more initial and/or primary one or more V-shaped member(s), that is suitably and effectively located within the treatment chamber(s), is preferably, and without limitation, rotated, turned, moved, pivoted, and/or angled, any effective, distance(s), direction(s), degree(s), and/or angle(s), but preferably and without limitation, at least around and/or about 180 degrees, to effectively move the one or more held and/or supported object(s) to the at least second one or more adjacent V-shaped member(s), to expose the one or more of any object(s) surface(s) that are still, or may be, in contact with any treatment agent(s), and/or to expose the one or more of any undried area(s) and/or surface(s) of the object(s), that was retained between the previous two adjacent V-shaped members, to any, atmosphere(s), air/gas(s), heated air/gas(s), filtered and heated air/gas(s), that are flowed through the sealed treatment chamber(s) for various purposes including, but not limited to, removing the various deployed treatment agent(s) from the various surface(s) of the said treated object(s), effectively drying the various surface(s) of the said object(s), and/or removing the various deployed treatment agent(s) from the various surface(s) within the treatment chamber(s).

Without being limited, the one or more object(s) can be moved between the initial and/or primary V-shaped member(s) and the secondary V-shaped member(s) one or more time(s) to expose the various surface(s) of the object(s) and/or treated object(s) to the any, treatment agent(s), atmosphere(s), air/gas(s), heated air/gas(s), filtered and heated air/gas(s), that can be flowed into and/or through the sealed treatment chamber(s), for purposes including, but not limited to, effectively treating the various surface(s) of the treated object(s), effectively drying all and/or various surface(s) of the said object(s) located within the sealed treatment chamber(s). The various surface(s) of the said object(s) located inside the sealed treatment chamber(s) can be effectively treated and dried at any suitable and effective time(s) and for any suitable and effective duration of time(s).

Accordingly, it is an object of the present invention to provide a multi-function treatment cabinet(s) and/or chamber(s) product, which can provide any effective, decontamination, sanitization, disinfection, high-level disinfection, sterilization, and/or drying, that is all preferably and without limitation, conducted using any effective low temperature process(s) and/or technology(s), for various, object(s) such as, but not limited to any, device(s), tool(s), sensor(s), cable(s), wire(s), medical device(s), dental device(s), imaging device(s), endoscope(s), patient monitoring device(s), ultrasonic probe(s), computer mouse(s), hose(s), pipe(s), industrial device(s), and/or veterinary device(s).

It is another object of the present invention to provide a multi-function treatment cabinet(s) and/or chamber(s) product, that can diagnose, test, function test, monitor, diagnose, qualify, validate, analyze, reported on, and/or assure, various, object(s) such as, but not limited to any, device(s), tool(s), sensor(s), cable(s), wire(s), medical device(s), dental device(s), imaging device(s), endoscope(s), patient monitoring device(s), ultrasonic probe(s), computer mouse(s), hose(s), pipe(s), industrial device(s), and/or veterinary device(s), before, after, and/or during, they are cleaned, decontaminated, sanitized, disinfected, high-level disinfected, and/or sterilized.

It is still another object of the present invention to provide a multi-function treatment cabinet(s) and/or chamber(s) product, that can provide electrical, function, and/or safety testing of various, object(s) such as, but not limited to any, device(s), tool(s), sensor(s), cable(s), wire(s), medical device(s), dental device(s), imaging device(s), endoscope(s), patient monitoring device(s), ultrasonic probe(s), computer mouse(s), hose(s), pipe(s), industrial device(s), and/or veterinary device(s), after they are cleaned, decontaminated, sanitized, disinfected, high-level disinfected, and/or sterilized.

It is still even another object of the present invention to provide a multi-function treatment cabinet(s) and/or chamber(s) product, that can have one or more test block(s), that are preferably and without limitation, removable, and effectively located inside of the sealed treatment chamber(s), and can be used to diagnose, test, function test, monitor, diagnose, qualify, validate, analyze, reported on, and/or assure, various, object(s) such as, but not limited to any, device(s), tool(s), sensor(s), cable(s), wire(s), medical device(s), dental device(s), imaging device(s), endoscope(s), patient monitoring device(s), ultrasonic probe(s), computer mouse(s), hose(s), pipe(s), industrial device(s), and/or veterinary device(s), before, after, and/or during, they are cleaned, decontaminated, sanitized, disinfected, high-level disinfected, and/or sterilized.

It is another object of the present invention to provide a rotating, turning, pivoting, and/or effectively moving, object(s) holder and treatment apparatus for a multi-function treatment cabinet(s) and/or chamber(s) product, which treats and/or dries the entire surface area(s) of one or more of any object(s) such as, but not limited to any, device(s), tool(s), sensor(s), cable(s), wire(s), medical device(s), dental device(s), imaging device(s), ultrasonic probe(s), topical ultrasonic imaging device(s), endoscope(s), patient monitoring device(s), ultrasonic probe(s), computer mouse(s), hose(s), pipe(s), industrial device(s), and/or veterinary device(s).

It is still another object of the present invention to provide the means for and to record various data and/or information related to the treated object(s) such as, but not limited to any, unique identity(s) or identifier(s), inventory information(s), the date(s) and time(s) the object(s) is treated and processed, the result(s) and/or status(s) of any testing the object(s) have undergone, the result(s) and/or status(s) of any surface treatment(s) and/or decontamination cycle(s) that were undertaken for the object(s), and also where this information can be printed at any suitable location(s) and also communicated and/or reported via any network(s) and/or any wireless means, to one or more of any location(s) for any suitable uses.

These and additional objects, advantages, features and benefits of the present invention will become apparent from the following specification.

DETAILED DESCRIPTION OF THE PREFERRED EMBODIMENTS

Figure 1:
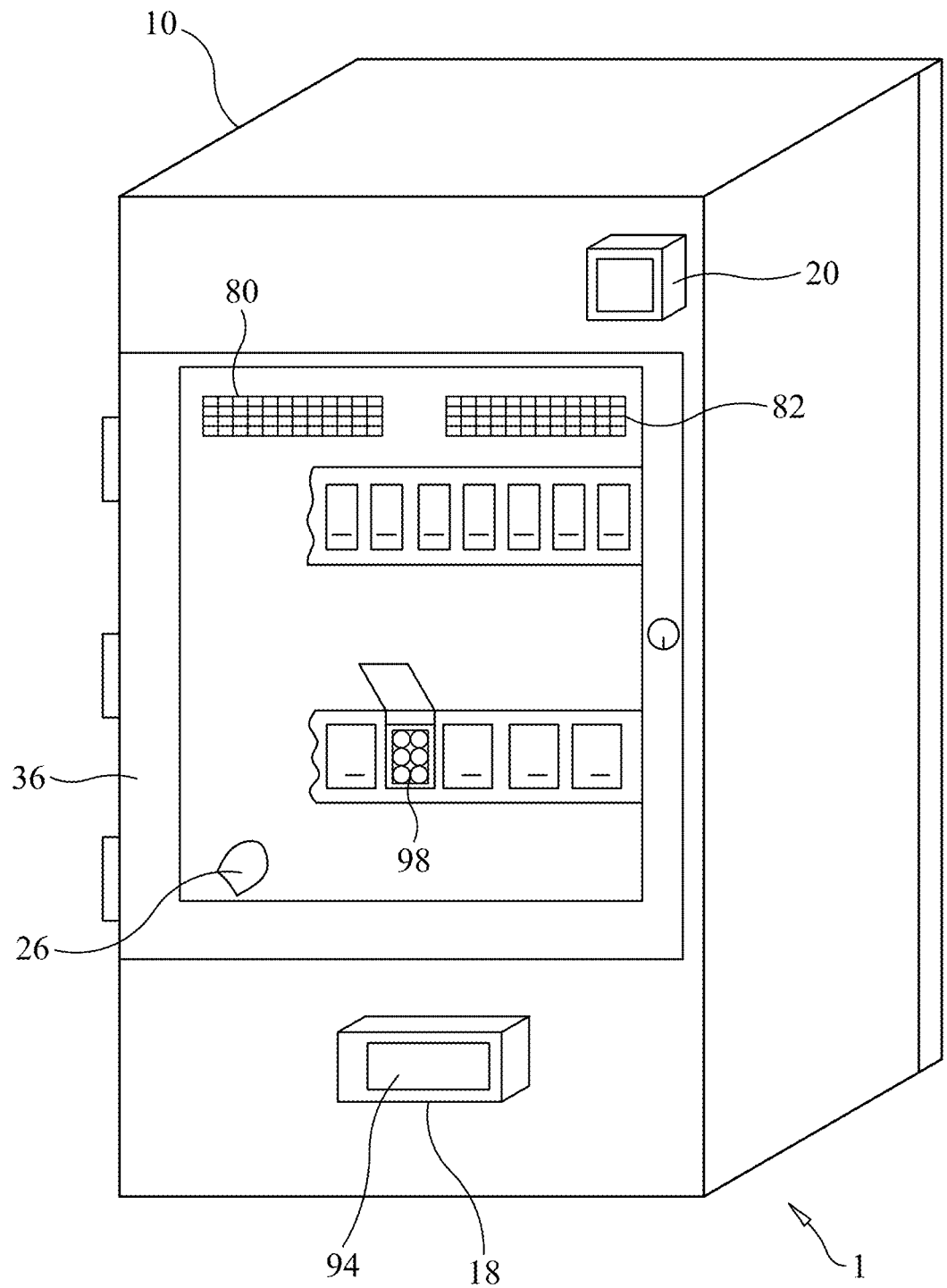
FIG. 1 is a perspective view of a multi-function product disinfection cabinet in accordance with the present invention.
Figure 2:
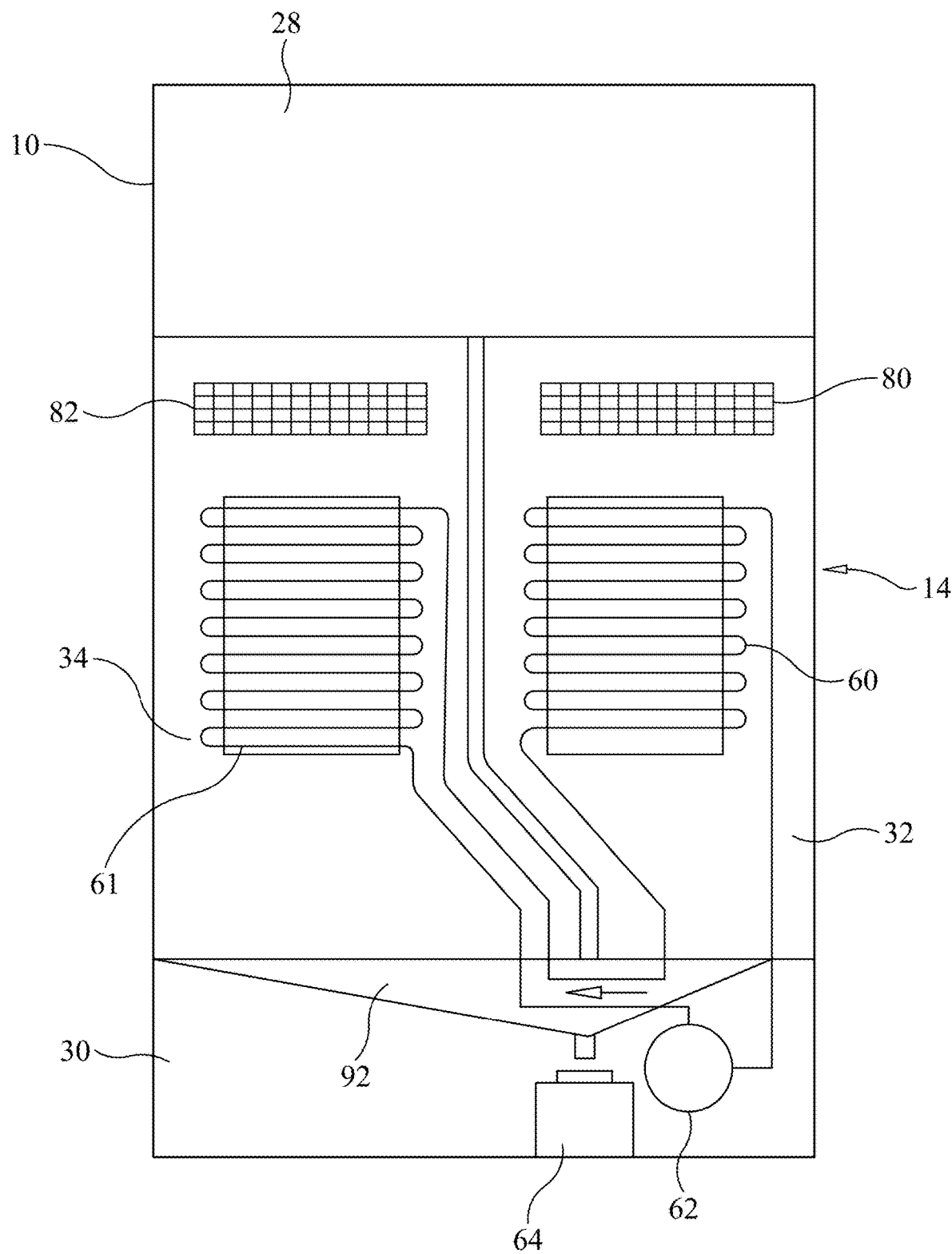
FIG. 2 is a rear view of a multi-function product disinfection cabinet with a rear panel removed to reveal a rear dehumidifier chamber and a rear droplet chamber in accordance with the present invention.
Figure 3:
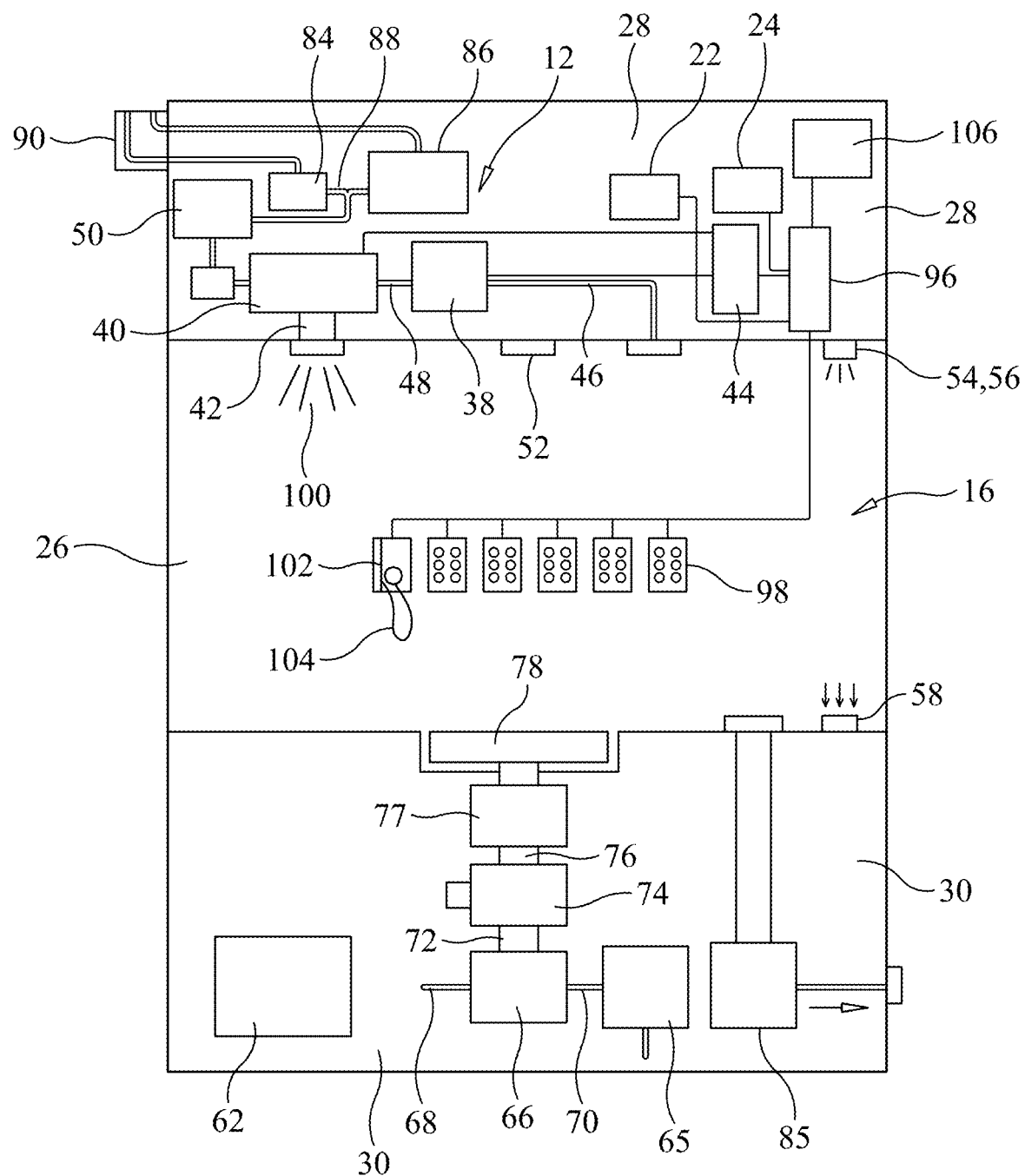
FIG. 3 is a schematic diagram of a portion of a multi-function product disinfection cabinet in accordance with the present invention.
Figure 4:
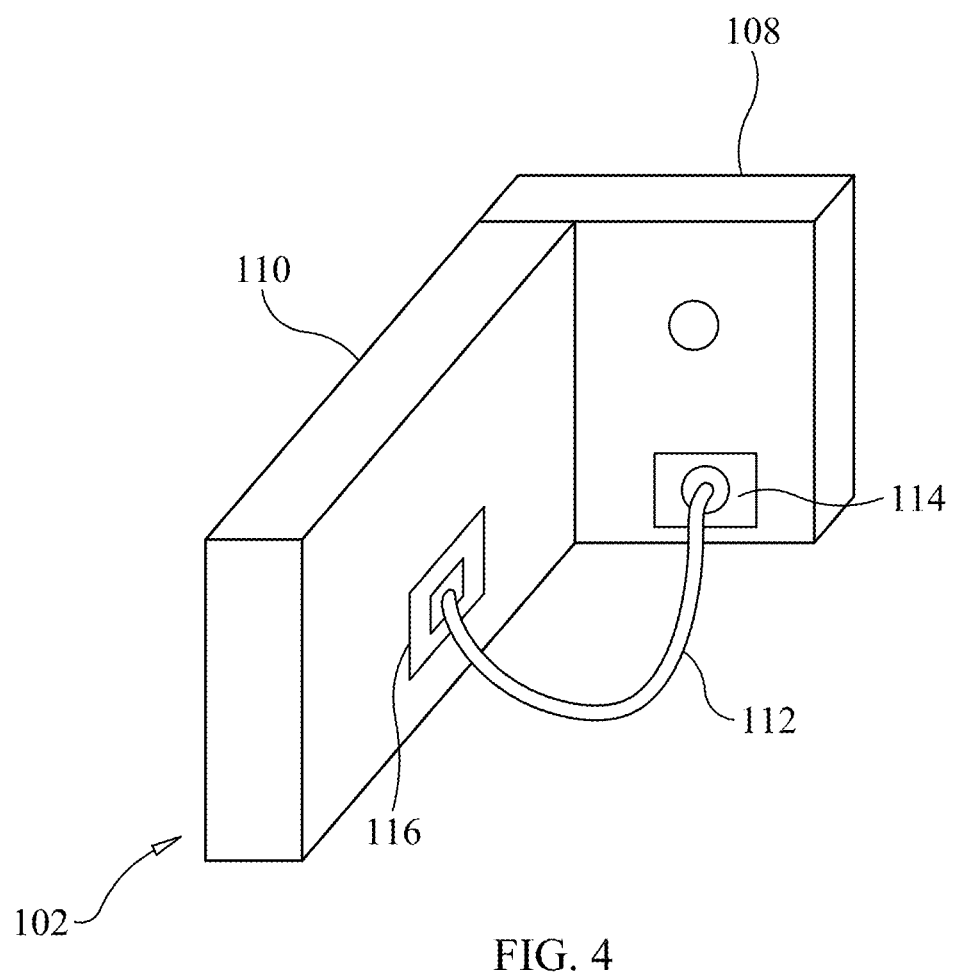
FIG. 4 is a perspective view of an interface test block with a cable inserted for testing in accordance with the present invention.

With reference now to the drawings, and particularly to FIG. 1, there is shown a perspective view of a Multi-function Treatment Cabinet(s) and/or Chamber(s) Product 1. With reference to FIGS. 2-4, and without limitation, the Multi-function Treatment Cabinet(s) and/or Chamber(s) Product 1 preferably includes at least one resealable and/or treatment enclosure(s) and/or cabinet(s) 10, at least one system(s) for any suitable and effective, decontamination, sanitization, disinfection, high-level disinfection, and/or sterilization, (Herein called "Decontamination System(s)") 12, at least one of any suitable and effective dehumidification system(s) 14, at least one of any suitable and effective, function testing device(s) 16, at least one of any suitable and effective, wireless control interface(s) 18, at least one of any suitable and effective, bar code reader(s) 20, at least one of any suitable and effective, compliance reporting software(s) 22 and tracking software(s) 24.

Without being limited, any object(s) (300) such as, but not limited to any, equipment(s), device(s), accessory(s), tool(s), cord(s), tube(s), pipe(s), hose(s), tube(s), conduit(s), cable(s), wire(s), umbilical connection(s), scope(s), endoscope(s), ultrasonic probe(s), medical device(s), dental device(s) veterinary device(s), industrial device(s), tool(s) and device(s) for the life sciences industries, ultrasonic device(s), ultrasonic probe(s), imaging device(s), topical imaging device(s), temperature reading device(s), blood pressure monitoring and/or measuring device(s), oxygen monitoring and/or measuring device(s), cutting tool(s), irrigation device(s), suction and/or vacuum device(s), drilling device(s), and/or patient monitoring equipment, including, but not limited to, any of their part(s), accessories, and/or component(s), can be suitably and effectively located within one or more of any suitable and effective, cabinet(s), enclosure(s), chamber(s), sealed chamber(s), sealed enclosure(s), resealable chamber(s), resealable treatment chamber(s), resealable treatment enclosure(s), sealed treatment chamber(s), and/or treatment enclosure(s) (Herein called "Treatment Chamber(s)") 26, and be effectively, treated, decontaminated, sanitized, disinfected, high-level disinfected, sterilized, and/or dried.

Without being limited, the at least one sealed treatment cabinet(s) 10 preferably, and without limitation, includes at least one of any suitable and effective sealed treatment chamber(s) 26 that can be effectively, unsealed opened, closed, and resealed, at least one top equipment space(s) 28, at least one bottom equipment space(s) 30, at least one of any suitable and effective rear dehumidifier chamber(s) 32, at least one of any suitable and effective rear droplet chamber(s) 34 and at least one of any suitable sealed door(s) 36 that can be, opened, closed, and resealed, at any suitable and effective time(s).

The at least one of any suitable and effective decontamination system(s) 12 that can provide and/or produce any suitable and effective, decontamination, sanitization, disinfection, high-level disinfection, and/or sterilization, of the various surfaces and one or more of any treated object(s) (300) surface(s), within the sealed treatment chamber(s) 26, preferably, and without limitation, can include at least one airborne agent(s) blower(s) 38, at least one of any suitable and effective, aerosol(s) generator(s), vapor(s) generator(s), light system(s), and/or gas(s) generator(s), and/or otherwise any suitable and effective decontamination system(s) (Herein called "Decontamination System(s)") 40, known to those skilled in the art, aerosol(s) and/or gas(s) tubing 42, and at least one control module(s) (Herein called "Agent Control Module(s)") 44, for controlling the various function(s) and/or operation(s) of the Multi-function Treatment Cabinet(s) and/or Chamber(s) Product 1, such as, but not limited to the one or more, and/or any combination(s) of, the said any effective, aerosol(s) generator(s), vapor(s) generator(s), gas(s) generator(s), and/or decontamination system(s) 40. It is preferred, without limitation that the one or more decontamination system(s) 40, are at least one or more of any suitable and effective ultrasonic aerosol generator(s). Patent no. 9551996 to Baumgartner et al. describes the elements of the preferred, but not limited to, decontamination system(s) 40 that is a preferred, without limitation, example of any effective aerosol generator(s) 40 that can preferably, and without limitation, be used in the present invention, and is herein incorporated by reference in its entirety. One or more inlet(s) 46 of the one or more airborne agent(s) blower(s) 38 communicates with the one or more of any suitable and effective, sealed treatment chamber(s) 26 and one or more outlet(s) 48 of the one or more of any suitable and effective, airborne agent(s) blower(s) 38 that can, without limitation, move and/or flow any, suitable and effective quantity(s) of any, air, gas(s), aerosol(s), and/or vapor(s), at any suitable and effective time(s) and for any suitable and effective duration(s) of time(s), is connected to at least one outlet(s) of one or more of any suitable and effective decontamination system(s) 40, and more preferably, and without limitation, one or more of any suitable and effective, decontamination system(s) 40 that are any effective aerosol generator(s). The said airborne agent(s) blower(s) 38 blows air/gas(s) into the one or more inlet(s) of the aerosol generator(s) and/or decontamination system(s) 40 and assists in drawing, flowing, and/or moving the generated treatment agent(s) 100, and more preferably and without limitation any generated aerosol(s) 100, out of the the aerosol generator(s) and/or decontamination system(s) 40 and into the sealed treatment chamber(s) 26. Without being limited, any suitable and effective treatment agent(s) 100 can be deployed into the sealed treatment chamber(s) 26, to treat, decontaminate, sanitize, disinfect, high-level disinfect, and/or sterilize, the various surfaces within the sealed treatment chamber(s) 26, but is preferred without limitation, that the treatment agent(s) 100 are any suitable and effective aerosol(s), and more preferred, without limitation that the treatment agent(s) 100 are any aerosol(s) with a size that is at least less than ten micron, and even more preferred, without limitation, that the treatment agent(s) 100 are any aerosol(s) with an average size less than one micron, and very preferred, without limitation, that the treatment agent(s) 100 are any aerosol(s) with an average size less than 0.7 micron.

At least one inlet(s) of the aerosol tubing 42 is connected to at least one outlet(s) of the said aerosol generator(s) and/or decontamination system(s) 40 and at least one outlet(s) of the at least one aerosol tubing(s) 42 communicates with the at least one sealed treatment chamber(s) 26. The agent control module(s) 44 can control the operation of the various components of any suitable and effective decontamination system(s) 12. The decontamination system(s) 12 can be located in any suitable and effective location(s), preferably located in the top equipment space 28, but can also, and without limitation, be located at any suitable and effective location(s) next to, approximate to, behind, and/or under, the sealed treatment chamber(s) 26.

Without being limited, one or more of any suitable and effective light(s) 52 can be effectively interfaced with and/or communicate with, the interior of the sealed treatment chamber(s) 26. Without being limited, the light(s) 52 can shine into the sealed treatment chamber(s) 26 at any suitable and effective time(s). Without limitation, the light(s) 52 can shine into the said sealed treatment chamber(s) 26 and preferably, and without limitation, illuminate certain types of the various treatment agent(s) 100 that can be present in the sealed treatment chamber(s) 26. Also, and without being limited, the light 52 that is shined and/or emitted into the sealed treatment chamber(s) 26 can be one or more of any suitable and effective color(s), and one or more of any color(s) of light can be shined into the sealed treatment chamber(s) 26 at any time(s) before, during, and/or after, any, part(s) of, various step(s) of, and/or process(es) of any, treatment, drying, and/or processing, of the various surface(s) within the sealed treatment chamber(s) 26, including, but not limited to, the various surface(s) of the one or more object(s) (300).

It is preferred, without limitation, that at least a blue, and/or green, colored light(s) 52, or at least one light(s) 52 that is close to these shade(s) of light(s), is shined and/or emitted into the sealed treatment chamber(s) 26 for various situations such as, but not limited to, at least when the Multi-function Treatment Cabinet(s) and/or Chamber(s) Product 1 is ready to begin any treatment and/or processing cycle(s), the Multi-function Treatment Cabinet(s) and/or Chamber(s) Product 1 is in any sleeping state(s) or dormant mode(s), and/or all of the treatment cycle(s) is complete and/or the entire processing cycle has ended or is complete.

It is also preferred, without limitation, that at least a red, yellow, and/or orange, colored light(s) 52, or at least one light(s) 52 that is close to these shade(s) of light(s), is shined and/or emitted into the sealed treatment chamber(s) 26 when the treatment agent(s) 100 are deployed into and/or present inside of the sealed treatment chamber(s) 26. It is also preferred, without limitation, that when there is any error with any operation of the Multi-function Treatment Cabinet(s) and/or Chamber(s) Product 1 at any time, that the said light(s) 52 will start to strobe or blink on or off, preferably, and without limitation, with any, red, yellow, and/or orange, color(s).

Without limitation, one or more of any suitable and effective, light source(s) 56, first light sensor(s) 54, and second light sensor(s) 58, can be suitably and effectively located at one or more of any suitable and effective location(s) within, interfaced effectively with, and/or communicating effectively with, the one or more of any sealed treatment chamber(s) 26, for purposes such as, but not limited to, detecting the presence of, detecting the absence of, detecting the presence of an efficacious quantity of, and/or detecting the absence of an efficacious quantity of, the one or more of any treatment agent(s) 100, within the sealed treatment chamber(s) 26, all in a manner known to those skilled in the art.

Without being limited, the said one or more, light source(s) 56, first light sensor(s) 54, and second light sensor(s) 58, can be operated and used in any suitable and effective manner(s) as taught in a previous United States patent application by Ricciardi et al., as well as any effective manner(s) known to those skilled in the art. Without being limited, light is emitted from the one or more suitable and effective light source(s) 56, and received by either and/or both the at least one first light sensor(s) 54 and the at least one second light sensor(s) 58.

Without being limited, any effective, type(s), color(s), amount(s), power(s), and/or intensity(s), of any light(s), can be emitted from the at least one light source(s) 56, and received by the at least one first light sensor(s) 54 and/or second light sensor(s) 58.

Without being limited, any effective, amount(s), concentration(s), and/or quantity(s), of the treatment agent(s) 100, within the sealed treatment chamber 26, such as, but not limited to any, vapor(s), gas(s), UV light(s), surface treatment light(s), and/or aerosol(s) 100, and preferably and without limitation, any effective aerosol(s) 100, and more preferably and without limitation, any effective aerosol(s) 100 that are generated by any effective ultrasonic aerosol generating system(s), can be detected, indicated by, and/or reported by, the one or more second light sensor(s) 58, by first detecting and/or sensing various condition(s), such as, but not limited to any, effective decreased amount(s) of light(s), effective decreased intensity(s) of light(s), effective decreased power(s) of light(s), light frequency(s), and/or effective change(s) in the detected light(s) frequency(s), from any light(s) emitted by the at least one light source(s) 56. It is preferred, without limitation, that the said deployed agent(s) 100 blocks the light(s) emitted from the said light source(s) 56 and prevents the emitted light(s) from reaching the said second light sensor(s) 58.

Also, without being limited, any effective, amount(s), concentration(s), and/or quantity(s), of the treatment agent(s) 100, within the sealed treatment chamber(s) 26, such as, but not limited to any, vapor(s), gas(s), UV light(s), surface treatment light(s), and/or aerosol(s) 100, and preferably and without limitation, any effective aerosol(s) 100, and more preferably and without limitation, any effective aerosol(s) 100 that are generated by any effective ultrasonic aerosol generating system(s), can be detected by, indicated by, and/or reported by, the one or more first light sensor(s) 54, by first detecting and/or sensing various condition(s), such as, but not limited to any, reflected light(s) off the deployed treatment agent(s) 100, effective increased amount of reflected light(s) off the deployed treatment agent(s) 100, effective increased intensity(s) of reflected light(s) off the deployed treatment agent(s) 100, effective increased power(s) of reflected light(s) off the deployed treatment agent(s) 100, light frequency(s), and/or effective change(s) in the detected light(s) frequency(s), from the light(s) emitted by the at least one light source(s) 56.

Without being limited, the one or more of any suitable and effective, light source(s) 56, first light sensor(s) 54, and second light sensor(s) 58, can be suitably and effectively located in any suitable and effective direction(s) and/or orientation(s) within the sealed treatment chamber(s) 26. For example, and without limitation, it is preferred, without limitation, that the one or more light source(s) 56 and the one or more second light sensor(s) 58 is located horizontally (not shown), and preferably and without limitation, effectively opposed to one another, at one or more of any effective location(s) and/or distance(s) from any floor(s) and/or bottom surface(s) within the sealed treatment chamber(s) 26. It is also preferred, without limitation, that at least one or more light source(s) 56 and first light sensor(s) 54, are suitably and effectively located in and/or affixed to, one or more of any wall(s) and/or ceiling(s) surface(s) within the sealed treatment chamber(s) 26.

Also, and without being limited, any effective type(s) and amount(s) of light(s), can be emitted from the at least one light source(s) 56 and received by the at least one first light sensor(s) 54, if there is a presence of certain treatment agent(s) and/or there is a sufficient and/or effective amount(s) and/or quantity(s) of certain treatment agent(s) 100, within the sealed treatment chamber(s) 26, such as, but not limited to any aerosol(s) 100, and more preferably and without limitation, any effective aerosol(s) 100 that are generated with any effective, ultrasonic aerosol generating system(s), aerosol generator(s), and/or decontamination system(s) 40.

Without being limited, the one or more light source(s) 56, first light sensor(s) 54, and second light sensor(s) 58, can effectively communicate with and/or be controlled by, the one or more of any suitable, wireless control interface(s) 18 and/or agent(s) control module(s) 44.

Without being limited, one or more of any suitable and effective dehumidification system(s) and/or vapor removal system(s), known to those skilled in the art, can be used in the present invention. Without being limited, the one or more dehumidifier(s) 14 preferably includes at least one evaporator coil(s) 60, at least one condenser coil(s) 61 and at least one air conditioning compressor(s) 62. At least one outlet(s) of the air conditioning compressor(s) 62 is connected to at least one inlet(s) of the said at least one evaporator coil(s) 60. At least one outlet(s) of the one or more evaporator coil(s) 60 is connected to at least one inlet(s) of the at least one condenser coil(s) 61. One or more outlet(s) of the condenser coil(s) 61 is connected to one or more inlet(s) of the one or more air conditioner compressor(s) 62. The one or more air conditioner compressor(s) 62 pumps refrigerant through the one or more evaporator coil(s) 60 and the one or more condenser coil(s) 61. The one or more evaporator coil(s) 60 is effectively located inside the at least one dehumidifier chamber(s) 32. The at least one condenser coil(s) is effectively located in the at least one droplet chamber(s) 34. The one or more air conditioning compressor(s) 62 can be preferably, and without limitation, located inside the bottom equipment space 30. Moisture and/or any other gas(es) and/or vapor(s) in the air/gas(s) flowed from inside of the sealed treatment chamber(s) 26, condenses on the one or more evaporator coil(s) 60 and then drops into at least one liquid collection bottle(s) 64. The evaporator coil(s) 60 and the condenser coil(s) 61 can be constructed from any suitable and effective materials, but is preferred, without limitation, that they are at least constructed from any FDA approved stainless steel such as, but not limited to any suitable and effective 316 stainless steel. Heat from the one or more condenser coil(s) 61 can heat and/or dry the air/gas(s) that pass and/or are flowed through the one or more droplet chamber(s). One or more of any suitable and effective filtration unit(s) 65 receives air/gas(s) from the droplet chamber(s) 34. Without being limited, the air/gas(s) from the droplet chamber(s) 34 can pass through the one or more filtration unit(s) 65 and is suitably and effectively filtered for any, gas(s), vapor(s), and/or particle(s), all in a manner known to those skilled in the art. Without being limited, the air/gas(s) that flow through the dehumidifier chamber(s) 32 can also be suitably and effectively filtered by one or more of any suitable and effective filter(s) (not shown), all in a manner known to those skilled in the art.

Without being limited, at least one of any suitable and effective diverter valve(s) 66 is preferably located in the bottom equipment chamber 28. The said one or more diverter valve(s) 66 includes at least one humidifier chamber inlet(s) 68, at least one droplet chamber inlet(s) 70 and at least one outlet(s) 72. Without being limited, the said diverter valve(s) 66 can shuttle between the one or more humidifier chamber inlet(s) 68 and the one or more droplet chamber inlet(s) 70. The said one or more outlet(s) 72 of the diverter valve(s) 66 is connected to one or more inlet(s) of one or more suitable and effective air/gas(s) blower(s) 74. At least one outlet(s) 76 of the at least one air/gas(s) blower(s) 74 is connected to at least one suitable and effective heater(s) 77. The said one or more heater(s) 77 is any suitable and effective heater(s) that can effectively heat any air/gas(s) that enters the sealed treatment chamber(s) 26, to any suitable and effective temperature(s). The one or more heater(s) 77 is effectively connected to one or more of any suitable and effective diffuser(s) 78. The at least one diffuser(s) 78 is preferably, and without limitation, suitably and effectively located in a bottom of the sealed treatment chamber(s) 26. Without being limited, air/gas(s) that are preferably, but without limitation, blowing upward from the said diffuser(s) 78 can effectively dry and/or effectively remove, any and/or all of the deployed treatment agent(s) 100 from the various surface(s) from the one or more treated object(s) (300) located within the sealed treatment chamber(s) 26. Without being limited, the air/gas(s) from the one or more diffuser(s) 78 can pass through at least one dehumidifier(s) screen(s) 80 and/or the at least one droplet screen(s) 82 within the sealed treatment chamber(s) 26, but preferably and without limitation, suitably and effectively near a top of the at least one sealed treatment chamber(s) 26. The air/gas(s) from within the sealed treatment chamber(s) 26 can travel through the at least one humidifier screen(s) 80 and into the one or more dehumidifier chamber(s) 32 and/or into the one or more droplet screen(s) 82 and into the one or more droplet chamber(s) 34. Without being limited, the said screen material can be any suitable and effective, screen, grate, and/or entry guard, material(s), component(s), part(s), and/or substrate(s), known to those skilled in the art.

Without being limited, the various surface(s) within the one or more of any location(s) such as, but not limited to, the sealed treatment chamber(s) 26, can be effectively dried at one or more of any suitable and effective time(s), before, during, and/or after, the various surface(s) within the sealed treatment chamber(s) 26, including but not limited to any surface(s) of the one or more object(s) 300, are decontaminated, sanitized, disinfected, high-level disinfected, and/or sterilized. It is preferred, without limitation, that the various surface(s) within the sealed treatment chamber(s) 26, including but not limited to, the various surface(s) of the one or more object(s) 300 located within the sealed treatment chamber(s) 26, are effectively dried at least after they are decontaminated, sanitized, disinfected, high-level disinfected, and/or sterilized, but it is more preferred, without limitation, that the various surface(s) within the sealed treatment chamber(s) 26, including but not limited to, the various surface(s) of the one or more object(s) 300 located within the sealed treatment chamber(s) 26, are effectively dried before they are decontaminated, sanitized, disinfected, high-level disinfected, and/or sterilized, and/or after they are decontaminated, sanitized, disinfected, high-level disinfected, and/or sterilized. Without being limited, the various surface(s) within the dehumidifier chamber(s) 32 and/or the droplet chamber(s) 34, can also be effectively dried at one or more of any suitable and effective time(s), by flowing the air/gas(s), that is preferably, and without limitation, effectively heated, from within the sealed treatment chamber(s) 26, through these location(s) one or more time(s).

Without being limited, one or more of any suitable and effective process(s), technology(s), and/or apparatus(s), known to those skilled in the art, can be used to effectively dry the various surface(s) and/or object(s) 300 surface(s) located within the sealed treatment chamber(s) 26 at any suitable and effective time(s).

In a first example, and without limitation, one or more of any suitable and effective flows of air/gas(s) that are effectively heated, with one or more of any suitable and effective means known to those skilled in the art, such as, but not limited to, one or more of any suitable and effective heater(s) 77, to any suitable and effective temperature(s), can be moved and/or flowed through location(s) such as, but not limited to, the said sealed treatment chamber(s) 26.

In a second example, and without limitation, any one or more flows of air/gas(s) that are sourced from outside of the Multi-function Treatment Cabinet(s) and/or Chamber(s) Product 1, and are effectively, filtered and/or heated, with any suitable and effective means known to those skilled in the art, such as, but not limited to, one or more of any suitable and effective heater(s) 77 and filter(s) (not shown in this particular application), to any suitable and effective temperature(s), can be moved and/or flowed through location(s) such as, but not limited to, the said sealed treatment chamber(s) 26, and then effectively moved, flowed, and/or exhausted from and/or out of the Multi-function Treatment Cabinet(s) and/or Chamber(s) Product 1. Without being limited, at least one suitable and effective vacuum pump(s) 85, can also be used to move and/or flow the said air/gas(s), fresh air/gas(s), and/or heated air/gas(s), through and/or out of, the said sealed treatment chamber(s) 26.

It is preferred, without limitation, that at least one suitable and effective vacuum pump(s) 85 is preferably used to pull any effective vacuum(s) and/or create one or more of any effective negative pressure(s) and/or vacuum(s) on and/or within the said sealed treatment chamber(s) 26, at one or more effective time(s), but preferably and without limitation, before, and more preferably and without limitation, before and/or after, the various object(s) 300 are decontaminated, sanitized, disinfected, high-level disinfected, and/or sterilized, to effectively dry the various surface(s) within the sealed treatment chamber(s) 26, including but not limited to any and/or all, of the one or more surface(s) of the object(s) 300 located within the sealed treatment chamber(s) 26, as well as various other surface(s) located at any and/or all location(s) within the sealed treatment chamber(s) 26.

Without being limited, at least one of any suitable and effective conduit(s) (not shown) that communicate with and are controlled by one or more of any suitable and effective valve(s) (not shown) can effectively connect the interior space(s), chamber area(s), and/or the interior atmosphere(s), of the sealed treatment chamber(s) 26, with any environment(s) and/or atmosphere(s) outside of the the sealed treatment chamber(s) 26, and more preferably and without limitation, outside of the Multi-function Treatment Cabinet(s) and/or Chamber(s) Product 1, and provide at least one suitable and effective source(s) of air/gas(s) and/or fresh and air/gas(s), that can be flowed and/or moved into and/or through the sealed treatment chamber(s) 26. Without being limited, this said flow of air/gas(s) and/or fresh air/gas(s) can be effectively filtered. Also, and without being limited, this said flow of air/gas(s) and/or fresh air/gas(s) can also be effectively heated at one or more of any suitable and effective time(s), to any suitable and effective temperature(s).

Without being limited, the said flow of air/gas(s) and/or fresh air/gas(s), sourced from outside of the the sealed treatment chamber(s) 26, and more preferably and without limitation, from the environment and/or atmosphere outside of the the Multi-function Treatment Cabinet(s) and/or Chamber(s) Product 1, can be flowed and/or moved into and/or through the sealed treatment chamber(s) 26 at one or more of any suitable and effective time(s) and for any suitable and effective duration(s) of time(s), including, but not limited to, for purposes including, but not limited to, effectively cooling the various and/or all surface(s) within the sealed treatment chamber(s) 26, to any effective temperature(s), including the various and/or all surface(s) of the one or more object(s) 300 located within the sealed treatment chamber(s) 26, and more preferably, and without limitation, after the various surface(s) within the sealed treatment chamber(s) 26 have been treated and/or processed by any heated air/gas(s) flows that have been circulated and/or moved into and/or through, the one or more location(s) such as, but not limited to any, sealed treatment chamber(s) 26, dehumidifier chamber(s) 32, and/or droplet chamber(s) 34. Without being limited, the various said surface(s) within the dehumidifier chamber(s) 32, droplet chamber(s) 34, and/or sealed treatment chamber(s) 26, including, but not limited to the various, wall surface(s), equipment surface(s), and object(s) 300 surface(s), can be heated and/or cooled to one or more of any effective temperature(s).

Without being limited, any air/gas(s) that are flowed and/or moved into the sealed treatment chamber(s) 26 and/or any one or more part(s) of any system of any part(s), component(s), area(s), and/or space(s), that connect and/or communicate with the sealed treatment chamber(s) 26, for one or more of any effective time(s) and for any effective duration of time(s), can be effectively filtered, as well as effectively heated to one or more of any effective temperature(s) with one more more of any suitable and effective heater(s). Also without being limited, the at least one suitable and effective heater(s) 77 that can be used to effectively heat any air/gas(s) to any one or more effective temperature(s), that are flowed, moved, and/or circulated, within and/or through the sealed treatment chamber(s) 26, can also be used to remove any additional moisture and/or deployed treatment agent(s) within the sealed treatment chamber(s) 26, that are, and without limitation, not effectively removed by the said vacuum pump(s) 85.

Without being limited, at least one reservoir(s) 84 to hold the one or more of any suitable and effective treatment agent(s), and at least one water reservoir(s) 86 (if needed and/or used), are preferably, and without limitation, located in the top equipment space 28. Without being limited, one or more of any suitable and effective treatment agent(s), such as, but not limited to any, peroxyacetic acid (PAA) in aqueous form, flows from the treatment agent(s) reservoir(s) 84 and into a first at least one inlet(s) of at least one suitable and effective mixing device(s) 88 (if needed and/or used) and water from the water reservoir 86 flows into a second one or more inlet(s) of the mixing device(s) 88. Also, and without being limited, one or more outlet(s) of the mixing device(s) 88 is connected to the supply reservoir 50 (if needed and/or used) of the aerosol generator(s) and/or decontamination system(s) 40. The at least one treatment agent(s) reservoir(s) 84 and the at least one water reservoir(s) 86 can be, and without limitation, filled through at least one fill port(s) 90 suitably located outside of and/or external to, the one or more sealed test cabinet(s) 10. Without being limited, the at least one of any aerosol generator(s) and/or decontamination system(s) 40 can also be directly and/or indirectly fed with one or more suitable and effective cartridge(s), all in a manner known to those skilled in the art.

Without being limited, one or more of any suitable and effective inlets (not shown) in at least one suitable drain manifold(s) 92 can draw and/or receive liquid(s) from at least one suitable and effective location(s) within locations such as, but not limited to any, dehumidifier chamber(s) 32, droplet chamber(s) 34, and/or sealed treatment chamber(s) 26, and at least one outlet(s) can feed and/or direct the said liquid(s) into one or more suitable liquid collection bottle(s) 64. The one or more liquid collection bottle(s) 64 is preferably removed from a front of the sealed test cabinet(s) 10.

Without being limited, the one or more agent(s) control module(s) 44 can include, and without limitation, the various electronic device(s), system(s), hardware(s), and/or software(s), known to those skilled in the art, that is needed to control and/or communicate with various operation(s) and function(s) of the various part(s), component(s), hardware(s), equipment(s), device(s), and/or software(s), of the Multi-function Treatment Cabinet(s) and/or Chamber(s) Product 1, such as, but not limited to any, decontamination system(s) 12, dehumidification system(s) 14, air/gas(s) movement system(s), air/gas(s) flow control valve(s), and/or air/gas(s) heating system(s), and can also, and without limitation, communicate with one or more of any, test equipment(s) 16 and test module(s) 96. It is preferred, without limitation, that the test equipment(s) 16 communicates with the test module(s) 96, which can also communicate with the agent(s) control module(s) 44.

Also, without being limited, one or more of any suitable wireless control interface(s) 18 can preferably, and without limitation, control the operation of the agent(s) control module(s) 44 through one or more of any suitable and effective touch screen interface(s) 94. The agent(s) control module(s) 44 preferably, and without limitation, controls the test module(s) 96.

Without being limited, the one or more wireless control interface(s) 18 can include, without limitation, one or more of any suitable and effective, wireless communication(s), in addition to any suitable and effective software(s), hardware(s), transceiver(s), and device(s), including, but not limited to any suitable and effective, bluetooth and WI-FI related software and any related programming and hardware(s).

Also, and without being limited, the various test equipment(s) 16 preferably and without limitation, includes one or more of any suitable and effective, test module(s) 96, test socket(s) 98, interface test block(s) 102, and bar code reader(s) 20. Without being limited, the one or more test module(s) 96 can include, without limitation, any suitable and effective, testing software, quality assurance software, inventory software, inventory reporting software, diagnostic software, compliance software 22, tracking software 24, and software to inventory and/or report any processed and/or tested object(s) 300.

Without being limited, one or more object(s) 300, can be effectively interfaced with and/or retained in or with, the one or more interface test block(s) 102. Without being limited, the said one or more interface test block(s) 102 are suitably and effectively located in the sealed treatment chamber(s). Without being limited, the interface test blocks 102 can be permanently electrically connected to the one or more test module(s) 96 without the need for the one or more test sockets 98. However, it is preferred, without limitation, that the one or more interface test blocks 102 are effectively and removably interfaced with the one or more test sockets 98 that are suitably and effectively located within the sealed treatment chamber(s) 26.

Also, without being limited, the one or more bar code reader(s) 20 can perform one or more of any suitable and effective function(s) and/or action(s) such as, but not limited to, read, scan, receive, translate, communicate with, and/or report, any, bar code(s), data symbol(s), radio frequency identification tag(s) and/or device(s) (RFID), and/or any other electronically imbedded coding circuit(s) and/or device(s) known to those skilled in the art, (Herein after called "Bar Code(s)" (not shown)).

Without being limited, the various bar code(s) can be used to identify one or more of any object(s) 300 that is located within the sealed treatment chamber(s) 26. Any data, outputs, signals, and/or communications, from the one or more bar code reader(s) 20 can, without limitation, effectively communicate with the test module(s) 96, agent control module(s) 44, wireless control interface(s) 18, and/or any other directly and/or indirectly connected and/or remote, apparatus(s), computer(s), networked computer(s), processor(s), network(s), workstation(s), computer networks(s), server(s), software(s), and/or data base(s), all in a manner known to those skilled in the art.

Without being limited, the bar code(s) can relay, transmit, and/or represent, any suitable and effective data(s) and information(s) to any bar code reader(s) 20 and one or more of any directly and/or indirectly connected and/or remote, apparatus(s), computer(s), networked computer(s), processor(s), network(s), workstation(s), computer networks(s), server(s), software(s), data base(s), and/or the multi-function treatment chamber(s) and/or cabinet(s) product(s), about the treated object(s) 300 such as, but not limited to any, unique identity(s) or identifier(s), age of the object(s), number of testing cycle(s) the object(s) has undergone, number of decontamination cycles the object(s) has undergone, the last time the object(s) has been tested by a metrology department, the last time the object(s) has been tested, serial number(s), and/or inventory information(s).

Without being limited, once read by the bar code reader(s) 20, the bar code(s) information can be used, and/or combined with any other suitable information or data, to report one or more of any suitable information or report(s) to one or more of the said any, directly and/or indirectly connected and/or remote, apparatus(s), computer(s), workstation(s), networked computer(s), processor(s), network(s), computer network(s), server(s), software(s), data base(s), and/or the multi-function treatment chamber(s) and/or cabinet(s) product, such as, but not limited to any, the name and/or serial number of the multi-function treatment chamber(s) and/or cabinet(s) product that was operated, the person(s) or robot(s) who operated the multi-function treatment chamber(s) and/or cabinet(s) product, date(s) and time(s) the object(s) is located within the treatment chamber(s), date(s) and time(s) the object(s) is treated and/or processed, result(s) and/or status(s) of any surface treatment(s) and/or decontamination cycle(s) that were undertaken for the object(s), whether the surface treatment(s) and/or decontamination cycle(s) that were undertaken for the object(s) was successful or not, any error(s) that were encountered during any decontamination, treatment, and/or testing, activity(s) and/or process(s), result(s) and/or status(s) of any testing the object(s) have undergone, and/or the date(s) and time(s) the object(s) is removed from the treatment chamber(s).

Without being limited, this information can be communicated and/or reported via any, wired connection(s), network(s), and/or wireless means, to any of the said location(s), all in a manner known to those skilled in the art. It is preferred, without limitation, that this said data and information is also available via one or more of any printout(s) from one or more of any suitable printer(s) known to those skilled in the art, preferably, and without limitation, suitably located on the exterior of the multi-function treatment chamber(s) and/or cabinet(s) product.

The one or more interface test block(s) 102 can include, without limitation, one or more of any suitable and effective, test equipment(s), test device(s), test apparatus(s), data output(s) and/or input(s), signal output(s) and/or input(s), sensor(s), monitoring device(s), simulation device(s), and/or patient simulation device(s) for providing any suitable and effective, feedback(s), data(s), signal(s), power, simulated data(s), and/or stimulus(s), that would be known to those skilled in the art, to any, part(s), apparatus(s), sensor(s) and/or device(s), of any particular medical device(s) and/or one or more of its, cable(s), wire(s), plug(s), and/or socket(s).

Without being limited, the one or more interface test block(s) 102 can also include, but is not limited to, one or more of any suitable and effective, ECG interface test block(s), SPO2 interface test block(s), IBP interface test block(s), a'TEMP interface test block(s) and/or TOCO interface test block(s).

With reference to FIG. 4, and without being limited, each of the one or more interface test block(s) 102 preferably, and without limitation, includes at least one base portion(s) 108, and at least one extension portion(s) 110. Without being limited, the at least one extension portion(s) 110 can extend any suitable and effective distance(s) from the base portion 108, and can be any suitable and effective, length, width, height, shape, and/or geometry. It is preferred, without limitation, that any of the one or more plug(s), socket(s), and/or object(s) interface(s), that connect and/or interface with any one or more part(s) and/or location(s) of the said test block(s) 102, are suitably and effectively located, and more preferably and without limitation, so that none of the surfaces of the treated and tested object(s) 300 are covered and/or shadowed by any interfacing surface(s), except, and without being limited, any surfaces of the object(s) 300 that are intended to be interfaced with one or more of any part(s) and/or component(s) of the said test block(s) 102.

Without being limited, one or more of any suitable and effective connector(s) and/or connector pins (not shown) can interface with and/or extend from, any suitable and effective location(s) such as, but not limited to, a back of the base portion 108. Also without being limited, the one or more test block(s) 102 can effectively interface and/or communicate with one or more of any test sockets 98 in any suitable and effective manner known to those skilled in the art. Without being limited, the one or more test sockets 98 can also be any suitable and effective plug design(s) and/or any other suitable connector design(s) known to those skilled in the art. Without being limited, the said one or more connector pins (not shown) are interfaced with and/or plugged into, one or more of the test sockets 98.

With reference to FIG. 4, and without being limited, an example of at least one object(s) 300 being interfaced with the test block(s) 102 is shown. Without being limited, the object(s) 300 being tested in this particular example, is at least one of any suitable and effective electrical cable(s). Without limitation, one end of at least one electrical cable(s) 112 is effectively connected to at least one base socket(s) 114 suitably located in the one or more base portion(s) 108, and at least one opposing end(s) of the one or more electrical cable(s) 114 is effectively connected to at least one suitable extension socket(s) 116 suitably located in the at least one extension portion(s) 110. Without being limited, the one or more test module(s) 96 can effectively test the, safety, performance, quality, and/or conformance, of the one or more treated and/or tested object(s) 300 such as, but not limited to any, electrical cable(s) 114. The one or more said test module(s) 96 is preferably, and without limitation, located in the top equipment space 28.

Without being limited, one or more inlet(s) into the sealed treatment chamber(s) 26 and one or more outlet(s) from the sealed treatment chamber(s) 26 are preferably, and without limitation, effectively sealed with any suitable and effective valve(s) such as, but not limited to any, check valve(s). Also, it is preferred, without limitation, that one or more suitable and effective filter(s) such as, but not limited to any, HEPA filters, are suitably and effectively located before the said inlet(s) to effectively filter the air/gas(s) that enters the sealed treatment chamber(s) 26. It is also preferred, without limitation, that one or more of any suitable and effective filter(s) such as, but not limited to any, vapor(s) and/or gas(s) capturing filters, such as, but not limited to any suitable and effective activated charcoal filter(s), are suitably and effectively located after the said said outlet(s), to effectively filter the air/gas(s) that are exhausted from the sealed test chamber(s) 26.

With reference to FIGS. 5-8 and FIGS. 9-15, and without limitation, the present invention describes, a rotating object(s) holder and treatment apparatus 2, as well as methods, for decontaminating, sanitizing, disinfecting, high-level disinfecting, sterilizing, and/or effectively drying, one or more of any surface(s), all surfaces, and/or all targeted surfaces, of one or more of any object(s) 300, and where the said object(s) 300 can include, but is not limited to any, instrument(s), equipment(s), device(s), tool(s), part(s), sensor(s), probe(s), electrical device(s), ultrasonic probe(s), ultrasonic imaging device(s), esophageal imaging device(s), component(s), parts(s), component(s), cable(s), conduit(s), wire(s), dental device(s), object(s), cord(s), tube(s), pipe(s), wire(s), hose(s), conduit(s), endoscope(s), medical device(s), dental device(s), ultrasonic device(s), imaging device(s), scope(s), electronic(s), cutting tool(s), irrigation device(s), suction and/or vacuum device(s), drilling device(s), stethoscope(s), umbilical connector(s), computer mouse(s) and attached cable(s), clamp(s), blood pressure measuring and reporting device(s), blood pressure cuff(s), and/or patient monitoring equipment, and/or accessory(s).

Without being limited, the current art has also shown the absence of any apparatus(s) and/or effective apparatus(s), that can effectively, treat, decontaminate, sanitize, disinfect, high-level disinfect, sterilize, and/or effectively dry, one or more of any surface(s), all surfaces, and/or all targeted surfaces, of one or more of any object(s) 300, in any suitable and effective, enclosure(s), cabinet(s), and/or sealed treatment chamber(s), such as, but not limited to any, object(s) 300 that have any long length or longer length, such as, but not limited to any endoscope(s), blood pressure cuffs, suction hose(s), drilling apparatus(s), and/or various object(s) 300 that can be, and/or may be, connected to any cable(s), conduit(s), and/or wire(s) such as, but not limited to any, computer mouse(s), esophageal imaging device(s), topical imaging device(s), ultrasonic probe(s), imaging device(s), patient monitoring equipment, veterinary device(s), medical device(s), dental device(s), and/or any other cable(s), hoses(s), wire(s), and/or device(s).

Without limitation, one or more of the said rotating object(s) holder and treatment apparatus(s) 2 can be suitably and effectively located at one or more of any suitable and effective location(s) within any suitable and effective, chamber(s), enclosure(s), and/or sealed treatment chamber(s) 26. It is preferred, without limitation, that the one or more rotating object(s) holder and treatment apparatus(s) 2 are suitably and effectively located near and/or at, and/or about near and/or at, any suitable and effective, top area(s), and/or upper area(s), of the one or more interior space(s) within the said one or more sealed treatment chamber(s) 26. Without being limited, this can allow, create situation(s) where, and/or assist, the one or more object(s) 300, one or more part(s) and/or section(s) of the object(s) 300, and/or one or more of any, surface(s), part(s), piece(s), component(s), of the object(s) 300, to hang effectively down and into the said chamber(s), enclosure(s), and/or sealed treatment chamber(s) 26.

Without being limited, the one or more rotating object(s) holder and treatment apparatus(s) 2 has at least one first suitable and effective means 228 to hold and release the one or more object(s) 300 within the sealed treatment chamber(s) 26, and at least one second suitable and effective means 230 to hold and release the one or more object(s) 300 within the sealed treatment chamber(s) 26.

Without being limited, one or more and/or multiple, of any effective, sets and/or pairs, and/or opposing set(s) and/or pair(s), opposing numbers and/or part(s) of, matched and/or assigned pair(s) and/or set(s), of the said at least first suitable and effective means 228 to hold and release the one or more object(s) 300, and the said at least second suitable and effective means 230 to hold and release the one or more object(s) 300, can be effectively and removably interfaced with the said object(s) 300 at one or more of any suitable and effective time(s) and for any suitable and effective duration of time(s), and used, operated, and/or located, inside of the said enclosure(s), cabinet(s), and/or sealed treatment chamber(s) 26.

Without being limited, the said means 228, 230, to hold, support, and release, the one or more object(s) 300, can be one or more of any suitable and effective design(s) and construction(s) and have various effective attribute(s) such as, but not limited to any suitable and effective, size(s), shape(s), length(s), width(s), height(s), and/or geometry(s). It is preferred, without limitation, that the said one or more means 228,230 to effectively hold and effectively release the one or more object(s) 300 have at least any effective cupped and/or concave shape(s), but more preferably, and without limitation, any effective "U" and/or "H" shape(s), but even more preferably, and without limitation, any effective "V" shape(s). It is very preferred, without limitation, that the said means 228, 230, 315, 316, to hold, support, and/or release, the one or more object(s) 300, include, without limitation, at least a first plurality of V-shaped members 228 and a second plurality of V-shaped members 230.

Without being limited, the said means 228, 230, 315, 316, to hold, support, release, and/or transfer, the one or more object(s) 300, can be constructed from or with, one or more of any suitable and effective, member(s), support(s), rod(s), tube(s), and/or bar(s) (Herein called "Member(s)"). The said member(s) can be constructed and/or manufactured from any suitable and effective materials, however, it is preferred, without limitation, that they are constructed from any suitable and effective grade(s) of stainless steel that is FDA approved, such as, but not limited to 316 or 316L stainless steel that is effectively polished in a manner known to those skilled in the art.

It is preferred, without limitation, that each of the one or more means 228,230 to effectively hold and effectively release the one or more object(s) 300, such as, but not limited to any, first plurality of V-shaped members 228 and second plurality of V-shaped members 230, is at least designed and constructed so that the said object(s) 300 do not move and/or do not effectively move, until the said means 228,230, and/or the first plurality of V-shaped members 228 and second plurality of V-shaped members 230, are effectively moved with, are subjected to, and/or undergo, any effective, rotation, rotating, forward rotating, backward rotating, turning, lateral, clockwise, counter-clockwise, forward momentum, pivoting forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), that causes the one or more said object(s) 300 to be passed and/or moved from the one or more of any suitable and effective first, support(s), member(s), holder(s), and/or first plurality of V-shaped members 228, to the one or more of any suitable and effective second, support(s), member(s), holder(s), and/or second plurality of V-shaped members 230, and also where any suitable and effective, reverse, reverse direction, reflecting, returning, backward, and/or opposite, rotation, rotating, turning, forward rotating, backward rotating, lateral, clockwise, counter-clockwise, forward momentum, pivoting forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), passes and/or moves the one or more said object(s) 300, from the one or more of any suitable and effective second support(s), member(s), holder(s), and/or second plurality of V-shaped members 228, to the one or more of any suitable and effective first, support(s), member(s), holder(s), and/or first plurality of V-shaped members 230.

Without being limited, the one or more of any suitable and effective first, support(s), member(s), holder(s), and/or first plurality of V-shaped members 228, and the one or more of any suitable and effective second, support(s), member(s), holder(s), and/or second plurality of V-shaped members 230, can hold, position, and/or locate, the one or more object(s) 300 at one or more of any suitable and effective, location(s), angle(s), and/or orientation(s) at one or more of any suitable and effective time(s) and for any suitable and effective duration of time(s). It is preferred, without limitation, that the one or more of any means that holds and/or supports 228,230 the one or more object(s) 300 are positioned and/or oriented, in, at, about, and/or close to, any effective, upward and/or ceiling facing, angle(s), direction(s), and/or orientation(s), when holding and/or supporting the one or more object(s) 300.

Without limitation, when the object(s) 300 is interfaced and/or held by the one or more of any means that holds and/or supports 228,230 the one or more object(s) 300, the said means that holds and/or supports 228,230 the one or more object(s) 300, and is in contact with and/or supporting the object(s) 300, is positioned, located, and/or oriented, in, at, about, and/or close to, one or more of any effective, angle(s), direction(s), and/or orientation(s), and preferably, and without limitation, any effective, angle(s), direction(s), and/or orientation(s), that is, in, at, about, and/or close to, upward facing and/or ceiling facing, when holding and/or supporting the one or more object(s) 300, and more preferably, and without limitation, any effective, angle(s), direction(s), and/or orientation(s), that is between 250 degree to 110 degree and/or at one or more of any effective angle(s) and/or orientation(s) between 8:00 to 4:00, when holding and/or supporting the one or more object(s) 300, and even more preferably, and without limitation, any effective, angle(s), direction(s), and/or orientation(s), that is between 280 degree to 80 degree and/or at one or more of any effective angle(s) and/or orientation(s) between 10:00 to 2:00, when holding and/or supporting the one or more object(s) 300, and very preferably, and without limitation, any effective, angle(s), direction(s), and/or orientation(s), that is between 290 degree to 10 degree and/or at one or more of any effective angle(s) and/or orientation(s) between 11:00 to 1:00, when holding and/or supporting the one or more object(s) 300, and extremely preferably, and without limitation, any effective, angle(s), direction(s), and/or orientation(s), that is between 299 degree to 1 degree and/or at one or more of any effective angle(s) and/or orientation(s) between any 11:59 to 12:01, when holding and/or supporting the one or more object(s) 300, and super preferably, and without limitation, any effective, angle(s), direction(s), and/or orientation(s), at about 0 degree and/or at one or more of any effective angle(s) and/or orientation(s) at about 12:00, when holding and/or supporting the one or more object(s) 300.

Also, and without being limited, the one or more of any suitable and effective first, support(s), member(s), holder(s), and/or first plurality of V-shaped members 228, and the one or more of any suitable and effective second, support(s), member(s), holder(s), and/or second plurality of V-shaped members 230, can have any suitable and effective, rotation, turning, rotating, forward rotating, backward rotating, lateral, clockwise, counter-clockwise, forward momentum, pivoting forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), at any suitable and effective, speed(s), momentum(s), and/or velocity(s).

Without limitation, the one or more object(s) 300 can be moved between and/or moved back and forth between, the one or more of any suitable and effective first, support(s), member(s), holder(s), and/or first plurality of V-shaped members 228, and the one or more of any suitable and effective second, support(s), member(s), holder(s), and/or second plurality of V-shaped members 230, at any suitable and effective, speed(s), duration of time(s), momentum(s), and/or velocity(s).

Without being limited, the rotating object(s) holder and treatment apparatus 2, preferably includes at least one preferably and without limitation, rotating cable tube(s), elongated member(s), and/or rod(s) 210, at least one mounting bracket(s) 212, at least one suitable and effective motor(s) with at least one suitable and effective gear reduction(s) 214, at least one motor controller(s) 216, at least one first snap switch(s) 218 and at least one second snap switch 220.

Without being limited, the at least one preferably and without limitation, rotating, cable tube(s), elongated member(s), and/or rod(s) 210, preferably, and without limitation, includes at least one of any suitable and effective, rod(s), elongated member(s), tube(s), shaft(s), beams, tubular rod(s), and/or elongated structure(s) 222, at least one of any suitable and effective, first mounting rod(s), elongated member(s), tube(s), shaft(s), beam(s), tubular rod(s), and/or elongated structure(s) 224, at least one of any suitable and effective, second mounting rod(s), elongated member(s), tube(s), shaft(s), beam(s), tubular rod(s), and/or elongated structure(s) 226, a first plurality of any suitable and effective member(s) that are preferably, and without limitation, V-shaped members 228 and a second plurality of any suitable and effective member(s) that are preferably, and without limitation, also V-shaped members 230. It is preferred, without limitation, that the one or more support gaps 228, 230, 315, 316, have a V-shape, however, one or more of any other suitable and effective shape(s) can also be used such as, but not limited to any, "U" shape(s) and/or "H" shape(s). Without being limited, the at least one rod(s), tube(s), tubular rod(s), and/or elongated structure(s) 222, first mounting rod(s) 224, and second mounting rod(s) 226, can be any suitable and effective, rod(s), tube(s), beam(s), support(s), conduit(s), and/or elongated structure(s).

Without being limited, a bottom of the first plurality of V-shaped members 228 are preferably, but without limitation, welded to the first mounting rod(s) 224. The first mounting rod(s) 224 is preferably, but without limitation, welded to the rod(s), tube(s), tubular rod(s), and/or elongated structure(s) 222. A bottom of the second plurality of V-shaped members 230 are preferably, but without limitation, welded to a second mounting rod(s) 226. The second mounting rod(s) 226 is preferably, but without limitation, welded to the rod(s), tube(s), tubular rod(s), and/or elongated structure(s) 222, such that the first plurality of V-shaped members 228 are located opposite and/or effectively about opposite, the second plurality of V-shaped members 230. The at least one mounting bracket(s) 212 includes a base member(s) 236, a first leg(s) 238, a second leg(s) 240, a first switch plate(s) 242 and a second switch plate(s) 244. The first leg(s) 238 extends outward from a first end of the base member(s) 236 and the second leg(s) 240 extends outward from a second end of the base member(s) 236. The first switch plate(s) 242 extends outward from one side of the first leg(s) 238 and the second switch plate(s) 244 extends from an opposite side of the first leg(s) 238. A first mounting flange(s) 246 extends from a bottom of the first leg(s) 238 and a second mounting flange(s) 248 extends from a bottom of the second leg(s) 240.

Without being limited, at least one cabinet 250 for uses including, but not limited to any, decontamination, sanitization, disinfection, high-level disinfection, sterilization, and/or effectively drying, one or more of any surface(s), all surfaces, and/or all targeted surfaces, of one or more of any object(s) 300, includes at least one of any suitable and effective, enclosure(s), treatment area(s), chamber(s), and/or treatment chamber(s) (Herein also called "Sealed Treatment Chamber(s)") 252,26.

Without being limited, the sealed treatment chamber(s) 252,26, includes opposing side walls 254. Without being limited, the rod(s), tube(s), tubular rod(s), and/or elongated structure(s) 222 is rotationally and/or pivotally retained on opposing side walls 254 with at least one pair of flanged bearing blocks 256, 258. Any effective number, but preferably, and without limitation, at least two, tube holes 260 are formed through the opposing side walls 254 to receive the one or more rod(s), tube(s), tubular rod(s), and/or elongated structure(s) 222. The at least one pair(s) of flanged bearing blocks 256, 258 are preferably retained on outside surfaces of the opposing side walls 254. The first and second snap switches 218, 220 are attached to the first and second switch plates 242, 244. The motor(s) with gear reduction(s) 214 is attached to the base member(s) 236 of the mounting bracket(s) 212 with fasteners 262. An output shaft(s) 264 of the motor(s) with gear reduction(s) 214 is inserted into an end of the rod(s), tube(s), tubular rod(s), and/or elongated structure(s) 222. A threaded hole(s) 263 is formed through an end(s) of the rod(s), tube(s), tubular rod(s), and/or elongated structure(s) 222. A set screw(s) 266 is threaded into the threaded hole(s) 263. The set screw(s) 266 is long enough to extend outward from an outer diameter of the rod(s), tube(s), tubular rod(s), and/or elongated structure(s) 222.

Figure 8:
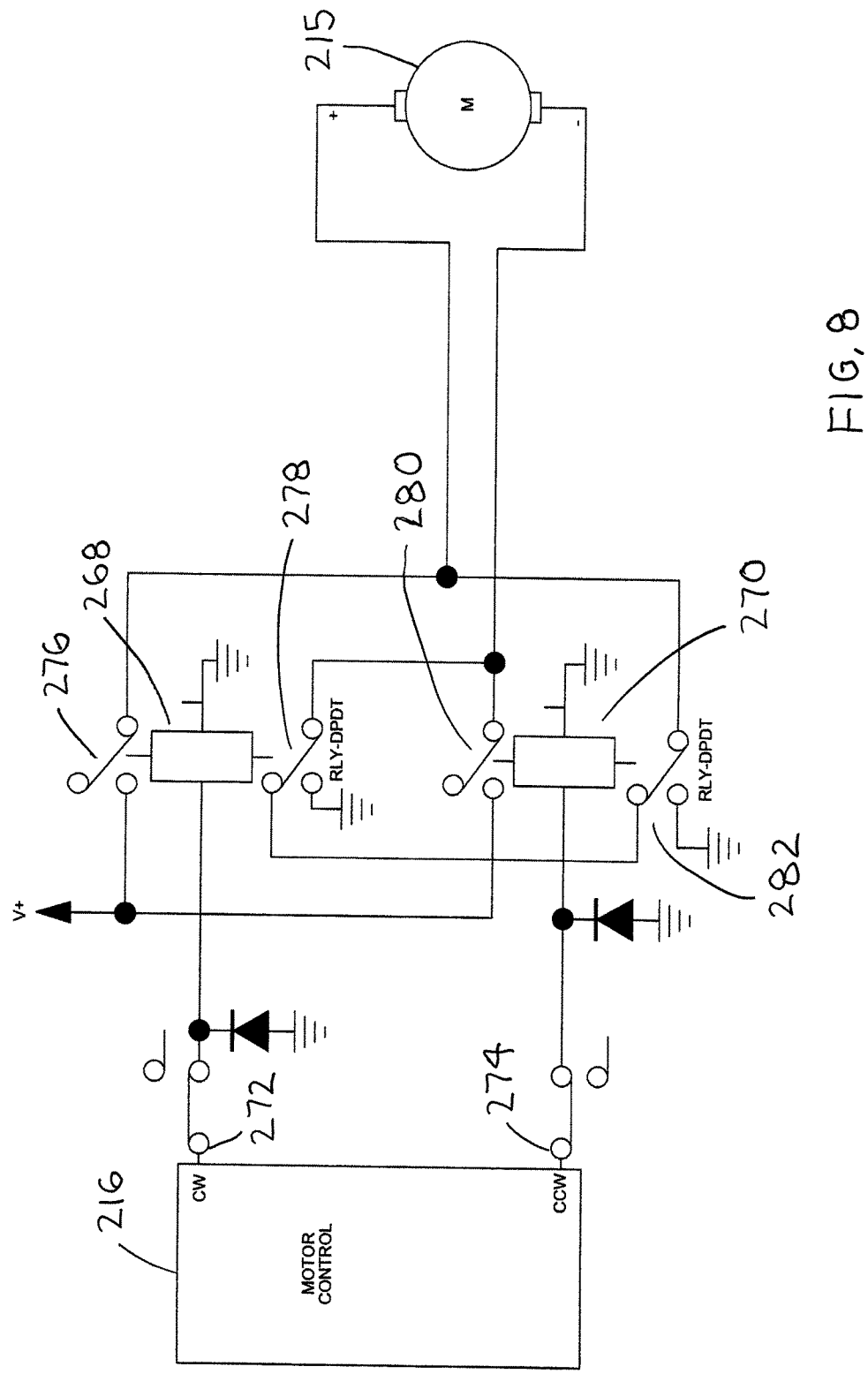
FIG. 8 is a schematic diagram of an electrical circuit for controlling rotation of a rotating cable holder in accordance with the present invention.

With reference to FIG. 8, and without limitation, a clockwise DPDT relay(s) 268 and a counter clockwise DPDT relay(s) 270 are used to provide power to a motor(s) 215 of the motor with gear reduction(s) 214. The motor controller(s) 216 includes a CW terminal(s) 272, which outputs a clockwise voltage and CCW terminal(s) 274, which outputs a counter clockwise voltage. The clockwise voltage is outputted for a first period of time and the counter clockwise voltage is outputted for a second period of time. The clockwise voltage is used to energize a clockwise solenoid(s) of the clockwise DPDT relay(s) 268, which closes a first contact(s) 276 to supply a positive terminal(s) of the motor(s) 215 with the clockwise voltage and a second contact(s) 278 to provide a ground path for a ground terminal of the motor(s) 215. The motor(s) 215 rotates the rotating cable tube(s) and/or rod(s) 210 in a clockwise direction, until the setscrew(s) 266 forces the normally closed first snap switch(s) 218 to open. The opening of the first snap switch(s) 218 stops rotation of the rotating cable tube(s) and/or rod(s) 210. After the first period of time is over, the motor controller(s) 216 outputs a counter clockwise voltage for a second period of time. The counter clockwise voltage is used to energize a counter clockwise solenoid of the counter clockwise DPDT relay(s) 270, which closes a first contact(s) 280 to supply a negative terminal of the motor(s) 215 with the counter clockwise voltage and a second contact(s) 282 to provide a ground path for a positive terminal of the motor(s) 215. The rotating cable tube(s) and/or rod(s) 210 preferably, but without limitation, rotates in a counter clockwise direction, until the setscrew(s) 266 forces the normally closed second snap switch(s) 220 to open. The opening of the second snap switch(s) 220 stops rotation of the rotating cable tube(s) and/or rod(s) 210. After the second period of time is over, the motor controller(s) 216 outputs the clockwise voltage for a new first period of time.

Without being limited, one or more of any suitable and effective object(s) 300 can be processed, decontaminated, sanitized, disinfected, high-level disinfected, sterilized, and/or effectively dried, using the present invention, such as, but not limited to any, esophageal probe(s), topical ultrasonic imaging device(s), medical device(s), dental device(s), veterinary device(s), and/or ultrasonic probe(s) 284,300, that can also include, without limitation, one or more of any, sensor(s), transceiver(s), and/or ultrasonic head(s) 286, handle(s) 288, cable(s), wire(s), and/or cord(s) 290, and/or plug(s) and socket(s) (not shown). Typically, and without limitation, only the ultrasonic head 286 and the at least one handle 288 are disinfected, which leaves the cable(s) and/or cord(s) 290 and plug end(s) (not shown) untreated, which can become a vector of transmission for various hospital borne infection(s).

Without being limited, the rotating object(s) holder and treatment apparatus 2 and its rotating cable tube(s) and/or rod(s) 210 provides an effective means for entire object(s) 300 such as, but not limited to any, ultrasonic probe(s) 284,300 and their various part(s), to be effectively, processed, decontaminated, sanitized, disinfected, high-level disinfected, sterilized, and/or effectively dried.

Without being limited, the object(s) 300, one or more of any part(s) of any object(s) 300, any one or more effective part(s) and/or length(s) of any object(s) 300, one or more of any section(s) of any object(s) 300, and/or any one or more effective part(s) of the object(s) 300, such as, but not limited to any, cable(s), wire(s) and/or cord(s), 290, can be effectively located between, over and/or through, two adjacent V-shaped members 228 of the rotating cable tube(s) and/or rod(s) 210.

It is preferred, without limitation, that an effectively long portion, but at least any effective length(s) and/or portion(s), of the object(s) 300 such as, but not limited to, one or more of any cable(s), wire(s), and/or cord(s) 290, and/or plug(s) and/or connector(s), effectively extends from one side of the V-shaped members 228, and another part of the object(s) 300, but at least any effective length(s) and/or portion(s), such as, but not limited to any, cable(s), wire(s), and/or cord(s), 290 and any attached, part(s), device(s), tool(s), and/or sensor(s), such as, but not limited to any, transceiver(s), cutting tool(s), and/or ultrasonic imaging device(s) and/or apparatus(s), effectively extends from an opposing side of the V-shaped members 228. For example, and without limitation, any ultrasonic head(s) 286 and any handle(s) 288 can effectively extend from an opposing side of the V-shaped members 228.

Without being limited, the cycle for processing, decontamination, sanitization, disinfection, high-level disinfection, and/or sterilization, of the one or more object(s) 300 in the sealed treatment chamber(s) 252,26, includes at least one treatment cycle(s), where the one or more object(s) 300 are effectively treated with one or more treatment agent(s) 100, and at least one drying cycle(s), where the object(s) 300 are effectively dried and the deployed treatment agent(s) 100 are effectively removed from the surface(s) of the treated object(s) 300. Without being limited, the one or more object(s) 300 located in the sealed treatment chamber(s) 252,26, can be dried with one or more of any suitable and effective means such as, but not limited to any, ambient air, heated air/gas(s), heated ambient air, vacuum, and/or any other suitable means and/or method(s), at one or more of any suitable and effective time(s) and for any suitable and effective duration of time(s). Also, without being limited, the one or more object(s) 300 can also be effectively dried before they undergo any one or more step(s) to treat their surface(s) for any, decontamination, sanitization, disinfection, high-level disinfection, and/or sterilization.

Without being limited, the rotating cable tube(s) and/or rod(s) 210 can be rotated between 0 to about 180 degrees or more, forward and/or backward, but at least any suitable and effective angle(s) and/or degree(s), to expose one or more of any untreated and/or undried area(s) of the object(s) 300 such as, but not limited to any, cable(s), wire(s), and/or cord(s), 290, that is retained between the two adjacent V-shaped members 228, to any deployed treatment agent(s) 100, and/or any air/gas(s) that are used to dry the said treated object(s) 300.

However, and without being limited, the rotating cable tube(s) and/or rod(s) 210 can be preferably rotated about 180 degrees, forward and/or backward, but at least any suitable and effective angle(s) and/or degree(s), to expose one or more of any untreated and/or undried area(s) of the object(s) 300 such as, but not limited to any, cable(s), wire(s), and/or cord(s), 290, that is retained between the two adjacent V-shaped members 228, to any deployed treatment agent(s) 100, and/or any air/gas(s) that are used to dry the said treated object(s) 300. Without being limited, any other effective angular rotations besides 180 degrees can also be used.

Without being limited, the rotating cable tube(s) and/or rod(s) 210 can be effectively, moved, rotated, and/or rotated about 180 degrees or more, forward and/or backward, one or more times, but at least any effective and/or efficacious, number(s) of time(s), quantity(s) of time(s), and/or direction(s), to effectively move the object(s) 300 back and forth between, the one or more of any suitable and effective first, support(s), member(s), holder(s), and/or first plurality of V-shaped members 228, and the one or more of any suitable and effective second, support(s), member(s), holder(s), and/or second plurality of V-shaped members 230, when any effective and/or efficacious, quantity, flow, and/or concentration, of treatment agent(s) 100 is present inside of the sealed treatment chamber(s) 252,26, for the decontamination, sanitization, disinfection, high-level disinfection, sterilization, and/or effective drying, of the one or more of any surface(s), all surfaces, and/or all targeted surfaces, of the one or more of any object(s) 300.

Also, without limitation, the rotating cable tube(s) and/or rod(s) 210 can also be effectively, moved, rotated, and/or rotated about 180 degrees or more, forward and/or backward, one or more times, but at least any effective and/or efficacious, number(s) of time(s), quantity(s) of time(s), and/or direction(s), to effectively move the object(s) 300 back and forth between, the one or more of any suitable and effective first, support(s), member(s), holder(s), and/or first plurality of V-shaped members 228, and the one or more of any suitable and effective second, support(s), member(s), holder(s), and/or second plurality of V-shaped members 230, when any effective and/or efficacious, quantity, flow, temperature(s), and/or concentration, of air/gas(s) for drying various surface(s) within the sealed treatment chamber(s) 252,26, is present inside of the sealed treatment chamber(s) 252,26, for the effective drying, of the one or more of any surface(s), all surfaces, and/or all targeted surfaces, of the one or more of any object(s) 300.

Without being limited, and with regards to FIGS. 5-8, an even more detailed description and method, is given for the current invention. Many variations and combination(s) are possible. Without being limited, one or more of any suitable and effective object(s) (300) of any suitable and effective design(s), shape(s), length(s), geometry(s), including any directly and/or indirectly connected part(s) and component(s), can be used in the present invention such as, but not limited to any, data or information conduit(s), fiber optic line(s), light transferring conduit(s), instrument(s) equipment(s), sensor(s), power supply(s), medical equipment(s), dental equipment(s), industrial equipment(s), product(s), accessory(s), device(s), tool(s), sensor(s), probe(s), ultrasonic imaging device(s), esophageal imaging device(s), component(s), parts(s), component(s), cable(s), conduit(s), wire(s), dental device(s), object(s), equipment(s), accessory(s), tool(s), tube(s), pipe(s), wire(s), hose(s), conduit(s), endoscope(s), medical device(s), ultrasonic device(s), imaging device(s), scope(s), electronic(s), cable(s), cutting tool(s), irrigation device(s), suction device(s), vacuum device(s), drilling device(s), stethoscope(s), umbilical connector(s), computer mouse(s) and attached cable(s), clamp(s), cord(s), blood pressure measuring and reporting device(s), stethoscope(s), ECG device(s), SPO2 device(s), temperature sensing device(s), TOCO device(s), patient monitoring equipment or device(s), cord(s) (290), ultrasonic probe(s) (284), ultrasonic imaging device(s) and/or probe(s) (284) attached to any cable(s) and/or any cord(s) (290), and/or electrical cable(s) (104), including, but not limited to, any of their or any associated, part(s), accessory(s), device(s), and component(s), (Herein called "Object(s)" (300)).

First, one or more object(s) (300) is positioned into one or more of any suitable and effective treatment chamber(s) and/or test chamber(s) (26), and effectively interfaced with one or more of any suitable rotating member(s) (315)(228) of the rotating object(s) holder(s) (02), and more preferably and without limitation, any suitable and effective number of first member(s) (315) and/or one or more first v-shaped member(s) (228)(315). It is preferred, without limitation, that the first v-shaped members(s) (228)(315) are initially oriented in or close to any vertical orientation.

Without being limited, the first v-shaped members(s) (228)(315) and the second v-shaped members(s) (230)(316), and any of the open area(s) (305)(325)(335) they form, can be orientated in and/or open at, one or more of any suitable angle(s) and/or orientation(s). It is preferred, without limitation, that the first v-shaped members (228)(315) are initially located at any effective angle between about +35 degree angle and +145 degree angle, more preferably and without limitation, at any angle(s) between about +50 degree angle to +130 degree angle, and even more preferably and without limitation, about 90 degree angle and/or about vertical.

It is preferred, without limitation, that the one or more object(s) (300) can be effectively and removably interfaced with these open v-shaped open area(s) (305)(325)(335) formed by the v-shaped member(s) (315)(316)(228)(230). It is preferred, without limitation, that the second v-shaped members (230) are identical and/or effectively close to being identical, to the first v-shaped members (228). Without being limited, one or more of any rotating object(s) holder(s) (02) can be suitably and effectively located and used within any treatment chamber(s) and/or test chamber(s) (26).

Without being limited, the various member(s) (315)(316)(228)(230), can be used for purposes including, but not limited to, holding, gripping, and supporting, the one or more object(s) (300), preferably in a removable manner. Also without being limited, the one or more, but preferably a plurality, of member(s) (315)(316)(228)(230), can be one or more of any suitable and effective size(s), length(s), width(s), shape(s), and/or geometry(s), and can be oriented in one or more of any suitable and effective, orientation(s) and/or angle(s). For example, various member(s) and/or structural protrusion(s) (Herein called "Member(s)" (315)(316)), can be combined in any suitable and effective manner known to those skilled in the art, to form any effective means, structure(s), and/or shape(s), for holding the various object(s) (300) such as, but not limited to any, fork shape(s), "H" shape(s), "V" shape(s), "U" shape(s), and/or inverted arch shape(s), but at least in a manner and design, so they can hold, capture, and/or release, one or more of any object(s) (300) at any suitable and effective time(s).

It is preferred, without limitation, that the member(s) (315)(316)(228)(230) are combined to form any suitable and effective "V" shape(s), and the open space(s) and/or area(s) (305) formed within the open V-shaped area(s) between the member(s) (315)(316)(228)(230) are suitably and effectively sized to capture and removably hold the object(s) (300). Without being limited, the members (315)(316)(228)(230) that hold and/or support the object(s) (300) should at least be designed so that the various object(s) (300) and/or any parts of the object(s) (300) can be easily transferred between, preferably and without limitation, back and forth between, the first one or more v-shaped member(s) (228)(315) and the second one or more v-shaped member(s) (230)(316). The member(s) (315)(316) can be constructed from any suitable and effective material(s). It is preferred, without limitation, that the various member(s) and more particularity, any of the v-shaped member(s), are constructed from stainless steel that is polished.

Without being limited, various attributes related to the member(s) (315)(316)(228)(230), and any related part(s) and component(s), such as, but not limited to any, shape(s), material(s) used for part fabrication, geometry, and/or size(s), are important, especially when the rotating object(s) holder(s) (02), or more particularly when the v-shaped member(s) (228)(230) and/or any other suitable and effective combination(s) and design(s) of the member(s) (315) (316), are effectively moved, rotated, pivoted, holding and/or supporting the object(s) (300), and/or passing the object(s) (300) from one or more first member(s) (315) or first v-shaped member(s) (228) to one or more second member(s) (316) or second v-shaped member(s) (230). However, and without limitation, another important attribute for the effective operation of the rotating object(s) holder (02) and effective processing, drying, and treatment(s), of the surface(s) of the object(s) (300), is the distance(s) between the various part(s) and surface(s) that are used to interface with, hold, support, release, and/or pass the object(s) (300) back and forth between the first member(s) (315)(228) and the second member(s) (316)(230) (Herein called "Holding Surface(s)") (320), which are preferably and without limitation, at least effective. Without being limited, the holding surface(s) (320) can also include the various surface(s) of any member(s) (315)(316) that touch and contact the object(s) (300) when they are held by the one or more member(s) (315)(316).

Without being limited, it is preferred, that the distance between the holding surface(s) (320) of the first member(s) (315)(228) and the holding surface(s) of the second member(s) (316)(230), is at least 0.10 inches or more, it is more preferred, that the distance between the holding surface(s) (320) of the first member(s) (315)(228) and the holding surface(s) of the second member(s) (316) (230), is at least one inch or more, it is even more preferred, that the distance between the holding surface(s) (320) of the first member(s) (315)(228) and the holding surface(s) of the second member(s) (316)(230), is at least two inches or more, and it is very preferred that the distance between the holding surface(s) (320) of the first member(s) (315)(228) and the holding surface(s) of the second member(s) (316)(230), is at least three inches or more.

The movement and transfer of the one or more object(s) (300) from the first one or more member(s) (315)(228) to the second one or more members (316)(230) occurs by effectively, moving, rotating, and/or pivoting, the various v-shaped members (228)(230) any effective, distance(s), angle(s), and/or orientation(s). Without being limited, an important difference between the prior art and the present invention, is that in the present invention, the one or more member(s) (315)(316)(228)(230) that are used to releasably hold and/or support, the object(s) (300) as they are passed from one or more first member(s) (315)(228) to one or more second member(s) (316)(230), are effectively moved, rotated, and/or pivoted, in one or more of any effective, rotation, rotating, forward rotating, backward rotating, lateral, clockwise, counter-clockwise, forward momentum, pivoting forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), instead of being moved vertically, or about vertically, in an up and down vertical motion.

It is preferred, without limitation, that the object(s) (300) are passed from the first member(s) (315)(228) to the second member(s) (316)(230) as both the first member(s) (315) (228) and the second member(s) (316)(230) effectively rotate about equally around a common point, for an effective distance and/or an effective angle of movement(s), to cause the object(s) (300) to pass from the first member(s) (315) (228) to the second member(s) (316)(230). It is also preferred, without limitation, that the object(s) (300) are passed back from the second member(s) (316)(230) back to the first member(s) (315)(228) as both the second member(s) (316) (230) and the first member(s) (315)(228) effectively rotate back about equally around a common point, for an effective distance and/or an effective angle of movement(s), to cause the object(s) (300) to pass back from the second member(s) (316)(230) back to the first member(s) (315)(228). This can be repeated for any number of effective time(s) for any of the step(s) used to treat and dry the surface(s) of the object(s) (300).

More particularly, and without limitation, it is preferred that the distance(s) between the first member(s) (315) and the second member(s) (316), and/or the first v-shaped members (228) and the the second v-shaped members (230), and/or the distance(s) between the first open area(s) (325) and the second open area(s) (335), and/or the distance(s) between the first junction(s) (330) and the second junction(s) (340), are the same and/or about the same. It is also preferred, without limitation, that the second member(s) (316) and/or the second v-shaped members (230) are identical to the first member(s) (315) and/or the first v-shaped members (228), and mirror them. Without being limited, it is also preferred that the second member(s) (316) and/or the second one or more v-shaped members (230) are positioned opposite and opposed to the first member(s) (315) and/or the one or more v-shaped member(s) (228), on the same plane.

Without being limited, it is also preferred, that the object(s) (300) can be effectively passed from any first support(s) and/or holding member(s) (315)(228) to any second support(s) and/or holding member(s) (316)(230), in any effective manner, speed, and/or rate of travel, so that any shadowed and/or covered surface(s) from any contact and/or interfacing with the first and/or second support member(s) (315)(316)(228)(230), do not touch any surface(s), and are able to be effectively treated when moved to any of the opposite and/or alternate one or more member(s) (315) and/or (316).

Once the treatment chamber(s) and/or test chamber(s) (26), is effectively closed and/or sealed, the object(s) (300) can first be effectively dried, if desired and/or needed, using any suitable and effective means to treat and dry the atmosphere(s) and/or any surface(s) within the treatment chamber(s) and/or test chamber(s) (26) including any object(s) (300) surface(s), such as, but not limited to any, dehumidified air/gas(s), heated air/gas(s), fresh air/gas(s) flowed through the treatment chamber(s) and/or test chamber(s) (26), negative pressure(s), and/or vacuum, for any effective number of time(s), and for any effective duration of time(s).

Without being limited, during this pre-drying step(s), surfaces of the object(s) (300) are effectively dried while the object(s) (300) are interfaced with the first member(s) (315) and/or the one or more first v-shaped member(s) (315)(228). After the surface(s) of the object(s) (300) are effectively dry, the object(s) (300) are then transferred over to, and then interfaced with, the second member(s) (316) and/or the one or more second v-shaped member(s) (316)(230). Preferably, and without limitation, this effectively exposes any, shadowed surface(s), undried surface(s), and/or unprocessed surface(s), and/or any surface(s) of the object(s) (300) that may have been in contact with the first member(s) (315) and/or the one or more first v-shaped member(s) (228), to the atmosphere, heated air/gas(s), dehumidified air/gas(s), drying air/gas(s), negative pressure atmosphere, and/or vacuum, within the treatment chamber(s) and/or sealed treatment chamber(s) (26). Without being limited, this transfer of the object(s) (300) between the various holding member(s) (315)(316)(228)(230), can happen one or more time(s) for each processing, drying, and/or treatment step(s) such as, but not limited to any surface, decontamination, sanitization, disinfection, high-level disinfection, and/or sterilization, and for any effective quantity of time(s), and for any effective duration of time(s).

Without being limited, after any pre-treatment and/or drying step(s), any one or more of any surface(s) such as, but not limited to, any, object(s) (300) surface(s), and/or surface(s) within any treatment chamber(s) and/or sealed treatment chamber(s) (26), can then be treated with one or more of any suitable and effective means for any suitable and effective, treatment, decontamination, sanitization, disinfection, high level disinfection, and/or sterilization, of the various surface(s) within the the sealed treatment chamber(s) (26), such as, but not limited to any effective, vapor(s), gas(s), UV light(s), particle(s) plasma(s), and/or aerosol(s) (Herein called "Surface Treatment(s)". It is preferred, without limitation, that the said surface(s) are treated with any effective aerosol(s), and even more preferred, and without limitation, any aerosol(s) and/or vapor(s) formed from any aqueous solution(s) containing peroxyacetic acid, all in a manner known to those skilled in the art.

Without being limited, during this surface treatment(s) step(s) using the one or more said means for treating the various surface(s) within the treatment chamber(s), test chamber(s), and/or sealed treatment chamber(s) (26), the surfaces of the object(s) (300) are effectively treated, preferably with any effective aerosol(s) and/or vapor(s), while the object(s) (300) are interfaced with the first one or more member(s) (315) and/or first v-shaped member(s) (228). After the surface(s) of the object(s) (300) are effectively treated, for any effective duration of time(s), the object(s) (300) are then transferred over to, and then interfaced with, the second one or more member(s) (316) and/or the second v-shaped member(s) (230). Preferably, and without limitation, this effectively exposes any surface(s) that are, shadowed surface(s), untreated surface(s), unprocessed surface(s), and/or any surface(s) of the object(s) (300) that may have been in contact with the first one or more member(s) (315) and/or the first v-shaped member(s) (228) and/or any other surface(s), to the atmosphere and deployed treatment agent(s) 100, within the treatment chamber(s), test chamber(s), and/or sealed treatment chamber(s) (26). Without being limited, the object(s) (300) can be transferred back and forth between the the first member(s) (315) and/or the first one or more v-shaped member(s) (228), and the second member(s) (316)(230) and/or the second one or more v-shaped member(s) (230), any number of time(s) and for any duration of time(s), to expose all of the surface(s) of the object(s) (300) and/or all of the object(s) (300) surface(s) targeted for effective treatment, to the surface treatment(s), for any suitable and effective, treatment outcome(s) and result(s).

Without being limited, the object(s) (300) can also be dried after each time they are treated in their respective first or second member(s) (315)(316) and/or v-shaped member(s) (228)(230), or after they have been moved to one or more new or different member(s) and/or v-shaped member(s) (228)(230), and before they are treated by any surface treatment(s) at these alternate, new, and/or returning location(s).

It is also preferred, without limitation, that after the one or more treatment step(s) is effectively completed, the object(s) (300) are returned back to the first member(s) (315) and/or the first one or more v-shaped member(s) (228) before any final drying step(s) are completed.

After the effective treatment of any, but preferably all, of the object(s) (300) surface(s), and/or any surfaces within the treatment chamber(s), test chamber(s), and/or sealed treatment chamber(s) (26), any, but preferably all, of the object(s) surface(s) and/or the surface(s) within the treatment chamber(s), test chamber(s), and/or sealed treatment chamber(s) (26), can be effectively dried, using any suitable and effective means to treat and dry the atmosphere(s) and/or any surface(s) within the treatment chamber(s), test chamber(s), and/or sealed treatment chamber(s) (26) including any object(s) (300) surface(s), such as, but not limited to any, dehumidified air/gas(s), heated air/gas(s), fresh and/or heated air/gas(s) flow through the treatment chamber(s), test chamber(s), and/or sealed treatment chamber(s) (26), negative pressure(s), and/or vacuum, for any suitable and effective time(s) and/or duration of time(s).

It is preferred, without limitation, that at least heated air/gas(s), using effectively filtered fresh air from outside of the treatment chamber(s), test chamber(s), and/or sealed treatment chamber(s) (26), that is effectively heated before it is flowed through the treatment chamber(s), test chamber(s), and/or sealed treatment chamber(s) (26), is used to effectively dry all of the vaious surface(s) within the sealed treatment chamber(s) (26). The air/gas(s) can be heated to any suitable and effective temperature(s), preferably and without limitation, at least any effective temperature(s) between 60 to 200 degree Fahrenheit, and even more preferably, and without limitation, any temperature(s) between 90-120 degree Fahrenheit. It is preferred, without limitation, that if any chemicals were used to treat the various surface(s) within the treatment chamber(s), test chamber(s), and/or sealed treatment chamber(s) (26), the heated air/gas(s) that are flowed through the treatment chamber(s), test chamber(s), and/or sealed treatment chamber(s) (26), are effectively filtered after they leave the treatment chamber(s), test chamber(s), and/or sealed treatment chamber(s) (26), and before they are removed from the entire treatment apparatus and/or machine and into the surrounding environment.

Without being limited, during the said drying step(s), surfaces of the object(s) (300) are effectively dried while the object(s) (300) are interfaced, preferably and without limitation, with the first one or more member(s) (315) and/or the first v-shaped member(s) (228). After the surface(s) of the object(s) (300) are effectively dry, the object(s) (300) are then transferred over to, and then interfaced with, the second one or more member(s) (316) and/or the second v-shaped member(s) (230). Preferably, and without limitation, this effectively exposes any, shadowed surface(s), undried surface(s), and/or unprocessed surface(s), and/or any surface(s) of the object(s) (300) that may have been in contact with the first one or more member(s) and/or first v-shaped member(s) (228), to the atmosphere, heated air/gas(s), dehumidified air/gas(s), drying air/gas(s), negative pressure atmosphere, and/or vacuum, within the treatment chamber(s), test chamber(s), and/or sealed treatment chamber(s) (26). Without being limited, this transfer of the object(s) (300) between the various holding member(s) (228)(230)(315)(316), can happen one or more time(s), and for any effective duration of time(s).

Also without being limited, after the various surface(s) within the treatment chamber(s), test chamber(s), and/or sealed treatment chamber(s) (26), are effectively dry, and the drying step(s) are completed, the atmosphere(s) within the treatment chamber(s), test chamber(s), and/or sealed treatment chamber(s) (26), can also be purged if needed, with fresh air that is preferably and without limitation, effectively filtered before it enters the treatment chamber(s), test chamber(s), and/or sealed treatment chamber(s) (26), and is also effectively filtered before it is exhausted into the surrounding environment, until any chemical concentration(s) inside the treatment chamber(s), test chamber(s), and/or sealed treatment chamber(s) (26), are reduced to any suitable and effective level(s), all in a manner known to those skilled in the art.

With reference to FIGS. 9-14, and without limitation, additional means to hold, transfer, move, support, retain, removably hold, removably support, and/or removably retain, the said one or more object(s) 300, with one or more of any suitable members 228, 230, 315, 316, and more particularly, and without limitation, to one or more of any suitable and effective support gaps 228, 230, 315, 316, and even more particularly, and without limitation, to one or more of any suitable and effective retention structure(s) 390, that includes one or more of any suitable and effective, shaped member(s) such as, but not limited to any, first forked shaped member(s), first prong shaped member(s), first V-shaped member(s), first U-shaped member(s), and/or first H-shaped member(s) (228) and/or first member(s) (315), and one or more of any suitable and effective, second forked shaped member(s), second prong shaped member(s), second V-shaped member(s), second U-shaped member(s), and/or second H-shaped member(s) (230) and/or second member(s) (316) (Herein all called "Support Member(s)") (425).

Without being limited, the movement and/or transfer of the one or more object(s) 300 from the first one or more member(s) 315 and/or the first one or more retention member(s) 315 and/or the first one or more effectively, shaped, prong shaped, fork shaped, H-shaped, U-shaped and/or V-shaped member(s) 228 and/or a first one or more retaining structure(s) 391, to the second one or more member(s) 316 and/or second one or more retention member(s) 316 and/or the second one or more effectively, shaped, prong shaped, fork shaped, H-shaped, U-shaped and/or V-shaped member(s) 230 and/or a second one or more retaining structure(s) 392, and the movement and/or transfer of the one or more object(s) 300 from the second one or more member(s) 316 and/or second one or more retention member(s) 316 and/or the second one or more effectively, shaped, prong shaped, fork shaped, H-shaped, U-shaped and/or V-shaped member(s) 230 and/or a second one or more retaining structure(s) 392, to the first one or more member(s) 315 and/or the first one or more retention member(s) 315 and/or the first one or more effectively, shaped, prong shaped, fork shaped, H-shaped, U-shaped and/or V-shaped member(s) 228, can be effectively initiated, caused, and/or completed, by the effective movement of the various support gaps 228, 230, 315, 316, support member(s) 425, retention structure(s) 390, first retaining structure(s) 391, and second retaining structure(s) 392, in or with any effective, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s).

Without being limited, the various one or more of any suitable and effective member(s) for effectively, holding, removably holding, supporting, removably supporting, releasing, and/or transferring, the one or more object(s) 300 and/or the various support gaps 228, 230, 315, 316, and support member(s) 425, can be and/or form, one or more of any suitable and effective shape(s) and/or structure(s) such as, but not limited to any, V-shape(s), U-shape(s), H-shape(s), fork shape(s), prong shape(s), concave shape(s), trough shape(s), valley shape(s), wave shape(s), and/or sinusoidal shape(s). Also, without being limited, the one or more of any retention structure(s) 390 can include one or more, or a plurality, of any suitable and effective, valley(s) and/or indentation(s) for effectively retaining, holding, releasing, and/or transferring, the object(s) 300 at one or more of any suitable and effective time(s).

Without being limited, the one or more support member(s) 425 can be directly and/or indirectly connected with one or more of any suitable and effective means for moving the one or more support member(s) 425, known to those skilled in the art such as, but not limited to any, suitable and effective, motor(s) (Herein called "Motor(s)") 215, to cause the said support member(s) 425 to have any suitable and effective, rotation, rotating movement, forward rotating movement, backward rotating movement, lateral movement, clockwise movement, counter-clockwise movement, forward momentum, pivoting forward momentum, rearward momentum, pivoting rearward momentum, angled movement, side to side movement, circular movement, partial circular movement, tangential movement, partial tangential movement, arcing movement, partial arcing movement, pivoting movement, partial pivoting movement, and/or angled upward and/or angled downward movement, and/or angled motion(s) and/or direction(s) of movement(s), and/or motion(s), at any suitable and effective time(s) and for any suitable and effective, duration(s) of time(s), velocity(s), and/or speed(s).

Figure 9:
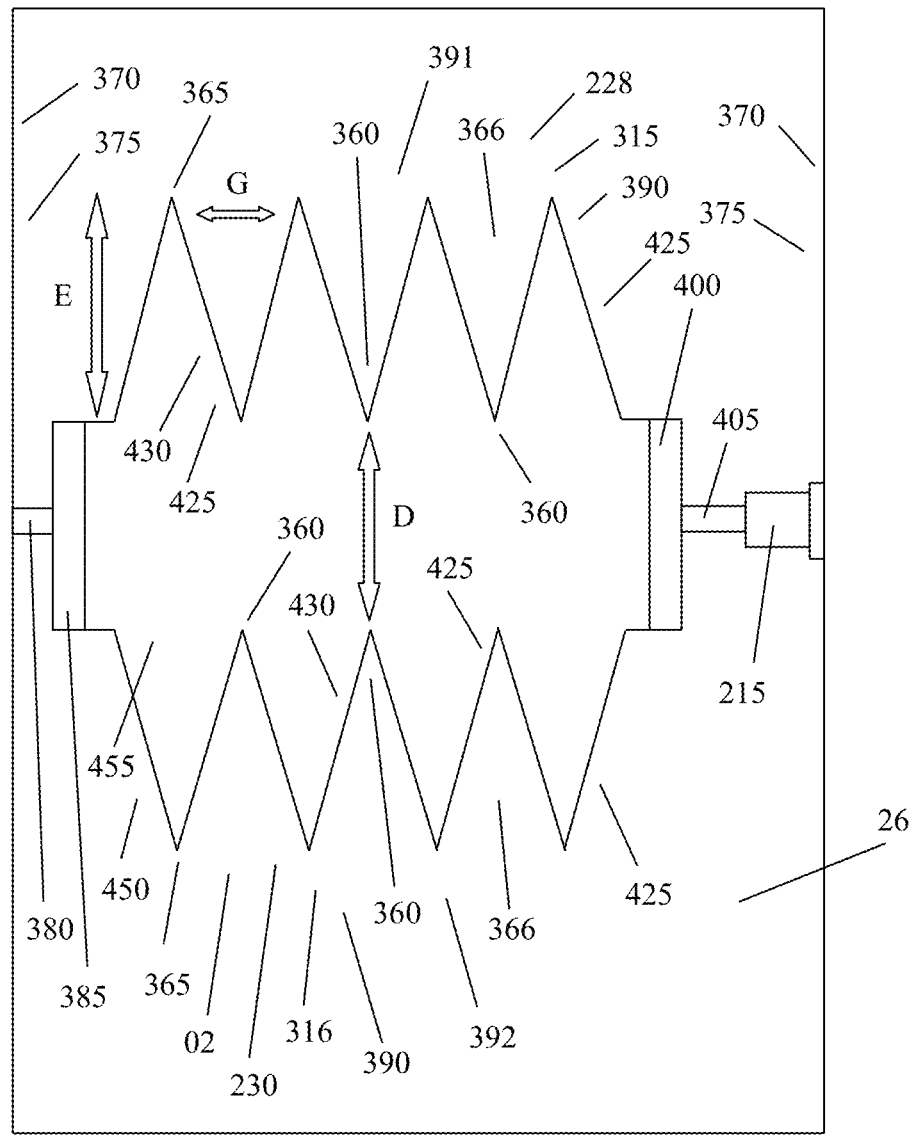
FIG. 9 is a side view of a rotating object(s) holder, located in a treatment chamber, where the various support members that are in contact with the object(s) form a first retaining structure(s) with one or more "V" shape(s), and an opposing second retaining structure(s) with one or more "V" shape(s), and connect with a member shaft interface that interfaces with a drive shaft that connects with a motor. The critical dimensions of the object support gap(s) 366, the critical distances "D", "E", and "G" are shown. The support members forming a "V" shape.

With reference to FIG. 9, and without limitation, one or more of any suitable object(s) 300 support member(s) 425 forms one or more of any suitable and effective retention structure(s) 390, and more specifically and inclusively, and without limitation, a first one or more retaining structure(s) 391 and a second one or more retaining structure(s) 392, and even more specifically, and without limitation, a one or more of any suitable and effective, first V-shaped member(s), first U-shaped member(s), and/or first H-shaped member(s) (228) and/or first member(s) (315), and one or more of any suitable and effective, second V-shaped member(s), second U-shaped member(s), and/or second H-shaped member(s) (230) and/or second member(s) (316). Without being limited, the various support member(s) 425 can effectively connect with at least one member shaft interface(s) 400 that effectively connects with one or more of any suitable motor drive shaft(s) 405, that effectively connects with one or more of any suitable motor(s) 215.

Also, with reference to FIG. 9, and without limitation, the one or more support member(s) 425 can directly and/or indirectly connect to the said motor(s) 215, and can be effectively moved, without being connected to one or more of any, rod(s), tube(s), beams(s), shaft(s), elongated member(s), tubular rod(s), and/or elongated structure(s) 222, support(s), and/or conduit(s), that could first connect with and/or connect to, the motor(s) 215 and/or any connecting drive shaft(s) and/or moving shaft(s). Also without being limited, the one or more support member(s) 425 can form the one or more of any suitable and effective retention structure(s) 390 and/or any effective structure(s) and/or shapes to hold, support, removably hold, and/or removably support, the one or more object(s) 300 within the treatment chamber(s), test chamber(s), and/or sealed treatment chamber(s) (26), and can effectively directly and/or indirectly connect to the one or more motor(s) 215, and more preferably, and without limitation, to one or more of any suitable motor(s) drive shaft(s) 405 that connect to the one or more motor(s) 215.

Without being limited, the one or more support member(s) 425 can connect directly and/or indirectly to the one or more motor(s) 215. It is preferred, without limitation, that the one more more support member(s) 425 first connects with one or more of any suitable and effective connecting part(s) and/or component(s) and/or shaft interface part(s) and/or component(s), and more particularly, and without limitation, one or more of any effective member shaft interface(s) 400, before connecting to the motor(s) 215.

Also, and without being limited, the other one or more end(s) of the one or more support member(s) 425 that is opposite from the motor(s) 215, can optionally directly and/or indirectly connect with one or more of any suitable and effective, bearing(s) and/or turning apparatus(s) known to those skilled in the art, such as, but not limited to any turn support bearing(s) 380, that can preferably, and without limitation, effectively connect with one or more of any suitable and effective, surface(s) and/or structure(s), such as, but not limited to, one or more of any suitable and effective, wall(s), bracket(s), and/or mount point(s). It is preferred, without limitation, that the one or more end(s) of the support member(s) 425 that is opposite from the motor(s) 215, suitable and effectively connects with one or more of any suitable member bearing interface(s) 385, that suitably and effectively connects with one or more turn support bearing(s) 380. However, and without limitation, the other end of the one or more support member(s) 425 that is opposite from the motor(s) 215, can also extend freely into the sealed treatment chamber(s) (26) without being directly and/or indirectly connected to any, part(s), object(s), component(s), and/or surface(s) such as, but not limited to any, wall(s), bracket(s), bearing(s), and/or turn support bearing(s) 380.

Without being limited, the one or more support member(s) 425 can be constructed from any, suitable and effective material(s) such as, but not limited to any, cable(s), wire(s), rod(s), beam(s) conduit(s), tubing(s), elongated structure(s), ceramic structure(s), milled structure(s), stainless steel(s), polymer(s), ceramic(s), glass(s), and/or molded structure(s). It is preferred, without limitation, that the support member(s) 425 are constructed from one or more of any suitable and effective, 316 stainless steel wire(s), wire(s), elongated structure(s), tube(s), conduit(s), wire form(s), and/or rod(s), of any suitable and effective, diameter(s), size(s), length(s), width(s), shape(s), geometry(s), thickness(s), and/or gauge(s), that are also preferably, and without limitation, bent and/or formed into one or more of any suitable and effective shape(s) such as, but not limited to, one or more of any suitable and effective, "V" shape(s), "U" shape(s), pronged shape(s), fork shape(s), and/or "H" shape(s). Without being limited, any of the one or more of any formed shape(s) and/or one or more of any object supporting structure(s) formed by one or more of any member(s) 228,230,315,316,390,391,392,425, can be suitably and effectively, open, solid, partially open, partially solid, and/or hollow, in any space(s) 450 and/or middle location(s) 455 that is formed and/or is present and/or not present, between and/or within these said one or more member(s). It is preferred, without limitation, that the one or more space(s) 450 and/or middle location(s) 455 are hollow and/or open air voids.

Referring to FIG. 9, and without limitation, the one or more object(s) 300 (not shown) can first interface with and/or be held and/or supported by, the first one or more member(s) 315 and/or the first one or more retention member(s) 315 and/or the first one or more of any effectively, shaped, prong shaped, fork shaped, H-shaped, U-shaped, and/or V-shaped, member(s) 228 forming a first one or more retaining structure(s) 391. It is preferred, without limitation, that the first one or more member(s) 315, first one or more effectively, shaped, H-shaped, U-shaped, and/or V-shaped, member(s) 228, and/or first one or more retaining structure(s) 391, are at least pointing in any suitable and effective direction(s) and/or are in any effective orientation(s) and/or angle(s) to effectively hold, support, release, transfer, and/or receive, the object(s) 300 at any suitable and effective time(s).

It is more preferred, without limitation, that the first one or more member(s) 315, first one or more effectively, shaped, prong shaped, fork shaped, H-shaped, U-shaped, and/or V-shaped, member(s) 228, and/or first one or more retaining structure(s) 391 are at least pointing and/or orientated in any effective angle(s) or degree(s) that are within +20 degree and −20 degree from any vertical orientation(s) and/or ninety degree angle(s) and/or orientation(s).

It is even more preferred, without limitation, that the first one or more member(s) 315, first one or more effectively, shaped, prong shaped, fork shaped, H-shaped, U-shaped, and/or V-shaped, member(s) 228, and/or first one or more retaining structure(s) 391 are at at least pointing and/or orientated effectively upward.

It is very preferred, without limitation, that the first one or more first member(s) 315 and retention member(s) 315, first one or more effectively, shaped, prong shaped, fork shaped, H-shaped, U-shaped, and/or V-shaped, member(s) 228, and/or first one or more retaining structure(s) 391 are at at least pointing and/or oriented effectively near, about, and/or at, any effective vertical or around any effective vertical orientation(s) and/or direction(s).

Without being limited, a second one or more member(s) 316 and/or second one or more retention member(s) 316 and/or the second one or more effectively, shaped, prong shaped, fork shaped, H-shaped, U-shaped and/or V-shaped, member(s) 230 forming a second one or more retaining structure(s) 392, are preferably, and without limitation, pointed and/or oriented in any suitable and effective direction(s) and/or orientation(s), to suitably and effectively, receive, hold, support, release, and/or transfer, the object(s) 300 at any suitable and effective time(s), such as, but not limited to, when the object(s) 300 are held, supported, treated, processed, and/or released, as well as moved and transferred back and forth from or between, the first one or more member(s) 315 and/or the first one or more retention member(s) 315 and/or the first one or more effectively, shaped, prong shaped, fork shaped, H-shaped, U-shaped and/or V-shaped member(s) 228 and/or a first one or more retaining structure(s) 391, and the second one or more member(s) 316 and/or second one or more retention member(s) 316 and/or the second one or more effectively, shaped, prong shaped, fork shaped, H-shaped, U-shaped and/or V-shaped member(s) 230 and/or a second one or more retaining structure(s) 392.

It is more preferred, without limitation, that the second one or more member(s) 316 and retaining member(s) 316, second one or more effectively, shaped, prong shaped, fork shaped, H-shaped, U-shaped and/or V-shaped member(s) 230, and/or second one or more retaining structure(s) 392 are at least pointed and/or orientated in any effective, angle(s), orientation(s), direction(s), and/or degree(s), so that when they are moved, rotated, and/or oriented to any upward orientation(s), or ceiling oriented orientation(s), they are within +20 degree and −20 degree from any vertical orientation(s) and/or ninety degree angle(s) and/or orientation(s).

It is even more preferred, without limitation, that the second one or more member(s) 316, second one or more effectively, shaped, prong shaped, fork shaped, H-shaped, U-shaped and/or V-shaped member(s) 230, and/or second one or more retaining structure(s) 392 are pointed and/or orientated in one or more of any effective, direction(s), angle(s), degree(s), and/or orientation(s), that is about opposite and/or opposite from the first one or more member(s) 315, first one or more effectively, shaped, prong shaped, fork shaped, H-shaped, U-shaped and/or V-shaped member(s) 228, and/or first one or more retaining structure(s) 391.

Without being limited, the first one or more member(s) 315, first one or more effectively, shaped, prong shaped, fork shaped, H-shaped, U-shaped and/or V-shaped member(s) 228, and/or first one or more retaining structure(s) 391, and the second one or more member(s) 316, second one or more effectively, shaped, prong shaped, fork shaped, H-shaped, U-shaped and/or V-shaped member(s) 230, and/or second one or more retaining structure(s) 392, are located suitably and effectively within the sealed treatment chamber(s) (26).

Without being limited, the the first one or more member(s) 315, first one or more effectively, shaped, prong shaped, fork shaped, H-shaped, U-shaped and/or V-shaped member(s) 228, and/or first one or more retaining structure(s) 391, and the second one or more member(s) 316, second one or more effectively, shaped, prong shaped, fork shaped, H-shaped, U-shaped and/or V-shaped member(s) 230, and/or second one or more retaining structure(s) 392, effectively connect to one or more of any suitable and effective member shaft interface(s) 400, and the member shaft interface(s) 400 effectively connect with one or more suitable motor drive shaft(s) 405 that effectively connects with one or more suitable motor(s) 215. Without being limited, the motor(s) 215 can be mounted to, interfaced with, and/or be effectively connected to, one or more of any suitable and effective surface(s), structure(s), and/or component(s) such as, but not limited to any, bulkhead(s), beam(s), mounting surface(s), wall(s), mounting bracket(s), and/or bracket(s) (Herein called "Wall(s)" 370 or "Bracket(s)" 375.

Without being limited, any suitable and effective end(s) of the first one or more member(s) 315, first one or more effectively, shaped, prong shaped, fork shaped, H-shaped, U-shaped and/or V-shaped member(s) 228, and/or first one or more retaining structure(s) 391, and the second one or more member(s) 316, second one or more effectively, shaped, prong shaped, fork shaped, H-shaped, U-shaped and/or V-shaped member(s) 230, and/or second one or more retaining structure(s) 392, that is opposite from the motor(s) 215, can directly and/or indirectly connect with one or more of any suitable and effective apparatus(s) and/or component(s) known to those skilled in the art, that can turn and/or rotate such as, but not limited to any suitable and effective, bearing(s) 380, however, and without limitation, they can also effectively terminate in free space within the sealed treatment chamber(s) (26), and not directly and/or indirectly connect or interface with any other part(s) and/or component(s) such as, but not limited to any, bearing(s) 380. However, it it preferred, without limitation, that they instead effectively directly and/or indirectly connect to or with, one or more of any suitable and effective member bearing interface(s) 385, and the member bearing interface(s) 385 can suitably and effectively connect with one or more of any suitable and effective bearing(s) and/or turn support bearing(s) 380, where the turn support bearing(s) 380 can be mounted to, interfaced with, and/or be effectively connected to, one or more of any suitable and effective surface(s), structure(s), and/or component(s) such as, but not limited to any, wall(s) 370 or bracket(s) 375.

Figure 10:
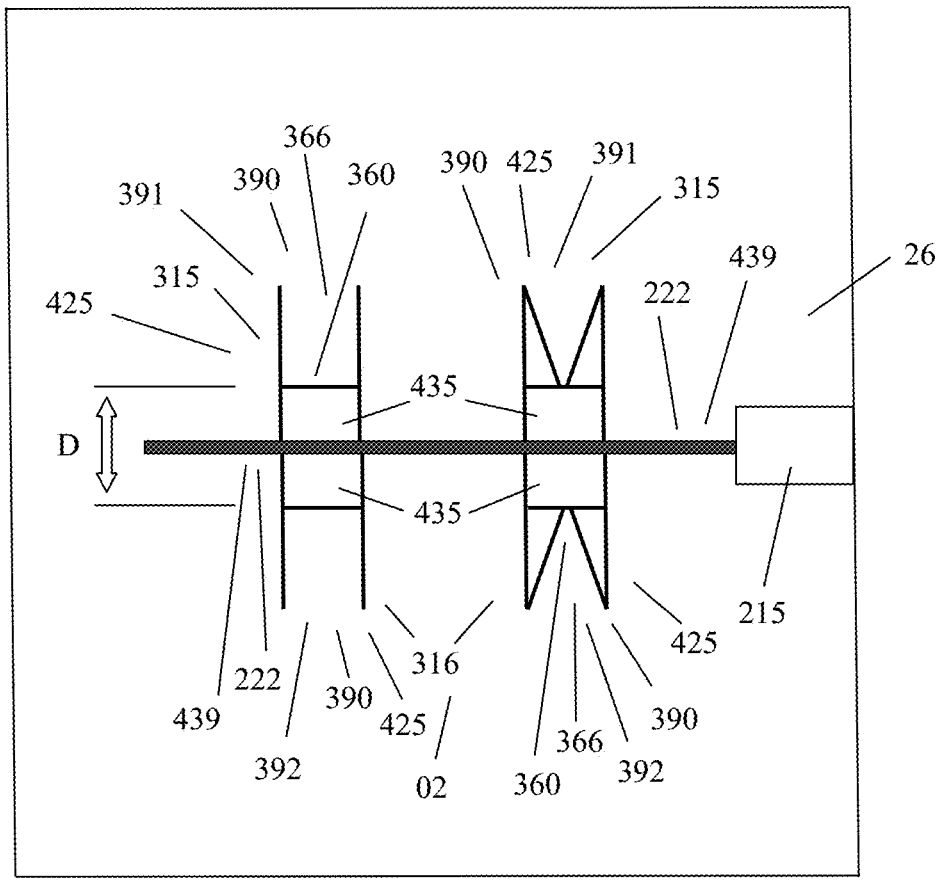
FIG. 10 is a side view of a rotating object(s) holder, located in a treatment chamber, where the various support members that are in contact with the object(s) form a first retaining structure(s) and an opposing second retaining structure(s), and where each of these retaining structure(s) first connects with an effective spacer of an effective distance from the motor drive shaft that positions the base of each retaining structure(s) at an effective distance from the base of each opposing retaining structure. The retaining structures and their spacers connect with the motor drive shaft that turns them for one or more of any effective distance(s). The critical distance from each support base is shown by dimension "D".
Figure 11:
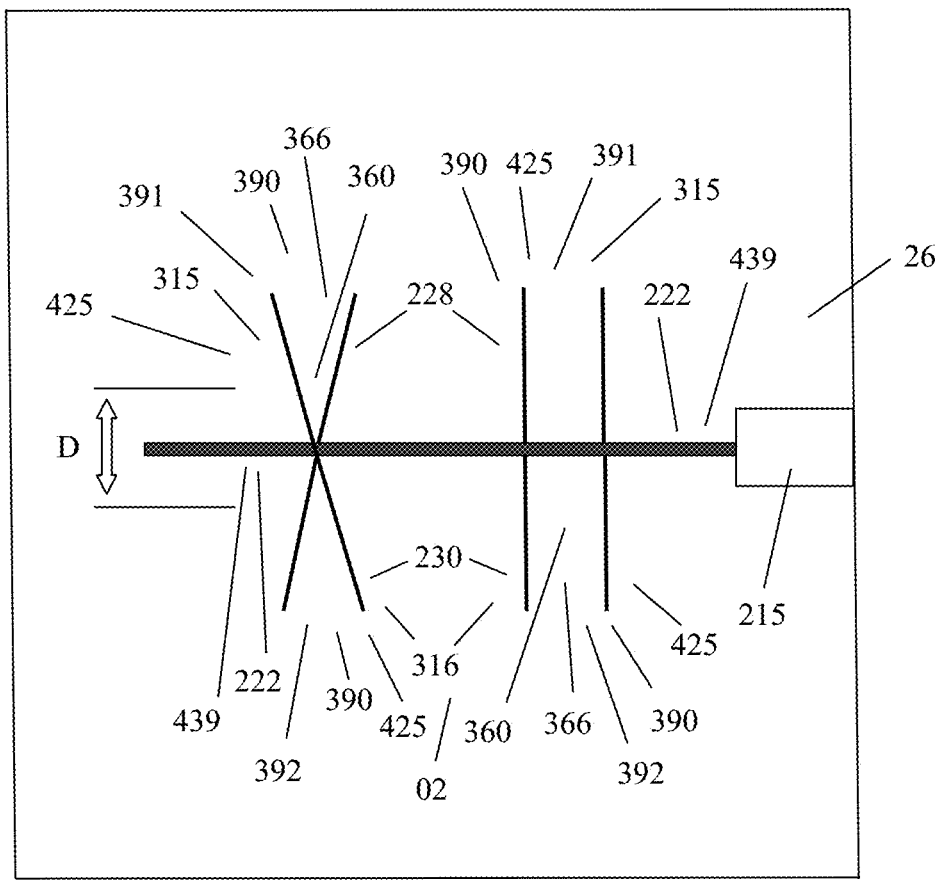
FIG. 11 is a side view of a rotating object(s) holder, located in a treatment chamber, where the various support members that are in contact with the object(s) form a plurality of first retaining structure(s) and an opposing plurality of second retaining structure(s), and where each of these retaining structure(s) connects with the drive shaft that turns them for one or more of any effective distance(s). The critical distance from each support base is shown by dimension "D".

Referring to FIG. 10-11, and without limitation, the first one or more member(s) 315 and retaining member(s) 315, first one or more effectively, shaped, prong shaped, fork shaped, H-shaped, U-shaped and/or V-shaped member(s) 228, and/or first one or more retaining structure(s) 391, and the second one or more member(s) 316 and retaining member(s) 316, second one or more effectively, shaped, prong shaped, fork shaped, H-shaped, U-shaped and/or V-shaped member(s) 230, and/or second one or more retaining structure(s) 392, can also suitably and effectively, connect to, mount to, and/or attach to, one or more of any suitable and effective means that can suitably and effectively, move, pivot, turn, and/or rotate, the first one or more member(s) and retaining member(s) 315 and/or first one or more retaining structure(s) 391, and the second one or more member(s) and retaining member(s) 316 and/or second one or more retaining structure(s) 392, such as, but not limited to any suitable and effective, rod(s), shaft(s), drive shaft(s), member(s), pipe(s), tube(s), conduit(s), beam(s), and/or elongated structure(s) (Herein called "Elongated Structure(s)") 222.

Also, and without being limited, the one or more elongated structure(s) 222 can directly and/or indirectly connect with one or more of any suitable and effective means to suitably and effectively, move, pivot, turn, and/or rotate, the elongated structure(s) 222, such as, but not limited to any motor(s) 215, at any suitable and effective time(s), all in a manner known to those skilled in the art.

Without being limited, the end of the elongated structure(s) 222 that is opposite from the motor(s) 215, can also, and without limitation, terminate in any free space within the sealed treatment chamber(s) (26), and not connect or interface with any other part(s) and/or component(s) such as, but not limited to any bearing(s) 380. However, it is preferred, without limitation, that the end(s) of the one or more elongated structure(s) 222 that is opposite of any motor(s) 215, suitably and effectively connect with one or more of any suitable and effective, turning and/or motion apparatus(s) known to those skilled in the art, bearing(s), and/or turn support bearing(s) 380, where these apparatus(s) and/or turn support bearing(s) 380 can be mounted to, interfaced with, and/or be effectively connected to, one or more of any suitable and effective surface(s), structure(s), and/or component(s) such as, but not limited to any, wall(s) 370 or bracket(s) 375.

Referring to FIG. 10, and without limitation, the first retaining structure(s) (391) and second retaining structure(s) (392) are "U-shaped". Referring to FIG. 11, and without limitation, the first retaining structure(s) (391) and second retaining structure(s) (392) are constructed from one or more of any suitable and effective shaped member(s) such as, but not limited to any, prong shaped, fork shaped, H-shaped, U-shaped, and/or V-shaped, member(s).

Figure 5:
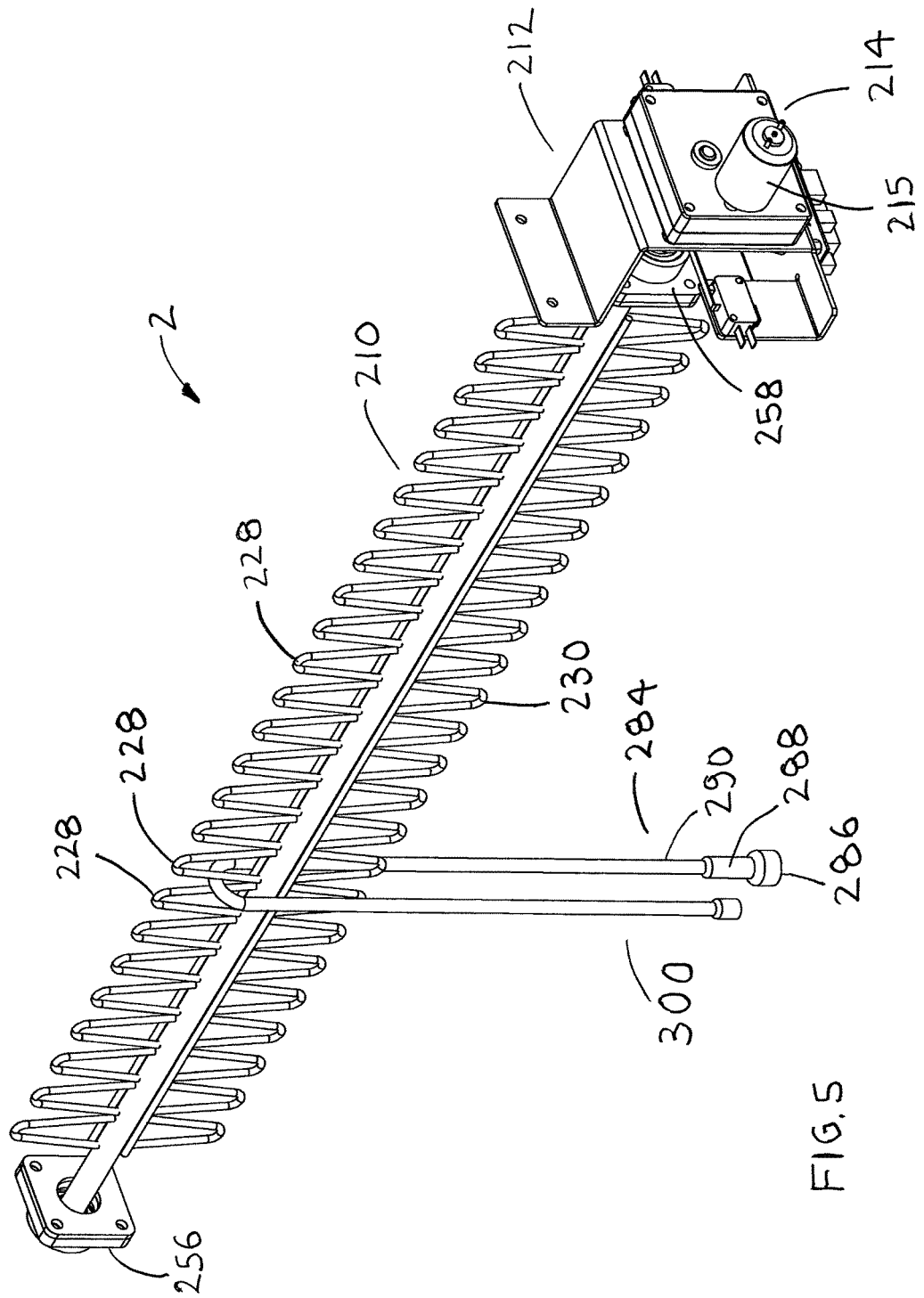
FIG. 5 is a perspective view of a rotating cable holder in accordance with the present invention.
Figure 6:
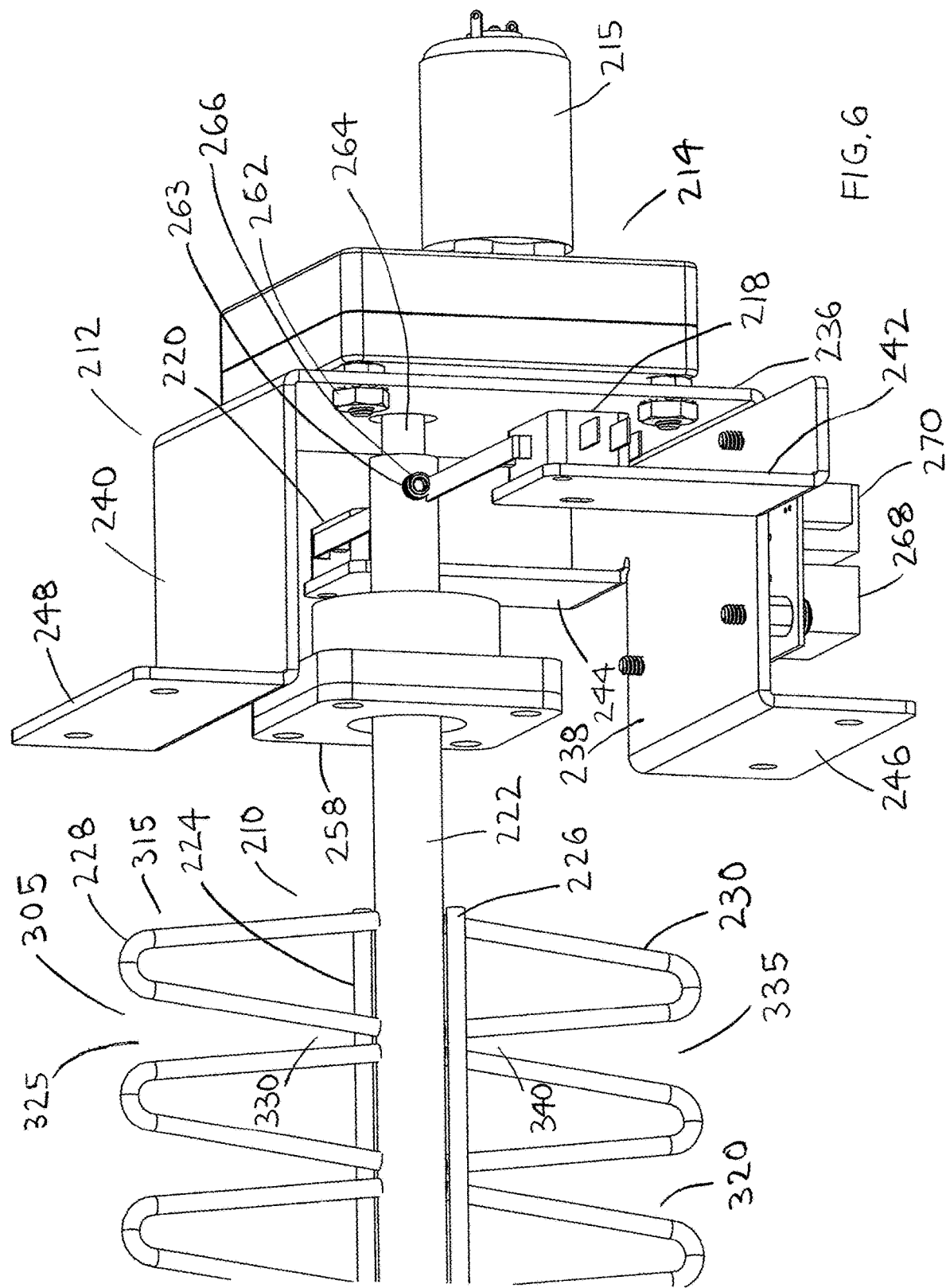
FIG. 6 is an enlarged perspective view of a mounting bracket of a rotating cable holder in accordance with the present invention.
Figure 7:
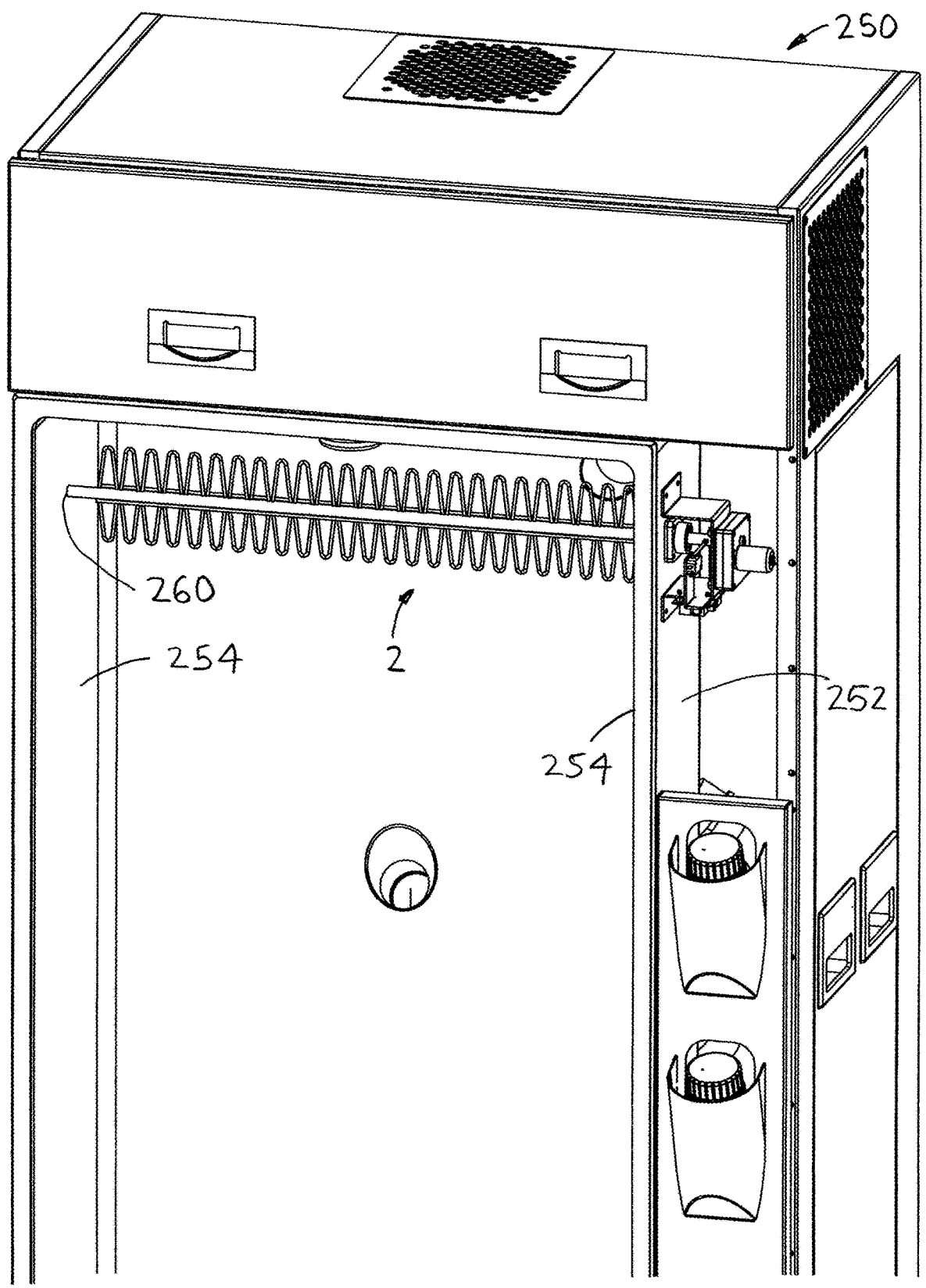
FIG. 7 is a perspective view of a rotating cable holder mounted in a disinfection chamber of a disinfection cabinet in accordance with the present invention.

Referring generally to FIGS. 5-7, and more specifically to FIGS. 9-11, and FIGS. 12-14, and without being limited, the one or more first member(s) 315 and/or first retaining member(s) 315, and the second member(s) 316 and/or second retaining member(s) 316, form the first one or more retaining structure(s) 391 and the second one or more retaining structure(s) 392, by forming one or more of any suitable and effective shape(s) and/or structure(s) for holding, supporting, releasing, and/or transferring, the one or more object(s) 300 such as, but not limited to any, "V" shape(s), "H" shape(s), "U" shape(s), prong shape(s), "L" shape(s), fork shape(s), sinusoidal shape(s), and/or square wave shape(s). Without being limited, the various shapes of the first one or more retaining structure(s) 391 and the second one or more retaining structure(s) 392, can have one or more of any suitable and effective, height(s) and/or depth(s), distance(s) between the one or more object support base(s) 360 and the one or more support geometry top(s) 365 (as represented by dimension "E"), width(s) (as represented by dimension "G"), angle(s), and/or angle(s) between the between the one or more object support base(s) 360 and the one or more support geometry top(s) 365, as shown in FIG. 9.

Without being limited, these various dimension(s) and/or distance(s) can be controlled, impacted, and/or effected, by any related variables such as, but not limited to any, size(s), shape(s), geometry(s), dimension(s), diameter(s), travel distance(s) of any member(s) 425,315,316,228,230, width(s), mass or weight(s), and/or length(s), of one or more of any treated object(s) 300.

Without being limited, the first one or more retaining structure(s) 391 and the second one or more retaining structure(s) 392 can have one or more of any suitable and effective, area(s), groove(s), channel(s), space(s), indentation(s), valley(s), trench(s), gap(s), holding space(s), holding area(s), supporting area(s), supporting space(s), retaining space(s), and/or retaining area(s) (Herein called "Object Support Gap(s)") 366, for the one or more treated and processed object(s) 300. It is preferred, without limitation, that each object support gap(s) 366 for both the first one or more retaining structure(s) 391 and the second one or more retaining structure(s) 392, only interfaces with one object 300 during all of the various surface treatment(s) and processing step(s) that can take place in the sealed treatment chamber(s) 26. Without being limited, this can prevent more than one object(s) 300 from resting upon and/or interfacing with another object 300 within the same object support gap(s) 366, and causing various anomalies and/or nonconformances to occur such as, but not limited to any, shadowed surface(s), untreated surface(s), unprocessed surface(s), and/or undried surface(s), to occur and/or result.

Without being limited, each of the one or more object support gap(s) 366 can also have one or more, but preferably, and without limitation, just one, suitable and effective object support base(s) 360. Also, and without being limited, the object support base(s) 360 can be continuous and effectively connect to and/or with the various wall(s) and/or structure(s) that are used to construct the object support gap(s) 366.

Without being limited, the object support base(s) 360 can also be non-continuous and not connect to and/or with one or more various wall(s) and/or structure(s) that forms the object support gap(s) 366, and/or they can be non-continuous and only effectively connect with one of the various wall(s) and/or structure(s) that forms the object support gap(s) 366.

Without being limited, the object support base(s) 360 can continuously connect one wall of the object support gap(s) 366 to another wall of the object support gap(s) 366. Alternatively, and without limitation, the object support base(s) 360 can have one or more gap(s) in their construction at one or more of any suitable and effective location(s), including, but not limited to, in or about the middle of the object support base(s) 360 (not shown).

Also, without being limited, the one or more object support base(s) 360 and/or one or more of any wall(s) 430 that form the object support gap(s) 366, can have one or more of any suitable and effective purpose(s) and function(s) such as, but not limited to, the object(s) 300 can suitably and effectively, rest on, rest partially on, interface with, partially interface with, be supported by, and/or can be partially supported by, the wall(s) 430 and/or object support base(s) 360, when either the first one or more retaining structure(s) 391 and/or the second one or more retaining structure(s) 392 are in any effective, upward, about upward, upward angled, ceiling facing, about ceiling facing, direction(s), angle(s), and/or orientation(s). Without being limited, the object support base(s) 360 can also act as structural support(s) to or for the one or more wall(s) 430 that can form the object support gap(s) 366. Without being limited, the object support base(s) 360 can have any suitable and effective design(s), construction(s), and attribute(s) such as, but not limited to any suitable and effective, length(s), angle(s), width(s), perforation(s), texture(s), angle(s), geometry(s), and/or curvature(s).

Without being limited, the object support base(s) 360 can also help to form or be any effective part of the structure(s) of the object support gap(s) 366. It is preferred, without limitation, that the one or more object support base(s) 360 are formed by and/or constructed with one or more of any first member(s) 315 and/or first retaining member(s) 315, and any of the second member(s) 316 and/or second retaining member(s) 316.

Without being limited, one or more of any suitable and effective distance(s) can exist between the object support gap(s) 366 that are a part of the first one or more retaining structure(s) 391 and the object support gap(s) 366 that are a part of the second one or more retaining structure(s) 392. It is preferred, without limitation, that the object support base(s) 360 that are a part of the first one or more retaining structure(s) 391 and the object support base(s) 360 that are a part of the second one or more retaining structure(s) 392, are separated by one or more of any suitable and effective distance(s) (as represented by dimension "D"). Without being limited, these various dimension(s) and/or distance(s) can be controlled, impacted, and/or effected, by any related variables such as, but not limited to any, size(s), diameter(s), shape(s), dimension(s), width(s), geometry(s), mass or weight(s), travel distance(s) of any member(s) 425,315,316, 228,230, and/or length(s), of any treated object(s) 300.

Also referring to FIGS. 9-11, and without being limited, the object support gap(s) 366 and the object support base(s) 360 of the first one or more retaining structure(s) 391 can be suitably and effectively separated from the object support gap(s) 366 and the object support base(s) 360 of the second one or more retaining structure(s) 392, using one or more of any suitable and effective means such as, but not limited to any, spacer(s) (Herein called "Support Spacer(s)") 435 and/or the effective design, construction, and spacing, of the various parts of the first retaining structure(s) 391 and second retaining structure(s) 392.

Referring to FIGS. 10-11, and without limitation, one or more of any suitable and effective, first one or more member(s) 315 and first one or more retaining structure(s) 391, and second one or more member(s) 316 and second one or more retaining structure(s) 392, are preferably, but without limitation, suitably and effectively connected to one or more of any suitable and effective support spacer(s) 435, that are suitably and effectively connected to one or more of any suitable and effective, rod(s), pipe(s), tube(s), conduit(s), elongated member(s), beam(s), elongated support structure(s), and/or shaft(s) (Herein called "Motor Drive Shaft(s)" 439. Without being limited, the one or more motor drive shaft(s) 439 connect to one or more suitable and effective motor(s) 215 that can suitably and effectively, rotate, turn, pivot, and/or move, the first one or more member(s) 315 and first one or more retaining structure(s) 391, and second one or more member(s) 316 and second one or more retaining structure(s) 392, at one or more of any suitable and effective time(s) to effectively, treat, process, and/or dry, the various surface(s) of the one or more object(s) 300.

Figure 12:
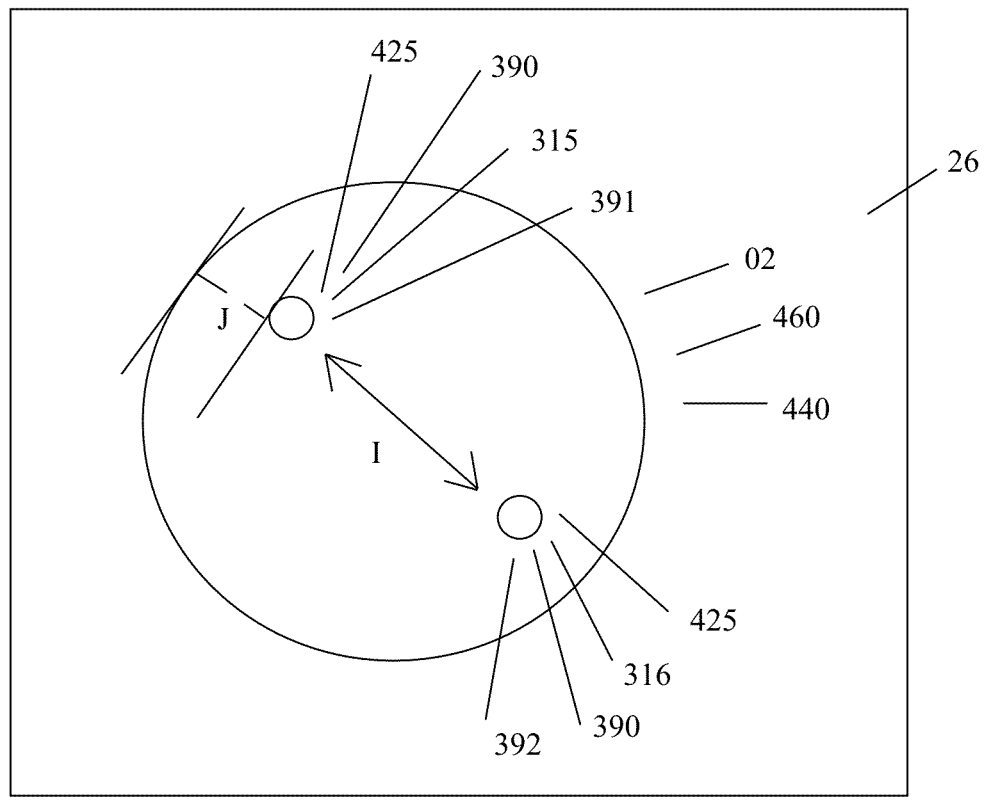
FIG. 12 is a front view of a rotating object(s) holder, located in a treatment chamber, where the various support members that are in contact with the object(s) form a plurality of first retaining structure(s) and an opposing plurality of second retaining structure(s), and where each of these retaining structure(s) connects with at least one rotating mount plate(s), that is turned, pivoted, and/or rotated by at least one motor (not shown). Critical dimensions J and I are shown.
Figure 13:
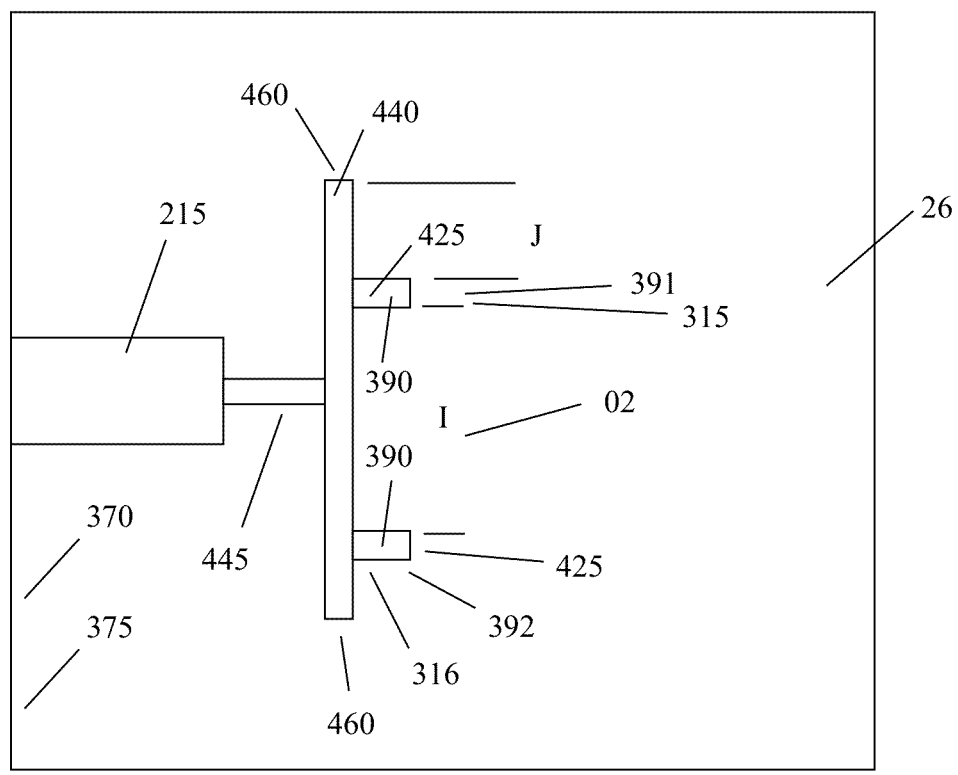
FIG. 13 is a side view of a rotating object(s) holder, located in a treatment chamber, where the various support members that are in contact with the object(s) form a plurality of first retaining structure(s) and an opposing plurality of second retaining structure(s), and where each of these retaining structure(s) connects with at least one rotating mount plate(s) that connects with at least one motor drive shaft that connects with at least one motor(s). Critical dimensions J and I are shown.
Figure 14:
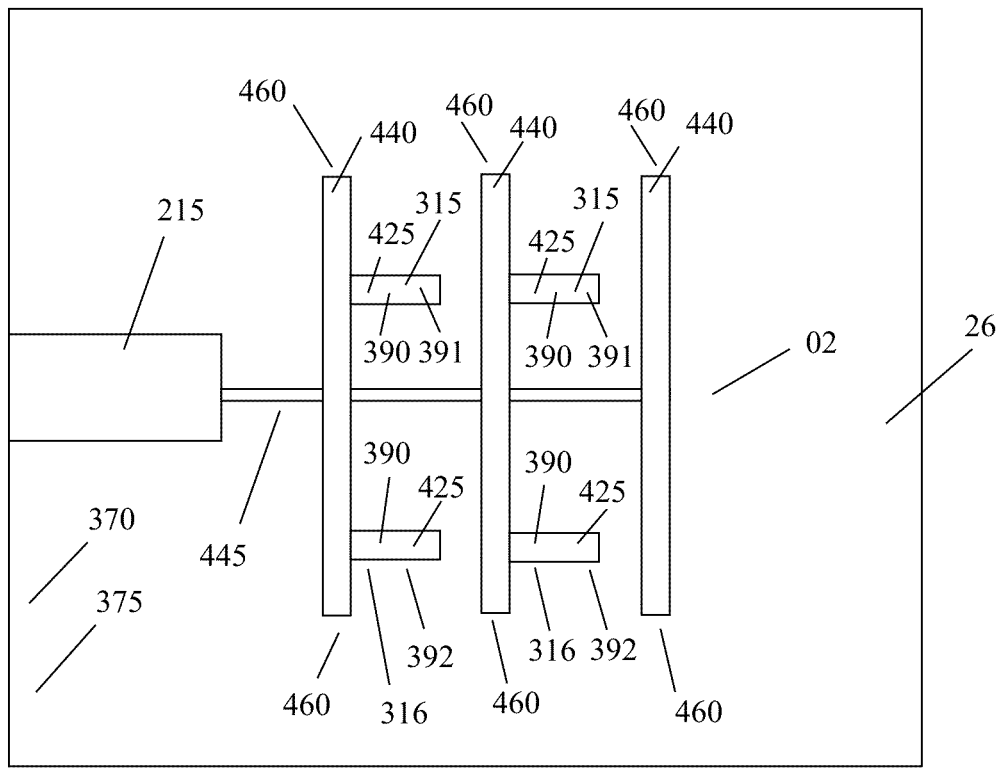
FIG. 14 is a side view of a rotating object(s) holder, located in a treatment chamber, that is designed to treat one or more object(s), where the various support members that are in contact with the object(s) form a plurality of first retaining structure(s) and an opposing plurality of second retaining structure(s), and where each of these retaining structure(s) connects with a plurality of rotating mount plate(s) that connects with at least one motor drive shaft that connects with at least one motor(s). Critical dimensions J and I are shown.

Referring to FIG. 12-14, and without limitation, another variation for moving, pivoting, turning, and/or rotating, a first one or more member(s) 315 and/or first one or more retaining structure(s) 391, and a second one or more member(s) 316 and/or second one or more retaining structure(s) 392, for treating, processing, and/or drying, the various surface(s) of the one or more object(s) that are effectively located within the sealed treatment chamber(s) 26, is described.

Without being limited, a first one or more member(s) 315 and/or a first one or more retaining structure(s) 391, and a second one or more member(s) 316 and/or a second one or more retaining structure(s) 392 is located with, attached to, connected to, mounted to, removably attached to, and/or interfaced with, one or more of any suitable and effective, surface(s), part(s), component(s), preferably and without limitation, one or more of any suitable and effective disk(s), and/or plate(s) (Herein called "Rotating Mount Plate(s)") 440, that can suitably and effectively, move, turn, pivot, and/or rotate, at one or more of any suitable and effective time(s). Without being limited, the rotating mount plate(s) 440 can be any suitable and effective, shape(s), geometry(s), diameter(s), length(s), width(s), height(s), thickness(s), and/or size(s).

Also without being limited, the one or more of any member(s) 425,315,316,228,230, and/or retention structure(s) 390, can suitable and effectively, interface with, connect with, mount to, and/or protrude from, the one or more rotating mount plate(s) 440 at any suitable and effective location(s) and/or distance(s) from the one or more outer edge(s) 460 of the rotating mount plate(s) 440 (as represented by dimension "J").

Without being limited, one or more of any suitable and effective distance(s) between the one or more outer edge(s) 460 of the rotating mount plate(s) 440 and the one or more of any member(s) 425,315,316,228,230, and/or retention structure(s) 390, as shown and represented by dimension "J", and the resulting object facing surface(s) of the rotating mount plate(s) 440, can help to maintain any effective contact between the object(s) 300 and their various assigned member(s) 425,315,316,228,230, and/or retention structure(s) 390, that hold, support, move, and/or transfer, the object(s) 300, and can, without limitation, act as any suitable and effective means to channel and/or direct the treated, processed, moved and/or transferred, object(s) 300 into their intended location(s) and/or position(s) at one or more of any suitable and effective time(s). Without being limited, this can also be effective and useful when multiple rotating mount plate(s) 440 are effectively interfaced and/or interconnected together.

According to FIG. 14, and without being limited, one or more, or a plurality, of any suitable and effective rotating mount plate(s) 440 can effectively directly and/or indirectly connect and/or interface with, one or more of any suitable and effective, drive shaft(s) 445 and/or any suitable member(s), elongated member(s), and/or elongated structure(s), that can directly and/or indirectly connect with one or more of any suitable and effective motor(s) 215. It is preferred, without limitation, that the one or more, and/or plurality of, any rotating mount plate(s) 440 can be suitably and effectively spaced and interconnected with one or more of any suitable and shared, drive shaft(s) 445 and/or any suitable member(s), elongated member(s), and/or elongated structure(s), that can directly and/or indirectly connect with one or more of any motor(s) 215.

Without being limited, a first one or more member(s) 315 and/or a first one or more retaining structure(s) 391, and a second one or more member(s) 316 and/or a second one or more retaining structure(s) 392 can be located and/or separated by one or more of any suitable and effective distance(s) (as represented by dimension "I"). Without being limited, these various dimension(s) and/or distance(s) can be controlled, impacted, and/or effected, by any related variables such as, but not limited to any, size(s), diameter(s), geometry(s), shape(s), dimension(s), width(s), mass or weight(s), travel distance(s) of any member(s) 425,315,316,228,230, and/or length(s), of any treated object(s) 300.

Without being limited, the various member(s) 315,316,425 and retaining structure(s) 391,392, can be one or more of any suitable and effective, length(s), shape(s), geometry(s), complex geometry(s), diameter(s), width(s), texture(s), and/or height(s), and can be suitably and effectively, attached to, connected to, mounted to, removably attached to, and/or interfaced with, one or more of any suitable and effective, rotating mount plate(s) 440 at any suitable and effective, location(s), position(s), tangent(s), angle(s), perpendicular position(s), and/or orientation(s).

Without being limited, the various member(s) 315,316,425 and retaining structure(s) 391,392, and any of their connected part(s) and component(s), can effectively extend outward for one or more of any suitable and effective distance(s) from the rotating mount plate(s) 440. Also, and without being limited, one or more of any suitable and effective shape(s) created by the said member(s) can extend out and/or be extended from the one or more rotating mount plate(s) 440, for one or more of any suitable and effective distance(s).

Without being limited, the rotating mount plate(s) 440, various member(s) 315,316,425, and retaining structure(s) 391,392, can have any suitable and effective, rotation, rotating, partial rotating, forward rotating, backward rotating, turning, lateral, clockwise, counter-clockwise, forward rotation, side rotation, forward momentum, rearward momentum, pivoting rearward momentum, angled, side to side, circular, partial circular, tangential, partial tangential, arcing, partial arcing, pivoting, partial pivoting, and/or angled upward and/or angled downward, motion(s), movement(s), and/or angled motion(s) and/or direction(s) of movement(s), at one or more of any suitable and effective velocity(s) and/or speed(s).

It is preferred without limitation, that the at least one first one or more member(s) 315 and/or a first one or more retaining structure(s) 391, and the at least one second one or more member(s) 316 and/or a second one or more retaining structure(s) 392, that effectively interfaces with, holds, supports, releases, and/or transfers, the one or more object(s) 300, is located and/or mounted suitably and effectively perpendicular to the one or more mount plate(s) 440, at one or more of any suitable and effective location(s) on and/or to the rotating mount plate(s) 440.

It is more preferred, without limitation, that the at least one first one or more member(s) 315 and/or a first one or more retaining structure(s) 391, and the at least one second one or more member(s) 316 and/or a second one or more retaining structure(s) 392, are located effectively about opposed to each other.

It is even more preferred, without limitation, that the at least one first one or more member(s) 315 and/or a first one or more retaining structure(s) 391, and the at least one second one or more member(s) 316 and/or a second one or more retaining structure(s) 392, are located effectively at one or more of any suitable and effective offset location(s) to and/or from one another, and the said various member(s) 425,391,315,392,316 can be located at one or more of any suitable and effective distance(s) and/or angle(s) from each other.

Also referring to FIG. 13, and without limitation, the one or more rotating mount plate(s) 440 can be suitably and effectively connected to one or more of any elongated member(s) and/or suitable drive shaft(s) 445 that can be directly and/or indirectly connected to one or more of any suitable and effective motor(s) 215.

With reference to FIGS. 9-15, and without limitation, the one or more of any suitable and effective motor(s) 215 can be suitably and effectively located at one or more of any suitable and effective location(s) inside and/or outside of the sealed treatment chamber(s) 26. Also, without being limited, any of the one or more motor(s) 215 located outside of the sealed treatment chamber(s) 26 can suitably and effectively, connect with, communicate with, and/or drive, one or more of any suitable and effective means to, hold, support, move, pivot, rotate, and/or transfer (2) (390)(391)(392), the one or more object(s) 300, that are located within the the sealed treatment chamber(s) 26, all in a manner known to those skilled in the art.

Referring to FIG. 9, and without limitation, the first one or more member(s) 315 and retaining member(s) 315, first one or more effectively, shaped, prong shaped, fork shaped, H-shaped, U-shaped and/or V-shaped member(s) 228, and/or first one or more retaining structure(s) 391, and the second one or more member(s) 316 and retaining member(s) 316, second one or more effectively, shaped, prong shaped, fork shaped, H-shaped, U-shaped and/or V-shaped member(s) 230, and/or second one or more retaining structure(s) 392, can also suitably and effectively, connect to, mount to, and/or attach to, directly and/or indirectly, one or more of any suitable and effective means that can suitably and effectively, move, pivot, turn, and/or rotate, the first one or more member(s) and retaining member(s) 315 and/or first one or more retaining structure(s) 391, and the second one or more member(s) and retaining member(s) 316 and/or second one or more retaining structure(s) 392, such as, but not limited to one or more of any suitable and effective, motor(s) 215.

Without being limited, the member shaft interface(s) 400 can also be eliminated from the assembly, and the various support gaps 228, 230, 315, 316, support member(s) 425, retention structure(s) 390, first retaining structure(s) 391, and second retaining structure(s) 392, can suitable and effectively, directly and/or indirectly connect and/or interface with, one or more of any suitable and effective, rod(s), shaft(s), member(s), pipe(s), tube(s), elongated member(s), conduit(s), beam(s), elongated structure(s), and/or drive shaft(s) (Herein called "Motor Drive Shaft(s)") 405.

Figure 15:
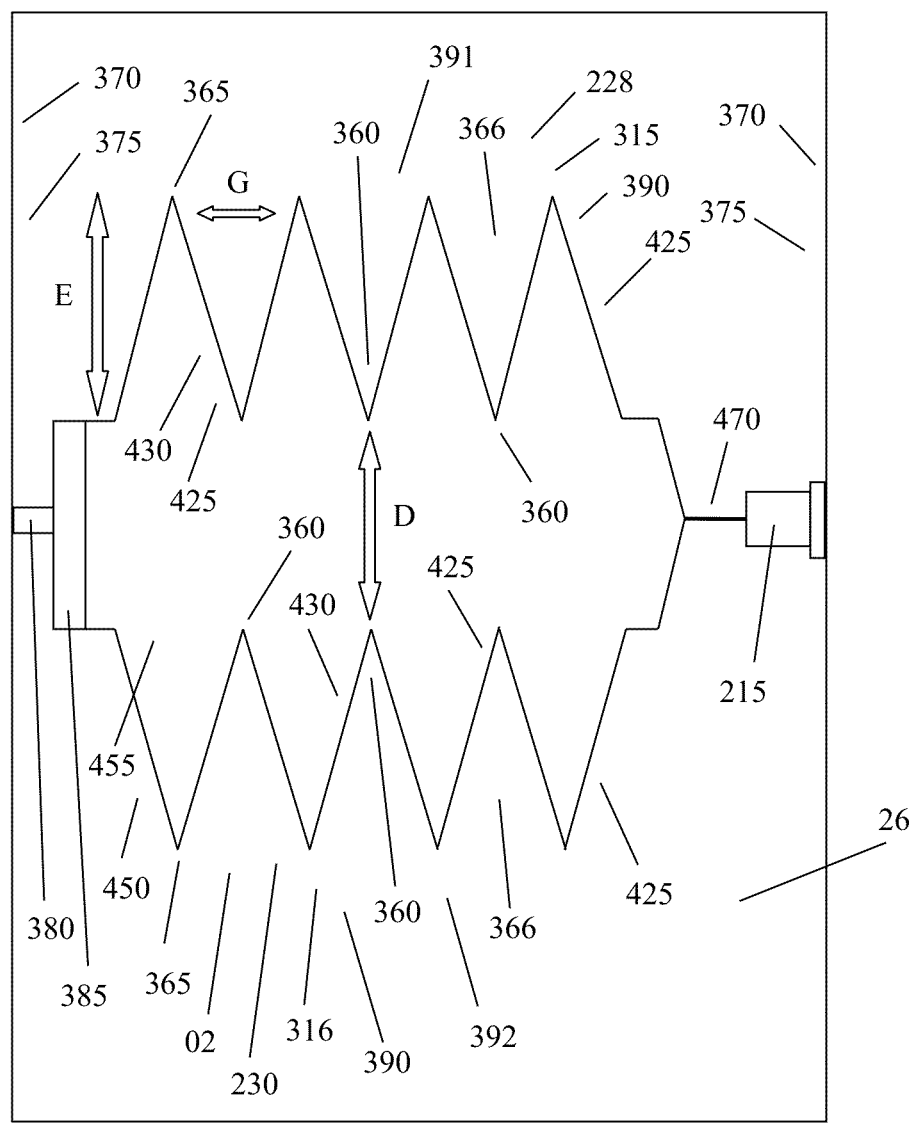
FIG. 15 is a side view of a rotating object(s) holder, located in a treatment chamber, where the various support members that are in contact with the object(s) form a first retaining structure(s) with one or more of any wave shape(s), and an opposing second retaining structure(s) with one or more of any wave shape(s), and where at one end, the various one or more or plurality of members, converge or connect to form at least one shaft(s) and/or elongated member(s) that suitably connects with at least one motor(s).

Also, referring to FIG. 15, and without being limited, the various one or more, or plurality of any, support gaps 228, 230, 315, 316, support member(s) 425, retention structure(s) 390, first retaining structure(s) 391, and second retaining structure(s) 392, can suitable and effectively, converge, merge, interconnect, connect, communicate, fuse, and/or form, at one or more of any suitable end(s), one or more of any suitable and effective, motor drive shaft(s) 405 and/or elongated structure(s) 222 (Herein called "Member Formed Shaft(s)") 470, that can suitably and effectively directly and/or indirectly interface and/or connect with one or more of any suitable motor(s) 215.

Without being limited, the one or more of any of the various retention member(s) 228, 230, 315, 316, support member(s) 425, first retaining structure(s) 391, and second retaining structure(s) 392, can form the various one or more of any suitable and effective retention structure(s) (Herein called "Retention Structure(s)" (390).

Without being limited, the one or more of any of the various, cable tube(s) and/or rod(s), tubular rod(s), member(s), support(s), beam(s), rod(s), shaft(s), member(s), pipe(s), tube(s), conduit(s), elongated structure(s), drive shaft(s), motor drive shaft(s), and/or member formed shaft(s), that can be directly and/or indirectly, and effectively, turned, rotated, and/or pivoted, for one or more of any suitable and effective distance(s) at one or more of any suitable and effective speed(s), velocity(s), and/or rate(s), and at one or more of any suitable and effective time(s), can form the various one or more of any suitable and effective, elongated member(s) (Herein called "Elongated Member(s)" (210)(222)(224)(226)(470)(445)(439)(405).

Figure 16:
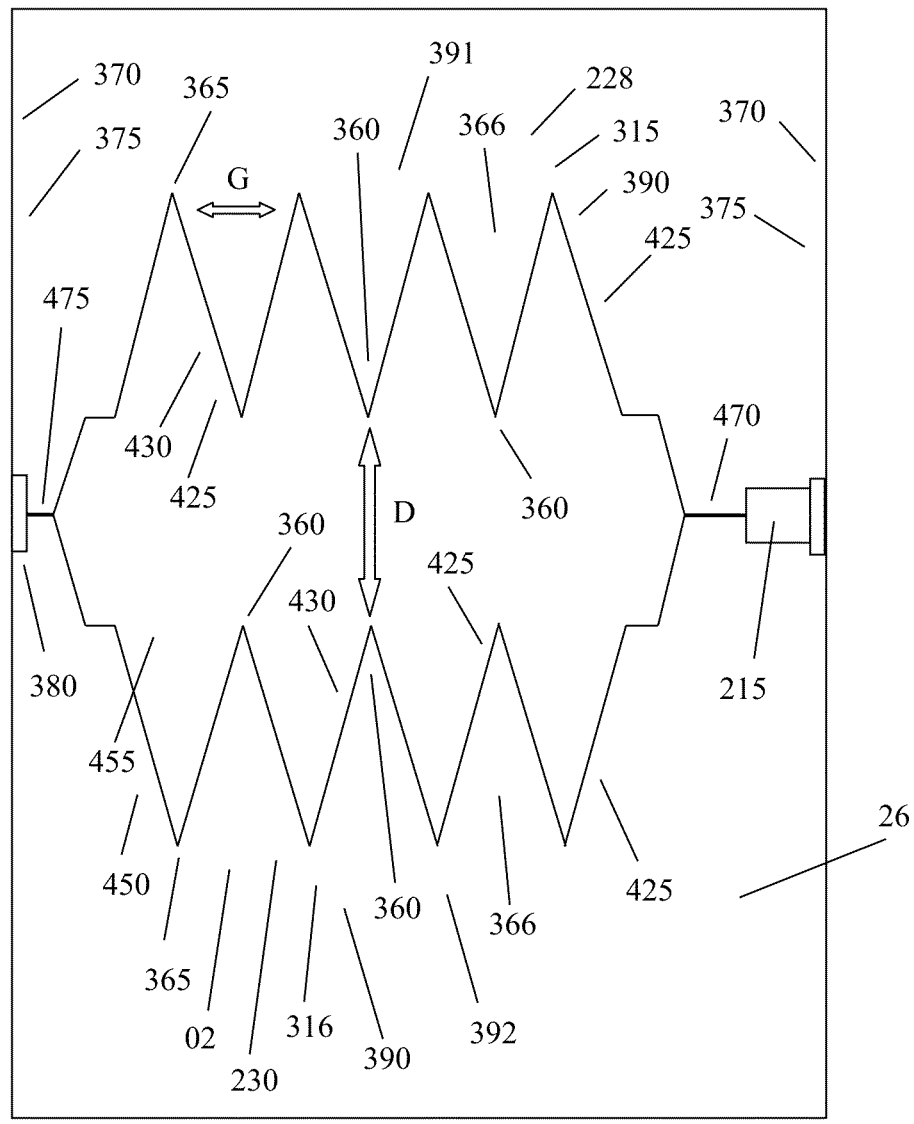
FIG. 16 is a side view of a rotating object(s) holder, located in a treatment chamber, where the various support members that are in contact with the object(s) form a first retaining structure(s) with one or more of any wave shape(s), and an opposing second retaining structure(s) with one or more of any wave shape(s), and where at one end, the various one or more or plurality of members, converge or connect to form at least one shaft(s) and/or elongated member(s) that suitably connects with at least one motor(s) and the opposing is member formed turn shaft.

With reference to FIG. 16, and without being limited, the various one or more, or plurality of any, retention members 228, 230, 315, 316, support member(s) 425, retention structure(s) 390, first retaining structure(s) 391, and second retaining structure(s) 392, can suitable and effectively, converge, merge, interconnect, connect, communicate, fuse, and/or form, at one or more of any suitable end(s), one or more of any suitable and effective, shaft(s), rotation member(s), and/or elongated structure(s) 222 (Herein called "Member Formed Turn Shaft(s)") 475, that can suitably and effectively directly and/or indirectly interface and/or connect with one or more of any suitable and effective, bearing(s), turning and/or motion apparatus(s), and/or turn support bearing(s) 380, known to those skilled in the art.

Figure 17:
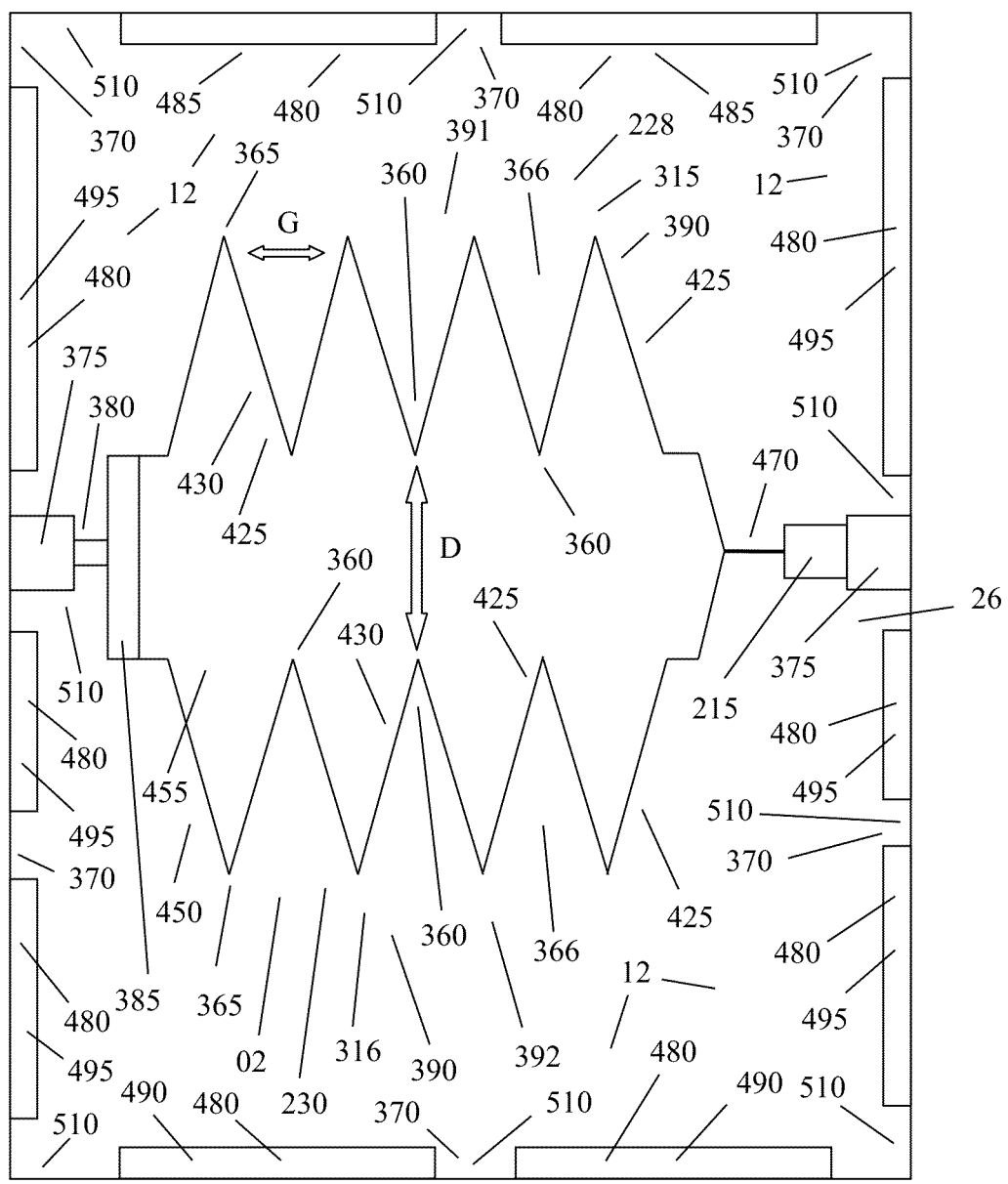
FIG. 17 is a side view of a rotating object(s) holder, located in a treatment chamber, where the various support members that are in contact with the object(s) form a first retaining structure(s) with one or more of any wave shape(s), and an opposing second retaining structure(s) with one or more of any wave shape(s), and where electromagnetic radiation in the form of light in a spectrum visible or invisible to the human eye is used to treat the plurality of objects instead of gas, vapor or aerosol.

Referring to FIG. 17, and without being limited, the Multi-function Treatment Cabinet(s) and/or Chamber(s) Product 1, can also include one or more of any suitable and effective, decontamination system(s) 12, that can include, and without limitation, one or more of any suitable and effective, light emitting system(s), light emitting technology(s), light emitting array(s), light emitting tube(s), light fixture(s), light emitting apparatus(s), light emitting bulb(s), strobe light(s), light emitting LED's, and/or light bulb(s), (Herein called "Light Emitter(s)") 480, for any suitable and effective, anti-bacterial effect, anti-spore effect, anti-fungal effect, bacterial kill, spore kill, fungal kill, decontamination, sanitization, disinfection, high-level disinfection, and/or sterilization, of and/or on, one or more of any and/or all, surface(s) of any object(s) 300, and/or any and/or all surface(s) within one or more of any treatment chamber(s) 26.

Without being limited, the one or more light emitter(s) 480 can be located at and/or with one or more of any suitable and effective, density(s), orientation(s), pattern(s), direction(s), height(s), distance(s), spacing, and/or angle(s), suitably and effectively, inside of, communicating with, interfaced with, and/or mounted to, the treatment chamber(s) 26.

Without being limited, the light emitter(s) 480 can be any suitable and effective, length(s), width(s), height(s), thickness(s), size(s), shape(s), geometry(s), and can be located in one or more of any suitable and effective, density(s) and/or number density(s), per or on one or more of any suitable and effective, area(s), wall(s), and/or location(s), of the treatment chamber(s) 26. Without being limited, the one or more light emitter(s) 480 can be suitably and effectively, located, positioned, and/or mounted, effectively flush to and/or within the interior wall(s), floor(s), and/or ceiling surface(s), within and/or facing, the treatment chamber(s) 26 and/or interior area(s) of the treatment chamber(s) 26, all in a manner known to those skilled in the art.

It is preferred, without limitation, that at least one light emitter(s) 480 emits and shines light from one or more of any suitable and effective treatment chamber(s) 26 top location(s) (Herein called "Top Chamber Light Location(s)") 485 of, interfaced with, communicating with, and/or within, the treatment chamber(s) 26, and emits and shines light effectively into the treatment chamber(s) 26, and/or at least one light emitter(s) 480 emits and shines light from one or more of any suitable and effective treatment chamber(s) 26 bottom location(s) (Herein called "Bottom Chamber Light Location(s)") 490, of, interfaced with, communicating with, and/or within, the treatment chamber(s) 26, and emits and shines light effectively into the treatment chamber(s) 26, and/or at least one light emitter(s) 480 emits and shines light from one or more of any suitable and effective, sides and/or side location(s) and/or left side location(s) and/or right side location(s), of the treatment chamber(s) 26 (Herein called "Chamber Side(s) Light Location(s)") 495, of, interfaced with, communicating with, and/or within, the treatment chamber(s) 26, and emits and shines light effectively into the treatment chamber(s) 26, and/or at least one light emitter(s) 480 emits and shines light from one or more of any suitable and effective location(s) in or at the rear or back of the treatment chamber(s) 26 (Herein called "Rear Chamber Light Location(s)") 500 (not shown), of, interfaced with, communicating with, and/or within, the treatment chamber(s) 26, and emits and shines light effectively into the treatment chamber(s) 26, and/or at least one light emitter(s) 480 emits and shines light from one or more of any suitable and effective location(s) in or at the front of the treatment chamber(s) 26 (Herein called "Front Chamber Light Location(s)") 505 (not shown), of, interfaced with, communicating with, and/or within, the treatment chamber(s) 26, and emits and shines light effectively into the treatment chamber(s) 26.

Without being limited, one or more of any suitable and effective light emitter(s) 480 can be located in, at, and/or to, one or more of any suitable and effective location(s), that are suitably and effectively, adjacent to, communicating with, interfacing with, and/or within, the one or more treatment chamber(s) 26. Without being limited, the one or more light emitter(s) 480 can shine and/or emit any effective light into the treatment chamber(s) 26 at one or more of any suitable and effective angle(s). It is preferred, without limitation, that the one or more light emitter(s) 480 at least emit, project, and/or shine, their output and/or light effectively into the treatment chamber(s) 26. It is also preferred, without limitation, that any effective quantity(s) of any light emitter(s) 480 are incorporated into the design and construction of the treatment chamber(s) 26 and emit their light(s) effectively into the treatment chamber(s) 26. It is further preferred, without limitation, that the light that the one or more and/or various light emitter(s) 480 shines into the treatment chamber(s) 26 reaches and interacts with at least all of the, critical surface(s), effective surface(s), and object 300 surface(s), within the treatment chamber(s) 26, and more preferably, and without limitation, all of the surface(s) within the treatment chamber(s) 26.

Without being limited one or more of any suitable and effective light emitter(s) 480 known to those skilled in the art, can interface with, communicate with, and/or be located within, the treatment chamber(s) 26. Also, and without being limited, the one or more light emitter(s) 480 can emit any light at and/or with, one or more of any suitable and effective attribute(s) known to those skilled in the art such as, but not limited to any effective, light spectrum(s), wavelength(s), power(s), brightness(s), intensity(s), amplitude(s), period(s), pulse(s), pattern(s), and/or frequency(s). Without being limited, the one or more light emitter(s) 480 can also be operated for one or more of any suitable and effective, number of time(s) and/or duration(s) of time(s), all in a manner known to those skilled in the art.

Without being limited, the one or more light emitter(s) 480 can be suitably and effectively located at one or more of any suitable and effective distance(s) from the treated object(s) 300, the rotating object(s) holder and treatment apparatus 2, the at least one first suitable and effective means 228 to hold and release the one or more object(s) 300 within the sealed treatment chamber(s) 26, the at least one second suitable and effective means 230 to hold and release the one or more object(s) 300 within the treatment chamber(s) 26, support member(s) 425 and/or the one or more retention structure(s) 390, and where the effective distance(s) and angle(s) of the emitted light from the light emitter(s) 480 to the various targeted surface(s) are all preferably, and without limitation, known to those skilled in the art.

Also, and without being limited, one or more, any, and/or all, suitable and effective surface(s) within the treatment chamber(s) 26, such as, but not limited to any, ceiling surface(s), wall surface(s), bottom surface(s), bracket(s), member(s), fixture(s), and/or floor surface(s), within the treatment chamber(s) 26, can be lined with, covered with, and/or constructed from, one or more of any suitable and effective light reflective material(s) known to those skilled in the art, such as, but not limited to any suitable and effective, mirror(s), polished aluminum, and/or polished stainless steel (Herein called "Mirrored Surface(s)") 510. Without being limited, the various effectively mirrored and/or polished walls and surface(s) within the treatment chamber(s) 26 can help to increase the efficacy of the one or more treatment cycles that may be used to treat the various surface(s) of the object(s) 300 located within the treatment chamber(s) 26, by reflecting the light within the treatment chamber(s) 26 that is emitted from the one or more light emitter(s) 480, all in a manner known to those skilled in the art.

Without being limited, the various, methods, steps, and apparatus(s), mentioned and described in the present invention for treating and processing the one or more, various, and/or all, surface(s) of the object(s) 300 and/or interior cabinet surface(s), remains the same when solely using the one or more light emitter(s) 480 to treat the various surface(s) and object(s) 300 surface(s), within the treatment chamber(s) 26, except for and excluding the various methods, steps, and apparatus(s) that pertain to drying and/or dehumidifying the various surface(s), object(s) 300 surface(s), and/or area(s), within the treatment chamber(s) 26 after treating the various surface(s) within the treatment chamber(s) 26. Without being limited, applying the light emitted by the one or more light emitter(s) 480 into the treatment chamber(s) 26 and onto the various surface(s) and object(s) 300 surface(s) within the treatment chamber(s) 26, can be exchanged and/or replaced for applying various treatment agent(s) 100 such as, but not limited to any, gas(s), vapor(s), and/or aerosol(s). However, in some situations, and without limitation, it may be required and/or desired to dry and/or dehumidify the various, surface(s), object(s) 300 surface(s), and/or area(s), within the treatment chamber(s) 26 before treating them with the one or more light emitter(s) 480. Without being limited, the atmosphere(s) in the treatment chamber(s) 26 can also be purged and/or filtered before any door(s) 36 are opened by the system operator(s) to access the one one or more treated and processed object(s) 300.

Also, and without being limited, one or more, but preferably and without limitation, all, of any suitable and effective part(s) such as, but not limited to any component(s) of the rotating object(s) holder and treatment apparatus 2, such as, but not limited to any, at least one first suitable and effective means 228 to hold and release the one or more object(s) 300 within the sealed treatment chamber(s) 26, at least one second suitable and effective means 230 to hold and release the one or more object(s) 300 within the treatment chamber(s) 26, one or more retention structure(s) 390, one or more of any support(s), rod(s), shaft(s), connection shaft(s), and/or elongated member(s), that the one or more retention structure(s) 390 may interface with, support member(s) 425, member shaft interface(s) 400, motor drive shaft(s) 405, elongated member(s), shaft(s), and/or member bearing interface(s) 385, can be constructed from one or more of any suitable and effective material(s) known to those skilled in the art, that one or more of any type(s) of light emitted from the one or more light emitter(s) 480 can effectively pass through, and retain any, all, but at least any effective amount(s) and/or level(s), of the emitted light's effective and efficacious properties, such as, but not limited to any, glass(es) and/or quartz(s) that any and/or various types of light and/or any UV light can effectively pass through, various light and/or any UV light transparent glass(es) and/or quartz(s), polymer(s) that any and/or various types of light and/or UV light can effectively pass through, various light and/or any UV light transparent polymer(s).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of at least one of sanitizing, disinfecting, high level disinfecting and sterilization of at least one object, comprising the steps of:
providing a retention structure having a plurality of object support gaps extending outward from said retention structure, said plurality of object support gaps are rigidly fixed, said retention structure is retained inside a treatment enclosure, the at least one object is retained within at least one of said plurality of object support gaps;
applying electromagnetic energy in the form of light in any effective wavelength to the at least one object during a light cycle; and
rotating said retention structure in at least one of a clockwise direction and a counterclockwise direction, at least once during said light cycle.

2. The method of claim 1, further comprising the step of:
providing said retention structure with a first plurality of object support gaps and a second plurality of object support gaps, said first plurality of object support gaps are located opposite said second plurality of object support gaps.

3. The method of claim 2, further comprising the step of:
extending a set screw from an outer perimeter of said retention structure, locating a first switch and a second switch to be actuated by said set screw during a rotation of said retention structure.

4. The method of claim 3, further comprising the step of:
providing a motor, a clockwise relay and a counter clockwise relay, said motor rotates said retention structure, said clockwise relay supplies voltage to said motor for clockwise rotation, said counter clockwise relay supplies voltage to said motor for counter clockwise rotation.

5. The method of claim 4, further comprising the step of:
providing a bracket attached to said treatment enclosure, attaching said motor to said bracket, attaching said first and second switches to said bracket.

6. The method of claim 5, further comprising the step of:
providing said bracket with a base member, a first leg, a second leg, a first switch plate and a second switch plate, said first leg extends outward from a first end of said base member, said second leg extends outward from a second end of said base member, said first switch plate extends outward from one side of said first leg, said second switch plate extends from an opposite side of said first leg.

7. A method of at least one of sanitizing, disinfecting, high level disinfecting and sterilization of at least one object, comprising the steps of:
providing a retention structure having a plurality of object support gaps extending outward from said retention structure, said plurality of object support gaps are rigidly fixed for retaining the at least one object therein, said retention structure is retained inside a treatment enclosure on a horizontal axis, the at least one object is retained within said plurality of object support gaps, at least one of said plurality of object support gaps provides support for the at least one object placed therein of the at least one object;
applying electromagnetic energy in the form of light in any effective wavelength to the at least one object during a light cycle; and
rotating said retention structure in at least one of a clockwise direction and a counterclockwise direction, at least once during said light cycle.

8. The method of claim 7, further comprising the step of:
providing said retention structure with a first plurality of object support gaps and a second plurality of object support gaps, said first plurality of object support gaps are located opposite said second plurality of object support gaps.

9. The method of claim 8, further comprising the step of:
extending a set screw from an outer perimeter of said retention structure, locating a first switch and a second switch to be actuated by said set screw during a rotation of said retention structure.

10. The method of claim 9, further comprising the step of:
providing a clockwise relay and a counter clockwise relay, said motor rotates said retention structure, said clockwise relay supplies voltage to said motor for clockwise rotation, said counter clockwise relay supplies voltage to said motor for counter clockwise rotation.

11. The method of disinfecting a plurality of electrical devices of claim 10, further comprising the step of:
providing a bracket attached to said treatment enclosure, attaching said motor to said bracket, attaching said first and second switches to said bracket.

12. The method of claim 11, further comprising the step of:
providing said bracket with a base member, a first leg, a second leg, a first switch plate and a second switch plate, said first leg extends outward from a first end of said base member, said second leg extends outward from a second end of said base member, said first switch plate extends outward from one side of said first leg, said second switch plate extends from an opposite side of said first leg.

13. A method of at least one of sanitizing, disinfecting, high level disinfecting and sterilization of disinfecting at least one object, comprising the steps of:

providing a retention structure having a plurality of object support gaps extending outward from said retention structure, said plurality of object support gaps are rigidly fixed for retaining the at least one object, said retention structure is retained inside a treatment enclosure on a horizontal axis, the at least one object is retained within said plurality of object support gaps, at least one of said plurality of object support gaps makes contact with the at least one object; and applying electromagnetic energy in the form of light in any effective wavelength to the at least one object, rotating said retention structure in at least one of a clockwise direction and a counter clockwise direction.

14. The method of claim 13, further comprising the step of:

providing said retention structure with a first plurality of object support gaps and a second plurality of object support gaps, said first plurality of object support gaps are located opposite said second plurality of object support gaps.

15. The method of claim 14, further comprising the step of:

extending a set screw from an outer diameter of said retention structure, locating a first switch and a second switch to be actuated by said set screw during a rotation of said retention structure.

16. The method of 15, further comprising the step of:

providing a clockwise relay and a counter clockwise relay, said motor rotates said retention structure, said clockwise relay supplies voltage to said motor for clockwise rotation, said counter clockwise relay supplies voltage to said motor for counter clockwise rotation.

17. The method of claim 16, further comprising the step of:

providing a bracket attached to said treatment enclosure, attaching said motor to said bracket, attaching said first and second switches to said bracket.

\* \* \* \* \*